United States Patent [19]
Sutcliffe et al.

[11] Patent Number: 5,968,817
[45] Date of Patent: Oct. 19, 1999

[54] DNA ENCODING SEROTONIN RECEPTORS

[75] Inventors: J. Gregor Sutcliffe, Cardiff; Mark G. Erlander, Encinitas; Timothy W. Lovenberg, San Diego, all of Calif.

[73] Assignee: The Scripps Research Institute, La Jolla, Calif.

[21] Appl. No.: 08/031,538

[22] Filed: Mar. 15, 1993

[51] Int. Cl.$^6$ ................................................. C12N 15/12
[52] U.S. Cl. .................. 435/325; 536/23.5; 435/69.1; 435/320.1
[58] Field of Search ................ 536/23.5; 435/240.2, 435/320.1, 252.3, 69.1, 325

[56] References Cited

U.S. PATENT DOCUMENTS

| | | |
|---|---|---|
| 5,360,735 | 11/1994 | Weinshank et al. ................. 435/240.2 |
| 5,807,691 | 9/1998 | Amlaiky et al. . |

OTHER PUBLICATIONS

NTIS Publication No. PB93–139335 (Sibley, D.R. et al.) published Oct. 26, 1992.
McAllister, G. et al., *PNAS*, 89: 5517–5521, 1992.
Levy, F.O. et al., *FEBS Letters*, 296 (2):201–206, 1992.
Lovenberg, T.W. et al., *PNAS*, 90:2184–2188, Mar. 1993.
Adham, N. et al., *PNAS*, 90:408–412, Jan. 1993.
Libert, F. et al., *Science*, 244:569–572, 1989.
Amlaiky et al., *J. Biol. Chem.*, 267(28):19761–19764, Oct. 1992.
Zgombick, J.M. et al., *Mol. Pharm.*, 42(2):180–185, 1992.
Monsma, Jr., F.J. et al., *Mol. Pharm.*, 43(3): 320–327, Mar. 1993.
Plassat, J.–L. et al., *EMBO J.*, 11(13):4779–4786, 1992.

*Primary Examiner*—Marianne P. Allen
*Attorney, Agent, or Firm*—Thomas Fitting; Emily Holmes

[57] ABSTRACT

The present invention describes nucleic acid molecules encoding human serotonin receptors, recombinant serotonin receptor proteins, cultured cells expressing recombinant serotonin receptor proteins, antibodies immunoreactive with serotonin receptor proteins, polypeptide serotonin receptor antagonists, oligonucleotide probes used for detecting nucleic acids which encode a human serotonin receptor, and nonhuman transgenic animals which express recombinant human serotonin receptor. Also disclosed are methods for screening for ligand binding to the described serotonin receptors and for serotonin receptor agonists and antagonists, for detection of serotonin receptors in tissues, and for therapeutic treatments involving the described human serotonin receptors.

14 Claims, 12 Drawing Sheets

```
GGTTCCAGTGTGCAGGCATCAGTCCCCAGTTCTGCAGGCGGTTGGTTACTCTGAAGACC        60
ACAAAGAGACTGGGAGAGAGTTGATGCGCTGGACAAAGCTAGACTAAGGAGTCTCAACTGG     120
AAAAAGGGTCTACGAAACCTCAAAAAGAAGAGCGCCTACACAGTTTGGAAAAGAACAAAG      180
GTGGCGCGGCTTAGACTTCTTTTGTGTGCTGGGCCAGTGCCCCCTCGCCCCTCCTGCCTCG     240
CCACCTAACCACAGTTCATGCAATCACGGGCACATCTGCCAGAGAGCCCGAGTCCCTGAA      300
CAATGGAAGTCTCTAACCTCTCAGCGCGCCACCCCTGCATTGCCTTTCCTCCGGACCCCG      360
        M  E  V  S (N) L  B  G  A  T  P  G  I  A  P  P  P  G  P  E      20
AGAGCTGCAGTGACAGCCCAAGTTCCGGCAGAGCATGGATGGGATCCCACCCCAGGGGCTCA    420
        B  C  B  D  B  P  B  B  G  R  B  M  G  B  T  P  G  G  L  I      40
TCTTGTCCGGCCGCGAGCCGCCCTTCTCTGCCTTCACCGTACTCGTGGTAACTCTACTGG     480
        L  B  G  R  E  P  P  F  B  A  P  T  V  L  V  V  T  L  L  V      60
TGTTGCTGATCGCTGCCACCTTCTGCCACTTTCTATGGAATCTAGTTCTGGTGACTATCCTGCGCG 540
        L  L  I  A  A  T  F  L  W  N  L  V  L  V  T  I  L  R  V        80
TCCGCGCCCTTCCACCGTGTGCCAGCCCCGTGTCCTCGACCGCGTCTCGGACGTCC         600
        R  A  F  H  R  V  P  H  N  L  V  A  B  T  A  V  B  D  V  L     100
TGGTGGCCAGACTGGGGCCACTGGAGCCTGAGCGAGTTGTGCGGCGAGTTGTGCGGACGTT     660
        V  V  A  A  L  V  M  P  L  B  V  S  E  L  B  A  G  R  R  W     120
GGCAGCTGGGCAGGAGTCTGTGCACGTGTCTCCTTCGACGTGTGTGCTGCACAG         720
        Q  L  G  R  B  L  C  H  V  W  I  B  F  D  V  L  C  C  T  A     140
CCAGCATCTGGAACGTGGCGGCCACCCGGCCACTCGCGCCCTGACTCGACTGGATCGACACGCGCCACC 780
        S  I  W  N  V  A  A  I  A  L  A  D  R  Y  W  T  I  T  R  H  L   160
TGCAGTACACGCTGCGCCCTCGCGCCCTTCAGCAGCTTCCAGCAGCTTGGCGCTCTTTGGCGTCCTCTCTTGGCGCTGGATCGCACTTATGATCGCACTTATGATCGCACTTATGATCGCAC 840
        Q  Y  L  R  T  L  R  R  R  A  B  A  L  M  I  A  I  T  W  A     180
CACTGTCCGCCCATCGCGCCCCCGCTCGCTCTTGGCTGCTCTTGGCGAAGCCTACGATG      900
        L  B  A  L  I  A  L  A  P  L  L  F  G  W  G  E  A  Y  D  A     200
CTCGGCCTGCAGCCGTTGCCAGGAGCCTTGTACGCCGTCTTCTCCACTTGCCG           960
        R  L  Q  R  C  Q  V  B  Q  E  P  S  Y  A  V  F  B  T  C  G     220
GAGCTTCTACTGCCTGTGCCTCTGGCCGTGCTCTTCGTCTACTGAAGATATACAAAGCCG    1020
        A  F  Y  V  P  L  A  V  V  L  F  V  Y  W  K  I  Y  K  A  A     240
```

FIG.IA

```
CCAAGTTTCGATTCGGCCGCAGACGGCGGGGGGTAGTGCCCCTGCCCGCCACCACGCAGG      1080
 K  F  R  F  G  R  R  R  R  A  V  V  P  L  P  A  T  T  Q  A       260
CAAAGGAAGCACCTCAGGAGTCTGAGACGGTATTCACCGCGTTGCAGAGCGACAGTGG        1140
 K  E  A  P  Q  E  S  E  T  V  F  [T] A  R  C  R  A  T  V  A      280
CCTTCCAGACAAGTGGAGACTCCTGGCGGGAGCAGAAGCGAGCCGCCATGATGG            1200
 P  Q  T  S  G  D [S] W  R  E  Q  K  E  K  R  A  A  M  M  V       300
TGGGGATCTTGATCGGTGTTGTTTGTGCTGGATCCCCCTTCTCCTGACGGAGCTCG          1260
 G  I  L  I  G  V  F  V  L  C  W  I  P  F  F  L  T  E  L  V       320
TCAGCCCGCTCTGCGCCTGCAGCCTGCCACCCATCTGGAAAAGCATATTCCTGTGGCTTG      1320
 S  P  L  C  A  C  S  L  P  P  I  W  K  S  I  F  L  W  L  G       340
GCTATTCAAATTCGTTCTTCAATCCCTTAATCTACACGGCCTTTAATAAGAACTACAACA      1380
 Y  S  N  S  F  F  N  P  L  I  Y  T  A  F  N  K  N  Y  N  N       360
ATGCCTTCAAGAGCCTCTTCACTAAGCAGAGATAAGCAGGGCTGGGGAGATAAAAAGGAA      1440
 A  F  K  S  L  F  T  K  Q  R  *                                  370
GACCGGGGAAGAGAAAGGGGATCTGCCGTCCTCATTCACCAGAGACCTGGGGCTTCTC        1500
CCCGCCGCCCACACCCCCTAACGACACTCCAGAAATCACACCGTAGGGCCTGAATGTT        1560
GAGTTCTCACGAAGTGCTAGTAGACAACGGTTTGCAAATACATCCTTCTACGCCTGTG        1620
ACAGACATTGCTAGTGAATTGTGCTACATTTCTGCACCAGGCAGGAACCCCGCCAAACCC      1680
TTTCCGGTGTATTTTAGGTAGTACTATGTCCCCTACCCCCACATGTGGCAGAGTTG          1740
ATTTGCTTTTGCGTTAGTACATAGCCCTCCTCCCTCAAGGCAATGATTCTCAGTTTAGGATG   1800
TGACTCCTTGACATAGACCTTCCACAGACCCTCCACACAAATGATTCTCAGTTTAGAGAC     1860
GCCTCACACAGGACCCTCCACAAGTGTTCCACACAGACCCTTGCCATCTCAGTTCCTGCCT    1920
GAAGCTTTGTTAAAAAGTGTTCCACACAGACGTCGTCAGATGGCTCAGTAGAGGGGTT        1980
GGGGATTTAGCTCAGTCTGGTAGAGCCCTTGCCTAGGAGCGCAAGGCTCGGTTCGGTCC       2040
CCAGCTCCGAAAAAAACCAAAAAAAAAAAAAAAGATGGCTCAGTAGA                   2100
TGAAGGCGCCTGTCCCCAAGCCTGGTGGCCTTTGAGATACATGTAATGGAAGAAA           2160
TAAAATGATTGCAAGTTGTCTCTGACCTCCAGATATGTGCCATCAGCCCCTCTCCCCCATG    2220
TGCACA                                                             2226
```

```
AAGGGGACACGTGGAGGGAACAGAAGGAGCAAAGGGCAGCCCTCATGGTGGCATCCTCA  1020
 G  D  T  W  R  E  Q  K  E  Q  R  A  A  L  M  V  G  I  L  I   291
TTGGGTGTGTTTGTCCTTGCTCTGGTTCCCCTTCTTTGTTACGGAGCTCATCAGTCCGCTGT 1080
                      L  C  W  F  P  F  F  V  T  E  L  I  S  P  L  C   311
GCTCCTGGGATATCCCGCTCTGGAAGAGCATCTTCCTGTGGCTGGGCTATTCCAACT 1140
 S  W  D  I  P  A  L  W  K  S  I  F  L  W  L  G  Y  S  N  S   331
CCTTCTTCAACCCGCTCATCTACACGGCGTTCAACAGGAGCTACAGCAGTGCTTTTAAGG 1200
 P  F  N  P  L  I  Y  T  A  F  N  R  S  Y  S  S  A  F  K  V   351
TCTTCTTCTCCAAGCAGCAGTGAGAGGCCACATGGGAGTGCCTTCTTCCCGTAGCTTGTA  1260
 F  F  F  S  K  Q  Q  *                                        357
GCTCGGTGGACTGTCCCTGCCCTCACAAACCCCTGTAGTCTGCCCAGCTGTCCAGAGGAACA 1320
AGATCCATCTGCCAAGGCACCAGGTCACATCAGAGCTCAGCTCACTTCAGTTCTGTGC 1380
CCGTGTGCTGGAAGTGTCTCCAGCAGCCACAGGCCTGTCTGCCCAGTGTCTGGGCACT 1440
CTTCCTCACACTGTACCAGCAGCCACAGGCCACAGGAGTTGATCAGAACGAACAGGAGGAGTTCCTCCA 1500
ACTCCACTCCAGCGGGACCATGAGAGGCAGAAGAACAAGGCTGAAACAGGAAGAGTGAG 1560
ACAATAAGGCAGGCACACACCAAGGAGAGGAGACTTAGGCAGGACTGGGATCACATA  1620
CCTGGAACCCTCACACCAGTAAGTTCATAAATCAGTCTGAGCTGTCTGACACAGAGCCTG 1680
GGCTACATAGTAAGAGGCTATTTGCTCTGTCCCAAAGCCAGAGAACTTCCCAGAACAGCAA 1740
TGCACTAGAGAGGCTATTTGCTCTGTGGCTCCCAAATTCTGGTCCTTCTGA 1800
TCACTTCACAGTTCCTGTCTATGCCCTGCTCTGTATGCCCAGTGTATCAAAGACCACCTG 1860
ATATCTGATCACAAGATTCTGTCCCAAACATATCAAGCACCCATTGTGATAAC 1920
AGTGATTCCCTGTCTTTACCATTTGTTCATTGTGAACCACCCTCTAGTTTCCAGTGTCTG 1980
TCTCTGTCTATGCCTGTCTCCCCCACCACCCTTCCATTTCCAGTTTGAAACCACTCTTCAACTC 2040
AGTCTATCAACTGGAAAAGCAAGAATTCTGTCAAATCTGTCAAATTCTGTCAAAAATCTTCATGAAAA 2100
ATCTATCAATTTCACAGAATCTGTCAAATCTGTCAAATTTATTTACTATGGGTTTTTACTGGTA 2155
```

FIG.2B

```
                                                            TAGGTGAAGTG
  1 AAAAACATGCACATATTTTTTTAAAATGTTCTAAAAATAGAAGAGAACAATACTTGAAAC

AGGATGAAAACCAACAGTTGAATGTGCCACACCACG*
 61 CTTCTCTGAACTATGTTTCCCCCTCCTTTGTTACAGGTATTCATTTCTTCAACTATGTAA

121 ACCTTTTAAACAAAAAAATGGATTTTCTAAACTCATCAGACCAAAATTTAACCTCAGAGG
  1                    M  P  F  L  N  S  S  D  Q  N  L  T  S  E  E
                                ▲              ▲
181 AACTGTTAAACCGAATGCCATCCAAAATTCTGGTATCCCTCACTCTGTCTGGCCTGGCCT
 16  L  L  N  R  M  P  S  K  I  L  V  S  L  T  L  S  G  L  A  L
                                                        TM I
241 TGATGACAACCACCATCAACTGCCTCGTGATCACTGCAATCATTGTGACTCGGAAGCTGC
 36  M  T  T  T  I  N  C  L  V  I  T  A  I  I  V  T  R  K  L  H
           S                    A
301 ACCACCCAGCCAACTATTTAATCTGTTCCTTGGCAGTTACAGACTTTCTTGTTGCTGTCC
 56  H  P  A  N  Y  L  I  C  S  L  A  V  T  D  F  L  V  A  V  L
                                                        TM II
361 TGGTTATGCCCTTTAGCATCGTGTACATTGTGAGAGAGAGTTGGATTATGGGACAAGGAC
 76  V  M  P  F  S  I  V  Y  I  V  R  E  S  W  I  M  G  Q  G  L
                                                              V  V
421 TCTGTGACCTTTGGCTGAGTGTTGACATCATCTGCTGTACCTGCTCCATCTTGCACCTGT
 96  C  D  L  W  L  S  V  D  I  I  C  C  T  C  S  I  L  H  L  S
     I         TM III            I
481 CGGCTATAGCGTTGGATAGGTACCGAGCAATCACAGACGCAGTCGAGTATGCCAGGAAGA
116  A  I  A  L  D  R  Y  R  A  I  T  D  A  V  E  Y  A  R  K  R

541 GGACTCCCAGGCATGCTGGCATCACGATTACAACAGTGTGGGTTATATCTGTGTTCATCT
136  T  P  R  H  A  G  I  T  I  T  T  V  W  V  I  S  V  F  I  S
        K                 M           I        I           TM IV
601 CCGTGCCTCCTCTCTTCTGGAGGCACCAAGGAAATAGCCGTGATGATCAGTGTATCATCA
156  V  P  P  L  F  W  R  H  Q  G  N  S  R  D  D  Q  C  I  I  K
     M                       T                 E
```

FIG. 3A

```
661  AACATGACCATATTGTTTCCACAATTTACTCCACGTTTGGAGCCTTCTACATCCCACTTG
176   H  D  H  I  V  S  T  I  Y  S  T  F  G  A  F  Y  I  P  L  V
                        ─────────────────────────────────────────
                           TM V
721  TGTTGATATTGATCCTCTACTACAAAATATACAGAGCAGCAAGGACACTATACCACAAGA
196   L  I  L  I  L  Y  Y  K  I  Y  R  A  A  R  T  L  Y  H  K  R
      ──────────────                       K
781  GACAAGCAAGTCGGATGATAAAGGAGGAACTGAATGGCCAAGTCCTTTTGGAGAGTGGTG
216   Q  A  S  R  M  I  K  E  E  L  N  G  Q  V  L  L  E  S  G  E
               I  A              V
841  AGAAGAGCATTAAACTGGTCTCCACATCCTACATGTTAGAAAAATCCTTATCTGATCCAT
236   K (S) I  K  L  V  S  T  S  Y  M  L  E  K [S] L  S  D  P  S
         T                       V
901  CAACAGACTTTGATAGAATTCACAGCACAGTGAAAAGTCCCAGATCTGAGCTGAAGCACG
256  [T] D  F  D  R  I  H  S (T) V  K (S) P  R  S  E  L  K  H  E
      K                           R     L                    F
961  AGAAATCTTGGAGAAGACAGAAAATCTCAGGCACTCGAGAACGCAAAGCAGCCACTACCC
276   K  S  W  R  R  Q  K  I  S  G  T  R  E  R  K  A  A  T  L
                                                          ──────
1021 TGGGATTGATCTTGGGCGCATTTGTAATATGTTGGTTGCCCTTTTTTGTAAAGGAATTGG
296   G  L  I  L  G  A  F  V  I  C  W  L  P  F  F  V  K  E  L  V
     ────────────────────────────────────────────────────────────
                              TM VI
1081 TTGTTAATATCTGTGAAAAATGTAAAATTTCTGAAGAAATGTCAAATTTTTTGGCATGGC
316   V  N  I  C  E  K  C  K  I  S  E  E  M  S  N  F  L  A  W  L
              V     D     ───────────────────────────────────────
                                                          TM VII
1141 TTGGTTACCTGAATTCTCTTATAAACCCACTGATTTATACCATCTTTAATGAAGACTTTA
336   G  Y  L  N  S  L  I  N  P  L  I  Y  T  I  F  N  E  D  F  K
     ────────────────────────────────────────────────────────
1201 AGAAAGCCTTCCAAAAACTTGTACGATGTCGAAATTAGGATTTAAAAAAAAGCCTATTTT
356   K  A  F  Q  K  L  V  R  C  R  N  *
                                      C
1261 TAAAGGGTAGAGGCTGTATTTCTTGGGGGGGGAGGGATAACTAAATGAATGTAAAGTAAT
1321 AAAAGATTGAAATTTTTAGAGAAAATATATAAAGACTGCTAAAATTATAAGAGGATAAAT
1381 TTATTTTTAATAGTACCAAGAAAATAAGATATACTAATTTGGCCATCATTTTAATGTTCT
1441 CAAAATTAGGAAATAATTTAGGCAGCTCAGCTCATAATATTTTTTCTATGCAATAT
```

FIG. 3B

```
CTTTATTTTTTATTTAATTATTTTTACTTAGGGCTTAAAAAATATCCACCAAAGAGGTTC    60
TTCACCAGTTCATCCCTGACCCCGAGTCTTCTTGAAAAGCAAACGGCTCCCACCCGCTTG   120
TCATTTGCTACAGTGTAGAGGCCAGGGGGTCTGCGGCAGGGCGAGCCCGGGCTGAGCTTT   180
CGCACGGTGCGCATCAGCCGGGCTGCCCAGCAGGGGAAGCCCGTCCCGGTGCGCGCCCGG   240
CGCTGGCGGCTGCCGGAGGCGGTGGCTGGGACGCGGCGCGGCTGCCGCAGGGGAGCGGCG   300
GCGGCGGGCGCGAGGGGCGGGGCGCACTCCGCAACTTCGGCCGCGGCGGCCCGGCGCTCC   360
CGGCCCCGGCGCGCATCGCTGCGGGGCTGCGGTGCGGCCAACCCGGCCAGGCTCGGCTCG   420
CCACCCTGCTCCTCTCGCGTGCCCGTCGGGGACCGCTGGTGCCTCCCGCGGGGAGTCCTC   480
GCCCACGCGTCATCCGCAGAGGCTGGGGGACCCTGGGACGTGCGGGGTCGCGAGGCCGAG   540
CCGGGCGCCCCCAGTGGCCAGCCCCGGACCCCATGGCTGGGCCGCGCGGAGCCGAGCGG   600
GCAAGGTGAATCCAGCCCCGGGGCCGGCTGCCGGAGCGCTTGGCGGGGTCGCCGGCTCCA   660
TGGGCAGCGGCGCTCGGCACGATGATGGACGTTAACAGCAGCGGCCGCCCCGACCTCTAC   720
                         M  M  D  V  N  S  S  G  R  P  D  L  Y   13

GGCCATCTCCGTTCACTCATCCTGCCGGAGGTGGGGCGCGGGCTGCAGGACCTGAGCCCC   780
 G  H  L  R  S  L  I  L  P  E  V  G  R  G  L  Q  D  L  S  P    33

GACGGTGGCGCCCACCCTGTGGTGAGCTCCTGGATGCCGCACCTGCTGAGTGGCTTCCTA   840
 D  G  G  A  H  P  V  V  S  S  W  M  P  H  L  L  S  G  F  L    53

GAGGTGACGGCTAGCCCGGCGCCCACCTGGGACGCGCCACCGGACAATGTCTCAGGCTGC   900
 E  V  T  A  S  P  A  P  T  W  D  A  P  P  D  N  V  S  G  C    73

GGGGAGCAGATCAACTATGGCAGAGTGGAGAAAGTTGTGATCGGCTCCATCCTGACGCTC   960
 G  E  Q  I  N  Y  G  R  V  E  K  V̲  V̲  I̲  G̲  S̲  I̲  L̲  T̲  L̲   93

ATCACGCTGCTGACGATCGCAGGCAACTGCCTGGTGGTGATCTCGGTGTGCTTCGTCAAG  1020
 I̲  T̲  L̲  L̲  T  I  A  G  N  C  L  V  V  I  S  V  C  F  V  K   113
    TM I
AAGCTCCGCCAGCCCTCCAACTACCTGATTGTGTCCCTGGCGCTGGCTGACCTCTCGGTG  1080
 K  L  R  Q  P  S  N  Y  L̲  I̲  V̲  S̲  L̲  A̲  L̲  A̲  D̲  L̲  S̲  V̲  133
                            TM II
GCCGTGGCGGTCATGCCTTTCGTTAGTGTCACCGACCTCATCGGGGGCAAGTGGATCTTC  1140
 A̲  V̲  A̲  V̲  M̲  P̲  F̲  V̲  S̲  V̲  T  D  L  I  G  G  K  W  I  F  153

GGCCACTTCTTCTGCAACGTCTTCATCGCCATGGACGTCATGTGCTGCACGGCCTCGATC  1200
 G  H  F  F  C  N  V̲  F̲  I̲  A̲  M̲  D̲  V̲  M̲  C̲  C̲  T̲  A̲  S̲  I̲  173
                                        TM III
ATGACCCTGTGCGTGATCAGCATCGACAGGTACCTTGGGATCACGAGACCCCTCACGTAC  1260
 M̲  T̲  L̲  C̲  V̲  I̲  S̲  I  D  R  Y  L  G  I  T  R  P  L  T  Y   193
```

FIG. 5A

```
CCGGTGAGGCAAAATGGGAAATGTATGGCCAAAATGATTCTGTCGGTCTGGCTGCTCTCT   1320
 P  V  R  Q  N  G  K  C  M  A  K  M  I  L  S  V  W  L  L  S    213
                            ─────────────────────────────────
                                               TM IV
GCCTCCATCACCTTACCTCCTCTCTTCGGATGGGCTCAGAATGTGAACGATGACAAAGTG   1380
 A  S  I  T  L  P  P  L  F  G  W  A  Q  N  V  N  D  D  K  V    233
 ──────────────────────────────

TGCTTGATCAGCCAGGATTTTGGCTACACGATCTACTCCACTGCGGTGGCGTTTTATATC   1440
 C  L  I  S  Q  D  F  G  Y  T  I  Y  S  T  A  V  A  F  Y  I    253
                ──────────────────────────────────────────────
                                                  TM V
CCCATGTCGGTCATGCTGTTCATGTACTATCAGATTTACAAGGCCGCCAGGAAGAGTGCA   1500
 P  M  S  V  M  L  F  M  Y  Y  Q  I  Y  K  A  A  R  K  S  A    273
 ──────────────────────────

GCCAAACACAAGTTCCCCAGGCTTCCCACGCGTGCAGCCGGAGAGTGTCATCTCCCTGAAT   1560
 A  K  H  K  F  P  G  F  P  R  V  Q  P  E  S  V  I  S  L  N    293

GGTGTGGTGAAGCTCCAGAAGGAGGTGGAAGAGTGTGCGAACCTTTCGAGACTGCTCAAA   1620
 G  V  V  K  L  Q  K  E  V  E  E  C  A  N  L  S  R  L  L  K    313

CACGAAAGGAAAAACATCTCCATCTTCAAGCGGGAACAGAAAGCAGCCACTACCTTGGGG   1680
 H  E  R  K  N  I  S  I  F  K  R  E  Q  K  A  A  T  T  L  G    333
                                            ──────────────────
ATCATCGTGGGAGCCTTCACTGTGTGCTGGCTGCCGTTTTTCCTCTTGTCCACAGCCCGC   1740
 I  I  V  G  A  F  T  V  C  W  L  P  F  F  L  L  S  T  A  R    353
 ────────────────────────────────────────────────
        TM VI
CCCTTTATCTGTGGCACCTCCTGTAGCTGCATTCCTCTGTGGGTGGAGAGGACATGTCTG   1800
 P  F  I  C  G  T  S  C  S  C  I  P  L  W  V  E  R  T  C  L    373
                            ──────────────────────────────────
TGGCTGGGCTATGCAAACTCTCTCATTAATCCTTTTATATATGCCTTCTTCAACCGGGAC   1860
 W  L  G  Y  A  N  S  L  I  N  P  F  I  Y  A  F  F  N  R  D    393
 ──────────────────────────────────────
        TM VII
CTGAGGACCACCTATCGTAGCCTACTCCAGTGCCAGTACCGGAATATCAACCGGAAGCTC   1920
 L  R  T  T  Y  R  S  L  L  Q  C  Q  Y  R  N  I  N  R  K  L    413

TCTGCTGCAGGCATGCATGAAGCCCTGAAACTTGCTGAGAGGCCCGAGAGATCCGAGTTT   1980
 S  A  A  G  M  H  E  A  L  K  L  A  E  R  P  E  R  S  E  F    433

GTGCTGTAAGACAAAACTCTGACCACTGTGGGAAAAAGGGTCATGATACATGATCCAGAG   2040
 V  L                                                           435
```

FIG. 5B

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 2226 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GGTTCCCAGT GTGCAGGCAT CAGTCCCCAG TTCTGCAGGC GGTTGGTTAC TCTGAAGACC      60

ACAAAGAGAC TGGGAGAGGT TGATGCGCTG GACAAAGCTA GACTAAGGAG TCTCAACTGG     120

AAAAAAGGGT CTACGAAAAC CTCAAAAAAG AAGCGCCTAC AGTTTGGAAA AAGAACAAAG     180

GTGGCGCGGC TTAGACTTCT TTTTGTGTTG CTGGGCTCGC GCAGTGCCCC TCCTGCCTCG     240

CCACCTAACC ACAGTTCATG CAATCACGGG CACATCTGCC AGAGAGCCCG AGTCCCTGAA     300

CAATGGAAGT CTCTAACCTC TCAGGCGCCA CCCCTGGCAT TGCCTTTCCT CCGGGACCCG     360

AGAGCTGCAG TGACAGCCCA AGTTCCGGCA GAAGCATGGG ATCCACCCCA GGGGGGCTCA     420

TCTTGTCCGG CCGCGAGCCG CCCTTCTCTG CCTTCACCGT ACTCGTGGTA ACTCTACTGG     480

TGTTGCTGAT CGCTGCCACT TTCTTATGGA ATCTGCTAGT TCTGGTGACT ATCCTGCGCG     540

TCCGCGCCTT CCACCGTGTG CCACATAACT TGGTAGCCTC GACCGCCGTC TCGGACGTCC     600

TGGTGGCGGC TCTGGTGATG CCACTGAGCC TGGTGAGCGA GTTGTCGGCT GGGCGACGTT     660

GGCAGCTGGG CAGGAGTCTG TGCCACGTGT GGATCTCCTT CGACGTGTTG TGCTGCACAG     720

CCAGCATCTG GAACGTGGCG GCCATCGCCC TGGATCGCTA CTGGACTATC ACGCGCCACC     780

TGCAGTACAC GCTGCGCACC CGGCGCCGCG CTTCAGCACT TATGATCGCG ATCACCTGGG     840
```

```
CACTGTCCGC CCTCATCGCG CTCGCCCCGC TGCTCTTTGG CTGGGGCGAA GCCTACGATG      900

CTCGGCTGCA GCGTTGCCAG GTGAGCCAGG AGCCTTCGTA CGCCGTCTTC TCCACCTGCG      960

GAGCTTTCTA CGTGCCTCTG GCCGTGGTGC TCTTCGTCTA CTGGAAGATA TACAAAGCCG     1020

CCAAGTTTCG ATTCGGCCGC AGACGGCGGG CGGTAGTGCC CCTGCCCGCC ACCACGCAGG     1080

CAAAGGAAGC ACCTCAGGAG TCTGAGACGG TATTCACCGC GCGTTGCAGA GCGACAGTGG     1140

CCTTCCAGAC AAGTGGAGAC TCCTGGCGGG AGCAGAAGGA GAAGCGAGCC GCCATGATGG     1200

TGGGGATCTT GATCGGTGTG TTTGTGCTGT GCTGGATCCC CTTCTTCCTG ACGGAGCTCG     1260

TCAGCCCGCT CTGCGCCTGC AGCCTGCCAC CCATCTGGAA AGCATATTC CTGTGGCTTG      1320

GCTATTCAAA TTCGTTCTTC AATCCCTTAA TCTACACGGC CTTTAATAAG AACTACAACA     1380

ATGCCTTCAA GAGCCTCTTT ACTAAGCAGA GATAAGCAGG GCTGGGGAGA TAAAAAGGAA     1440

GACCGGGGAA GAGAAAGGGG ATCTGCCGTC TCATTTCAC CAGAGACCTG GGGGCTTCTC      1500

CCCGCCGCCC ACACCCCCCT AACGACACTC CAGAAATCAC ACCGTAGGGC CTGGAATGTT     1560

GAGTTCTCAC GAAGGTAGAC AACGGTTTGG CAAATACATC CATGCCTTCT ACGCGTCGTG     1620

ACAGACATTG CTAGTGAATT GTGCTACATT TCTGCACCAG GCAGGAACCC CGCCAAACCC     1680

TTTCCGGGTG TATTTTAGGT ATTATTGCTC ATTTGTCAGA CTCCACATGT GGCAGAGTTG     1740

ATTTGCTTTT GCGTTAGTAC TATGTCCCTC AGTGAGGGTC TCTTGGGGCT CTCCTGAGAC     1800

TGACTCCTTG ACATAGCCTC TCCTCTACCC CTTATCCATC AGAGCACTTT ACCTTTCTTA     1860

GCCTCACACA GGACCTCCAC AAGGCAATGA TTCTCAGTTT AGGAAGAGAT GTCCTCGCCT     1920

GAAGCTTTGT TAAAAAGTGT TCCACACAGA CGTCGTCAAG ATGGCTCAGT AGAGGGGGTT     1980

GGGGATTTAG CTCAGTGGTA GAGCCCTTGC CTAGGGAGCG CAAGGCCCTG GGTTCGGTCC     2040

CCAGCTCCGA AAAAAGAAC CAAAAAAAAA AAAAAAAAA AAAAAAGATG GCTCAGTAGA       2100

TGAAGGCGCC TGTCCCCAAG CCTGGTGGCC TGCTTTTGAG ATACATGTAA TGGAAGGAAA     2160

TAAAATGATT GCAAGTTGTC TCTGACCTCC AGATATGTGC CATCAGCCCT CTCCCCCATG     2220

TGCACA                                                                 2226
```

(2) INFORMATION FOR SEQ ID NO:2:

(i) SEQUENCE CHARACTERISTICS:
        (A) LENGTH: 370 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Val Cys Asn Leu Ser Gly Ala Thr Pro Gly Ile Ala Phe Pro
  1               5                  10                  15

Pro Gly Pro Glu Ser Cys Ser Asp Ser Pro Ser Ser Gly Arg Ser Met
                 20                  25                  30

Gly Ser Thr Pro Gly Gly Leu Ile Leu Ser Gly Arg Glu Pro Pro Phe
             35                  40                  45

Ser Ala Phe Thr Val Leu Val Thr Leu Val Leu Leu Ile Ala
         50                  55                  60

Ala Thr Phe Leu Trp Asn Leu Val Leu Val Thr Ile Leu Arg Val
     65                  70                  75              80

Arg Ala Phe His Arg Val Pro His Asn Leu Val Ala Ser Thr Ala Val
                 85                  90                  95

Ser Asp Val Leu Val Ala Ala Leu Val Met Pro Leu Ser Leu Val Ser
                100                 105                 110
```

```
Glu Leu Ser Ala Gly Arg Arg Trp Gln Leu Gly Arg Ser Leu Cys His
            115                 120                 125

Val Trp Ile Ser Phe Asp Val Leu Cys Cys Thr Ala Ser Ile Trp Asn
130                 135                 140

Val Ala Ala Ile Ala Leu Asp Arg Tyr Trp Thr Ile Thr Arg His Leu
145                 150                 155                 160

Gln Tyr Thr Leu Arg Thr Arg Arg Ala Ser Ala Leu Met Ile Ala
                165                 170                 175

Ile Thr Trp Ala Leu Ser Ala Leu Ile Ala Leu Ala Pro Leu Leu Phe
            180                 185                 190

Gly Trp Gly Glu Ala Tyr Asp Ala Arg Leu Gln Arg Cys Gln Val Ser
            195                 200                 205

Gln Glu Pro Ser Tyr Ala Val Phe Ser Thr Cys Gly Ala Phe Tyr Val
            210                 215                 220

Pro Leu Ala Val Val Leu Phe Val Tyr Trp Lys Ile Tyr Lys Ala Ala
225                 230                 235                 240

Lys Phe Arg Phe Gly Arg Arg Arg Arg Ala Val Val Pro Leu Pro Ala
                245                 250                 255

Thr Thr Gln Ala Lys Glu Ala Pro Gln Glu Ser Glu Thr Val Phe Thr
            260                 265                 270

Ala Arg Cys Arg Ala Thr Val Ala Phe Gln Thr Ser Gly Asp Ser Trp
            275                 280                 285

Arg Glu Gln Lys Glu Lys Arg Ala Ala Met Met Val Gly Ile Leu Ile
290                 295                 300

Gly Val Phe Val Leu Cys Trp Ile Pro Phe Phe Leu Thr Glu Leu Val
305                 310                 315                 320

Ser Ala Leu Cys Ala Cys Ser Leu Pro Pro Ile Trp Lys Ser Ile Phe
                325                 330                 335

Leu Trp Leu Gly Tyr Ser Asn Ser Phe Phe Asn Pro Leu Ile Tyr Thr
            340                 345                 350

Ala Phe Asn Lys Asn Tyr Asn Asn Ala Phe Lys Ser Leu Phe Thr Lys
            355                 360                 365

Gln Arg
370
```

(2) INFORMATION FOR SEQ ID NO:3:

(i) SEQUENCE CHARACTERISTICS:
        (A) LENGTH: 2155 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

```
GCTCCGGACT CTCACTGGGT GGAGACTGAG GTCAGGTTCT TGGCTCTTGG CAGAATCCTC      60

TCCACTGGCC AGCGGTTGCA AACATCTAAA TTGACTTCAG TGAACTCGGT GACTGCATTG     120

AGTCTAAACG CAGGTGTGCT GGGCCAGCAA TGGATCTGCC TATAAACTTG ACCTCCTTTT     180

CTCTCTCTAC TCCCTCCACT TTGGAACCTA ACCGCAGCTT GGACACGGAA GCCCTGCGCA     240

CTAGTCAGTC TTTTCTCTCA GCTTTCCGAG TGCTAGTCCT GACTTTGCTG GGCTTTCTAG     300

CTGCCGCCAC GTTCACTTGG AACCTGCTGG TGCTGGCCAC CATCCTCAGG GTACGCACCT     360
```

```
TCCACCGAGT ACCACACAAC CTGGTAGCAT CCATGGCTAT CTCGGATGTG CTAGTAGCTG      420

TGCTGGTTAT GCCTCTGAGC CTGGTACATG AACTGTCTGG GCGCCGCTGG CAGCTGGGCC      480

GGCGTCTATG CCAGCTGTGG ATTGCGTGTG ACGTCCTCTG CTGTACTGCC AGCATCTGGA      540

ATGTGACAGC AATAGCTTTG GACCGCTACT GGTCAATAAC GCGCCACCTG GAGTACACAC      600

TCCGTGCCCG CAAGCGTGTC TCCAACGTGA TGATCCTGCT CACTTGGGCA CTCTCCGCTG      660

TCATCTCTCT GGCTCCGCTG CTCTTTGGCT GGGGAGAGAC TTACTCGGAG CTCAGTGAAG      720

AATGCCAGGT CAGTCGCGAG CCTTCCTACA CCGTGTTCTC CACTGTGGGC GCCTTCTACC      780

TGCCGCTGTG TGTGGTGCTC TTTGTATACT GGAAGATTTA CAAGGCTGCG AAGTTCCGCA      840

TGGGCTCCAG GAAGACCAAC AGCGTCTCCC CCATACCTGA AGCTGTGGAG GTGAAGGACG      900

CTTCACAACA TCCCCAGATG GTGTTCACTG TCCGTCACGC CACCGTCACC TTCCAGACAG      960

AAGGGGACAC GTGGAGGGAA CAGAAGGAGC AAAGGGCAGC CCTCATGGTG GGCATCCTCA     1020

TTGGGGTGTT TGTCCTCTGC TGGTTCCCCT TCTTTGTTAC GGAGCTCATC AGTCCGCTGT     1080

GCTCCTGGGA TATCCCTGCC CTCTGGAAGA GCATCTTCCT GTGGCTGGGC TATTCCAACT     1140

CCTTCTTCAA CCCGCTCATC TACACGGCGT TCAACAGGAG CTACAGCAGT GCTTTTAAGG     1200

TCTTCTTCTC CAAGCAGCAG TGAGAGGCCA CATGGGAGTG CCTTCTTCCC GTAGCTTGTA     1260

GCTCGGTGGA CTGTCCTGCC TCACAAACCC CTGTAGTCTG CCCAGCTGTC CAGAGGAACA     1320

AGATCCATCT GCCAAGGGCA CCAGGGTCAC ATCAGAGCTC AGCTCACTTC AGTTCTGTGC     1380

CCGTGTGCTG GAAGGTGTCT CCTATAGGCT CTGGTAGCTT GTGTCCCCAG TCTGGGCACT     1440

CTTCCTCACA CTGTACCAGC AGCCACAGGC CTGGCCCACA ACGTGCCCAT TTCTCCTCCA     1500

ACTCCACTCC AGCGGGACCA TGAGAAGTTT GATCAGAACG AACAGGAGGA AGGAAGAGAG     1560

ACAATAAGGC AGGCAGAGAG AGGCAGAAAG AACAAGGCTG AAAGCCAGTG GGATCACATA     1620

CCTGGAACCC TCACACCAAG GAGACTTAGG CAGGTAGAAC AGGAATTTGG AGCCATCCTG     1680

GGCTACATAG TAAGTTCATA AATCAGTCTG AGCTGTCTGA CACAGACTTA GCAACAGCAA     1740

TGCACTAGAG AGGCTATTTG AAAAGCAGAG ACCATAAGGG CAAACTTCCC AGAACAGCCC     1800

TCACTTCACA GTTCTGCTCT GTGGTCCTGC AGTGTATGGC CCAATTCTGG GTCCTTCTGA     1860

ATATCTGATC ACAAGATTCT GTCCCCAAAC ATATCAAAGC ACCATCCCAT TTGTGATAAC     1920

AGTGATTCCT GTCTTTACCA TTTGTTCATT GTGAACCCAA AGTCTCCCTC TGTCTGTCTG     1980

TCTCTGTCTA TGCCTGTCTC CCCACCACCA CCACCTCTAG TTTCCAGTTA AAATCAACTC     2040

AGTCTATCAA CTGGAAAAGC AAAATATTTC CTTCCATTTT GAAACCACTC TTCATGAAAA     2100

ATCTATCAAT TCACAGAAT CTGTCAAATT TATTTACTAT GGGTTTTTAC TGGTA           2155
```

(2) INFORMATION FOR SEQ ID NO:4:

(i) SEQUENCE CHARACTERISTICS:
        (A) LENGTH: 357 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Leu Pro Ile Asn Leu Thr Ser Phe Ser Leu Ser Thr Pro Ser
1               5                   10                  15

Thr Leu Glu Pro Asn Arg Ser Leu Asp Thr Glu Ala Leu Arg Thr Ser
            20                  25                  30
```

-continued

```
Gln Ser Phe Leu Ser Ala Phe Arg Val Leu Val Leu Thr Leu Leu Gly
         35                  40                  45

Phe Leu Ala Ala Ala Thr Phe Thr Trp Asn Leu Leu Val Leu Ala Thr
 50                  55                  60

Ile Leu Arg Val Arg Thr Phe His Arg Val Pro His Asn Leu Val Ala
 65                  70                  75                  80

Ser Met Ala Ile Ser Asp Val Leu Val Ala Val Leu Val Met Pro Leu
                 85                  90                  95

Ser Leu Val His Glu Leu Ser Gly Arg Arg Trp Gln Leu Gly Arg Arg
                100                 105                 110

Leu Cys Gln Leu Trp Ile Ala Cys Asp Val Leu Cys Cys Thr Ala Ser
            115                 120                 125

Ile Trp Asn Val Thr Ala Ile Ala Leu Asp Arg Tyr Trp Ser Ile Thr
130                 135                 140

Arg His Leu Glu Tyr Thr Leu Arg Ala Arg Lys Arg Val Ser Asn Val
145                 150                 155                 160

Met Ile Leu Leu Thr Trp Ala Leu Ser Ala Val Ile Ser Leu Ala Pro
                165                 170                 175

Leu Leu Phe Gly Trp Gly Thr Tyr Ser Glu Leu Ser Glu Glu Cys
                180                 185                 190

Gln Val Ser Arg Glu Pro Ser Tyr Thr Val Phe Ser Thr Val Gly Ala
            195                 200                 205

Phe Tyr Leu Pro Leu Cys Val Val Leu Phe Val Tyr Trp Lys Ile Tyr
210                 215                 220

Lys Ala Ala Lys Phe Arg Met Gly Ser Arg Lys Thr Asn Ser Val Ser
225                 230                 235                 240

Pro Ile Pro Glu Ala Val Glu Val Lys Asp Ala Ser Gln His Pro Gln
                245                 250                 255

Met Val Phe Thr Val Arg His Ala Thr Val Thr Phe Gln Thr Glu Gly
                260                 265                 270

Asp Thr Trp Arg Glu Gln Lys Glu Gln Arg Ala Ala Leu Met Val Gly
            275                 280                 285

Ile Leu Ile Gly Val Phe Val Leu Cys Trp Phe Pro Phe Phe Val Thr
290                 295                 300

Glu Leu Ile Ser Pro Leu Cys Ser Trp Asp Ile Pro Ala Leu Trp Lys
305                 310                 315                 320

Ser Ile Phe Leu Trp Leu Gly Tyr Ser Asn Ser Phe Phe Asn Pro Leu
                325                 330                 335

Ile Tyr Thr Ala Phe Asn Arg Ser Tyr Ser Ser Ala Phe Lys Val Phe
                340                 345                 350

Phe Ser Lys Gln Gln
            355
```

(2) INFORMATION FOR SEQ ID NO:5:

(i) SEQUENCE CHARACTERISTICS:
      (A) LENGTH: 1496 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

-continued

```
AAAAACATGC ACATATTTTT TTAAAATGTT CTAAAAATAG AAGAGAACAA TACTTGAAAC      60
CTTCTCTGAA CTATGTTTCC CCCTCCTTTG TTACAGGTAT TCATTTCTTC AACTATGTAA     120
ACCTTTTAAA CAAAAAAATG GATTTTCTAA ACTCATCAGA CCAAAATTTA ACCTCAGAGG     180
AACTGTTAAA CCGAATGCCA TCCAAAATTC TGGTATCCCT CACTCTGTCT GGCCTGGCCT     240
TGATGACAAC CACCATCAAC TGCCTCGTGA TCACTGCAAT CATTGTGACT CGGAAGCTGC     300
ACCACCCAGC CAACTATTTA ATCTGTTCCT TGGCAGTTAC AGACTTTCTT GTTGCTGTCC     360
TGGTTATGCC CTTTAGCATC GTGTACATTG TGAGAGAGAG TTGGATTATG GGACAAGGAC     420
TCTGTGACCT TTGGCTGAGT GTTGACATCA TCTGCTGTAC CTGCTCCATC TTGCACCTGT     480
CGGCTATAGC GTTGGATAGG TACCGAGCAA TCACAGACGC AGTCGAGTAT GCCAGGAAGA     540
GGACTCCCAG GCATGCTGGC ATCACGATTA CAACAGTGTG GGTTATATCT GTGTTCATCT     600
CCGTGCCTCC TCTCTTCTGG AGGCACCAAG GAAATAGCCG TGATGATCAG TGTATCATCA     660
AACATGACCA TATTGTTTCC ACAATTTACT CCACGTTTGG AGCCTTCTAC ATCCCACTTG     720
TGTTGATATT GATCCTCTAC TACAAAATAT ACAGAGCAGC AAGGACACTA TACCACAAGA     780
GACAAGCAAG TCGATGATA AAGGAGGAAC TGAATGGCCA AGTCCTTTTG GAGAGTGGTG     840
AGAAGAGCAT TAAACTGGTC TCCACATCCT ACATGTTAGA AAAATCCTTA TCTGATCCAT     900
CAACAGACTT TGATAGAATT CACAGCACAG TGAAAAGTCC CAGATCTGAG CTGAAGCACG     960
AGAAATCTTG GAGAAGACAG AAAATCTCAG GCACTCGAGA ACGCAAAGCA GCCACTACCC    1020
TGGGATTGAT CTTGGGCGCA TTTGTAATAT GTTGGTTGCC CTTTTTTGTA AAGGAATTGG    1080
TTGTTAATAT CTGTGAAAAA TGTAAAATTT CTGAAGAAAT GTCAAATTTT TTGGCATGGC    1140
TTGGTTACCT GAATTCTCTT ATAAACCCAC TGATTTATAC CATCTTTAAT GAAGACTTTA    1200
AGAAAGCCTT CCAAAAACTT GTACGATGTC GAAATTAGGA TTTAAAAAAA AGCCTATTTT    1260
TAAAGGGTAG AGGCTGTATT TCTTGGGGGG GGAGGGATAA CTAAATGAAT GTAAAGTAAT    1320
AAAAGATTGA AATTTTTAGA GAAAATATAT AAAGACTGCT AAAATTATAA GAGGATAAAT    1380
TTATTTTTAA TAGTACCAAG AAAATAAGAT ATCCTAATTT GGCCATCATT TTAATGTTCT    1440
CAAAATTAGG AAATAATTTA GGCAGCTCAG CTCATAATAT TTTTTCTATG CAATAT        1496
```

(2) INFORMATION FOR SEQ ID NO:6:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

```
TAGGTGAAGT GAGGATGAAA ACCAACAGTT GAATGTGCCA CACCACG                    47
```

(2) INFORMATION FOR SEQ ID NO:7:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO:7:

```
Met Asp Phe Leu Asn Ser Ser Asp Gln Asn Leu Thr Ser Glu Glu Leu
1               5                   10                  15
Leu Asn Arg Met Pro Ser Lys Ile Leu Val Ser Leu Thr Leu Ser Gly
            20                  25                  30
Leu Ala Leu Met Thr Thr Thr Ile Asn Cys Leu Val Ile Thr Ala Ile
                35                  40                  45
Ile Val Thr Arg Lys Leu His His Pro Ala Asn Tyr Leu Ile Cys Ser
50                  55                  60
Leu Ala Val Thr Asp Phe Leu Val Ala Val Leu Val Met Pro Phe Ser
65                  70                  75                  80
Ile Val Tyr Ile Val Arg Glu Ser Trp Ile Met Gly Gln Gly Leu Cys
                85                  90                  95
Asp Leu Trp Leu Ser Val Asp Ile Ile Cys Cys Thr Cys Ser Ile Leu
            100                 105                 110
His Leu Ser Ala Ile Ala Leu Asp Arg Tyr Arg Ala Ile Thr Asp Ala
            115                 120                 125
Val Glu Tyr Ala Arg Lys Arg Thr Pro Arg His Ala Gly Ile Thr Ile
130                 135                 140
Thr Thr Val Trp Val Ile Ser Val Phe Ile Ser Val Pro Pro Leu Phe
145                 150                 155                 160
Trp Arg His Gln Gly Asn Ser Arg Asp Asp Gln Cys Ile Ile Lys His
                165                 170                 175
Asp His Ile Val Ser Thr Ile Tyr Ser Thr Phe Gly Ala Phe Tyr Ile
            180                 185                 190
Pro Leu Val Leu Ile Leu Ile Leu Tyr Tyr Lys Ile Tyr Arg Ala Ala
            195                 200                 205
Arg Thr Leu Tyr His Lys Arg Gln Ala Ser Arg Met Ile Lys Glu Glu
210                 215                 220
Leu Asn Gly Gln Val Leu Leu Glu Ser Gly Glu Lys Ser Ile Lys Leu
225                 230                 235                 240
Val Ser Thr Ser Tyr Met Leu Glu Lys Ser Leu Ser Asp Pro Ser Thr
                245                 250                 255
Asp Phe Asp Arg Ile His Ser Thr Val Lys Ser Pro Arg Ser Glu Leu
            260                 265                 270
Lys His Glu Lys Ser Trp Arg Arg Gln Lys Ile Ser Gly Thr Arg Glu
            275                 280                 285
Arg Lys Ala Ala Thr Thr Leu Gly Leu Ile Leu Gly Ala Phe Val Ile
290                 295                 300
Cys Trp Leu Pro Phe Phe Val Lys Glu Leu Val Val Asn Ile Cys Glu
305                 310                 315                 320
Lys Cys Lys Ile Ser Glu Glu Met Ser Asn Phe Leu Ala Trp Leu Gly
                325                 330                 335
Tyr Leu Asn Ser Leu Ile Asn Pro Leu Ile Tyr Thr Ile Phe Asn Glu
            340                 345                 350
Asp Phe Lys Lys Ala Phe Gln Lys Leu Val Arg Cys Arg Asn
            355                 360                 365
```

(2) INFORMATION FOR SEQ ID NO:8:

(i) SEQUENCE CHARACTERISTICS:
        (A) LENGTH: 1554 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

```
ACTGTTCTCA TTAAATTTCT TAAATAAAAA GGAAAACTAA AACCTTCAAT CTGAACCTCA      60
TTTTTTTAAT CTATAGAATA TTCTGGGTAA ACATAACATA CACTTTTTAA AAATTATTCT     120
GAAAGGAAGA GAAAAGTTCT TGAAGCCTTC TCTGAACTGT TTTTTCTCTT CCCTTGTTAC     180
AGGTATCCAT TTTTCAGCTA TATTAATCTT TAAAACAAA GAAATGGAT TTCTTAAATT      240
CATCTGATCA AAACTTGACC TCAGAGGAAC TGTTAAACAG AATGCCATCC AAAATTCTGG     300
TGTCCCTCAC TCTGTCTGGG CTGGCACTGA TGACAACAAC TATCAACTCC CTTGTGATCG     360
CTGCAATTAT TGTGACCCGG AAGCTGCACC ATCCAGCCAA TTATTTAATT TGTTCCCTTG     420
CAGTCACAGA TTTTCTTGTG GCTGTCCTGG TGATGCCCTT CAGCATTGTG TATATTGTGA     480
GAGAGAGCTG GATTATGGGG CAAGTGGTCT GTGACATTTG GCTGAGTGTT GACATTACCT     540
GCTGCACGTG CTCCATCTTG CATCTCTCAG CTATAGCTTT GGATCGGTAT CGAGCAATCA     600
CAGATGCTGT TGAGTATGCC AGGAAAAGGA CTCCAAAGCA TGCTGGCATT ATGATTACAA     660
TAGTTTGGAT TATATCTGTT TTTATCTCTA TGCCTCCTCT ATTCTGGAGG CACCAAGGAA     720
CTAGCAGAGA TGATGAATGC ATCATCAAGC ACGACCACAT TGTTTCCACC ATTTACTCAA     780
CATTTGGAGC TTTCTACATC CCACTGGCAT TGATTTTGAT CCTTTACTAC AAAATATATA     840
GAGCAGCAAA GACATTATAC CACAAGAGAC AAGCAAGTAG GATTGCAAAG GAGGAGGTGA     900
ATGGCCAAGT CCTTTTGGAG AGTGGTGAGA AAAGCACTAA ATCAGTTTCC ACATCCTATG     960
TACTAGAAAA GTCTTTATCT GACCCATCAA CAGACTTTGA TAAAATTCAT AGCACAGTGA    1020
GAAGTCTCAG GTCTGAATTC AAGCATGAGA AATCTTGGAG AAGGCAAAAG ATCTCAGGTA    1080
CAAGAGAACG GAAAGCAGCC ACTACCCTGG GATTAATCTT GGGTGCATTT GTAATATGTT    1140
GGCTTCCTTT TTTTGTAAAA GAATTAGTTG TTAATGTCTG TGACAAATGT AAAATTTCTG    1200
AAGAAATGTC CAATTTTTTG GCATGGCTTG GGTATCTCAA TTCCCTTATA AATCCACTGA    1260
TTTACACAAT CTTTAATGAA GACTTCAAGA AAGCATTCCA AAAGCTTGTG CGATGTCGAT    1320
GTTAGTTTTA AAAATGTTTA TTATTGAAGG ATGGGGGTTT TGAGGGGAG GAATAACTAG    1380
ATGAATGCCA ATAATAAAA CACTTAAGCT TTTAGAGGGA AATACATGAA AACTGCTAAA    1440
TTGATAAGGC TATAATTTAT ATTTTAATAG CAATGTGAAT ATAAAAGTTA TTGATCACCA    1500
CTATTCTAGG GTATTCAAAA TTAGAAAATA ATTTATGTAG GTTATAACAT ATTT          1554
```

(2) INFORMATION FOR SEQ ID NO:9:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO:9:

```
Met Asp Phe Leu Asn Ser Ser Asp Gln Asn Leu Thr Ser Glu Glu Leu
 1               5                  10                  15

Leu Asn Arg Met Pro Ser Lys Ile Leu Val Ser Leu Thr Leu Ser Gly
            20                  25                  30

Leu Ala Leu Met Thr Thr Thr Ile Asn Ser Leu Val Ile Ala Ala Ile
        35                  40                  45
```

```
Ile Val Thr Arg Lys Leu His His Pro Ala Asn Tyr Leu Ile Cys Ser
 50                  55                  60

Leu Ala Val Thr Asp Phe Leu Val Ala Val Leu Val Met Pro Phe Ser
 65                  70                  75                  80

Ile Val Tyr Ile Val Arg Glu Ser Trp Ile Met Gly Gln Val Val Cys
                 85                  90                  95

Asp Ile Trp Leu Ser Val Asp Ile Thr Cys Cys Thr Cys Ser Ile Leu
                100                 105                 110

His Leu Ser Ala Ile Ala Leu Asp Arg Tyr Arg Ala Ile Thr Asp Ala
            115                 120                 125

Val Glu Tyr Ala Arg Lys Arg Thr Pro Lys His Ala Gly Ile Met Ile
        130                 135                 140

Thr Ile Val Trp Ile Ile Ser Val Phe Ile Ser Met Pro Pro Leu Phe
145                 150                 155                 160

Trp Arg His Gln Gly Thr Ser Arg Asp Asp Glu Cys Ile Ile Lys His
                165                 170                 175

Asp His Ile Val Ser Thr Ile Tyr Ser Thr Phe Gly Ala Phe Tyr Ile
            180                 185                 190

Pro Leu Ala Leu Ile Leu Ile Leu Tyr Tyr Lys Ile Tyr Arg Ala Ala
        195                 200                 205

Lys Thr Leu Tyr His Lys Arg Gln Ala Ser Arg Ile Ala Lys Glu Glu
210                 215                 220

Val Asn Gly Gln Val Leu Leu Glu Ser Gly Glu Lys Ser Thr Lys Ser
225                 230                 235                 240

Val Ser Thr Ser Tyr Val Leu Glu Lys Ser Leu Ser Asp Pro Ser Thr
                245                 250                 255

Asp Phe Asp Lys Ile His Ser Thr Val Arg Ser Leu Arg Ser Glu Phe
            260                 265                 270

Lys His Glu Lys Ser Trp Arg Arg Gln Lys Ile Ser Gly Thr Arg Glu
        275                 280                 285

Arg Lys Ala Ala Thr Thr Leu Gly Leu Ile Leu Gly Ala Phe Val Ile
290                 295                 300

Cys Trp Leu Pro Phe Phe Val Lys Glu Leu Val Val Asn Val Cys Asp
305                 310                 315                 320

Lys Cys Lys Ile Ser Glu Glu Met Ser Asn Phe Leu Ala Trp Leu Gly
                325                 330                 335

Tyr Leu Asn Ser Leu Ile Asn Pro Leu Ile Tyr Thr Ile Phe Asn Glu
            340                 345                 350

Asp Phe Lys Lys Ala Phe Gln Lys Leu Val Arg Cys Arg Cys
        355                 360                 365

(2) INFORMATION FOR SEQ ID NO:10:

(i) SEQUENCE CHARACTERISTICS:
        (A) LENGTH: 2040 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

CTTTATTTTT TATTTAATTA TTTTTACTTA GGGCTTAAAA AATATCCACC AAAGAGGTTC      60

TTCACCAGTT CATCCCTGAC CCCGAGTCTT CTTGAAAAGC AAACGGCTCC CACCCGCTTG     120
```

```
TCATTTGCTA CAGTGTAGAG GCCAGGGGGT CTGCGGCAGG GCGAGCCCGG GCTGAGCTTT      180

CGCACGGTGC GCATCAGCCG GGCTGCCCAG CAGGGGAAGC CCGTCCCGGT GCGCGCCCGG      240

CGCTGGCGGC TGCCGGAGGC GGTGGCTGGG ACGCGGCGCG GCTGCCGCAG GGGAGCGGCG      300

GCGGCGGGCG CGAGGGGCGG GGCGCACTCC GCAACTTCGG CCGCGGCGGC CCGGCGCTCC      360

CGGCCCCGGC GCGCATCGCT GCGGGGCTGC GGTGCGGCCA ACCCGGCCAG GCTCGGCTCG      420

CCACCCTGCT CCTCTCGCGT GCCCGTCGGG GACCGCTGGT GCCTCCCGCG GGAGTCCTC      480

GCCCACGCGT CATCCGCAGA GGCTGGGGGA CCCTGGGACG TGCGGGGTCG CGAGGCCGAG      540

CCGGGCGCCC CCCAGTGGCC AGCCCCGGAC CCCATGGCTG GGCCGCGCGG AGCCGAGCGG      600

GCAAGGTGAA TCCAGCCCCG GGGCCGGCTG CCGGAGCGCT TGGCGGGGTC GCCGGCTCCA      660

TGGGCAGCGG CGCTCGGCAC GATGATGGAC GTTAACAGCA GCGGCCGCCC CGACCTCTAC      720

GGCCATCTCC GTTCACTCAT CCTGCCGGAG GTGGGGCGCG GGCTGCAGGA CCTGAGCCCC      780

GACGGTGGCG CCCACCCTGT GGTGAGCTCC TGGATGCCGC ACCTGCTGAG TGGCTTCCTA      840

GAGGTGACGC CTAGCCCGGC GCCCACCTGG GACGCGCCAC CGGACAATGT CTCAGGCTGC      900

GGGGAGCAGA TCAACTATGG CAGAGTGGAG AAAGTTGTGA TCGGCTCCAT CCTGACGCTC      960

ATCACGCTGC TGACGATCGC AGGCAACTGC CTGGTGGTA TCTCGGTGTG CTTCGTCAAG      1020

AAGCTCCGCC AGCCCTCCAA CTACCTGATT GTGTCCCTGG CGCTGGCTGA CCTCTCGGTG      1080

GCCGTGGCGG TCATGCCTTT CGTTAGTGTC ACCGACCTCA TCGGGGGCAA GTGGATCTTC      1140

GGCCACTTCT TCTGCAACGT CTTCATCGCC ATGGACGTCA TGTGCTGCAC GGCCTCGATC      1200

ATGACCCTGT GCGTGATCAG CATCGACAGG TACCTTGGGA TCACGAGACC CCTCACGTAC      1260

CCGGTGAGGC AAAATGGGAA ATGTATGGCC AAAATGATTC TGTCGGTCTG GCTGCTCTCT      1320

GCCTCCATCA CCTTACCTCC TCTCTTCGGA TGGGCTCAGA ATGTGAACGA TGACAAAGTG      1380

TGCTTGATCA GCCAGGATTT TGGCTACACG ATCTACTCCA CTGCGGTGGC GTTTTATATC      1440

CCCATGTCGG TCATGCTGTT CATGTACTAT CAGATTTACA AGGCCGCCAG GAAGAGTGCA      1500

GCCAAACACA AGTTCCCAGG CTTCCCACGC GTGCAGCCGG AGAGTGTCAT CTCCCTGAAT      1560

GGTGTGGTGA AGCTCCAGAA GGAGGTGGAA GAGTGTGCGA ACCTTTCGAG ACTGCTCAAA      1620

CACGAAAGGA AAAACATCTC CATCTTCAAG CGGGAACAGA AAGCAGCCAC TACCTTGGGG      1680

ATCATCGTGG GAGCCTTCAC TGTGTGCTGG CTGCCGTTTT TCCTCTTGTC CACAGCCCGC      1740

CCCTTTATCT GTGGCACCTC CTGTAGCTGC ATTCCTCTGT GGGTGGAGAG GACATGTCTG      1800

TGGCTGGGCT ATGCAAACTC TCTCATTAAT CCTTTTATAT ATGCCTTCTT CAACCGGGAC      1860

CTGAGGACCA CCTATCGTAG CCTACTCCAG TGCCAGTACC GGAATATCAA CCGGAAGCTC      1920

TCTGCTGCAG GCATGCATGA AGCCCTGAAA CTTGCTGAGA GGCCCGAGAG ATCCGAGTTT      1980

GTGCTGTAAG ACAAAACTCT GACCACTGTG GGAAAAAGGG TCATGATACA TGATCCAGAG      2040
```

(2) INFORMATION FOR SEQ ID NO:11:

(i) SEQUENCE CHARACTERISTICS:
        (A) LENGTH: 435 amino acids
        (B) TYPE: amino acid
        (D) TOPOLOGY: linear (ii) MOLECULE TYPE: protein (xi) SEQUENCE DESCRIPTION: SEQ ID NO:11:

```
Met Met Asp Val Asn Ser Ser Gly Arg Pro Asp Leu Tyr Gly His Leu
 1               5                  10                  15
```

```
Arg Ser Leu Ile Leu Pro Glu Val Gly Arg Gly Leu Gln Asp Leu Ser
             20                  25                  30

Pro Asp Gly Gly Ala His Pro Val Val Ser Ser Trp Met Pro His Leu
         35                  40                  45

Leu Ser Gly Phe Leu Glu Val Thr Ala Ser Pro Ala Pro Thr Trp Asp
 50                  55                  60

Ala Pro Pro Asp Asn Val Ser Gly Cys Gly Glu Gln Ile Asn Tyr Gly
 65                  70                  75                  80

Arg Val Glu Lys Val Val Ile Gly Ser Ile Leu Thr Leu Ile Thr Leu
             85                  90                  95

Leu Thr Ile Ala Gly Asn Cys Leu Val Val Ile Ser Val Cys Phe Val
            100                 105                 110

Lys Lys Leu Arg Gln Pro Ser Asn Tyr Leu Ile Val Ser Leu Ala Leu
            115                 120                 125

Ala Asp Leu Ser Val Ala Val Ala Val Met Pro Phe Val Ser Val Thr
        130                 135                 140

Asp Leu Ile Gly Gly Lys Trp Ile Phe Gly His Phe Phe Cys Asn Val
145                 150                 155                 160

Phe Ile Ala Met Asp Val Met Cys Cys Thr Ala Ser Ile Met Thr Leu
                165                 170                 175

Cys Val Ile Ser Ile Asp Arg Tyr Leu Gly Ile Thr Arg Pro Leu Thr
            180                 185                 190

Tyr Pro Val Arg Gln Asn Gly Lys Cys Met Ala Lys Met Ile Leu Ser
        195                 200                 205

Val Trp Leu Leu Ser Ala Ser Ile Thr Leu Pro Pro Leu Phe Gly Trp
    210                 215                 220

Ala Gln Asn Val Asn Asp Asp Lys Val Cys Leu Ile Ser Gln Asp Phe
225                 230                 235                 240

Gly Tyr Thr Ile Tyr Ser Thr Ala Val Ala Phe Tyr Ile Pro Met Ser
            245                 250                 255

Val Met Leu Phe Met Tyr Tyr Gln Ile Tyr Lys Ala Ala Arg Lys Ser
        260                 265                 270

Ala Ala Lys His Lys Phe Pro Gly Phe Pro Arg Val Gln Pro Glu Ser
    275                 280                 285

Val Ile Ser Leu Asn Gly Val Val Lys Leu Gln Lys Glu Val Glu Glu
    290                 295                 300

Cys Ala Asn Leu Ser Arg Leu Leu Lys His Glu Arg Lys Asn Ile Ser
305                 310                 315                 320

Ile Phe Lys Arg Glu Gln Lys Ala Ala Thr Thr Leu Gly Ile Ile Val
            325                 330                 335

Gly Ala Phe Thr Val Cys Trp Leu Pro Phe Phe Leu Leu Ser Thr Ala
        340                 345                 350

Arg Pro Phe Ile Cys Gly Thr Ser Cys Ser Cys Ile Pro Leu Trp Val
    355                 360                 365

Glu Arg Thr Cys Leu Trp Leu Gly Tyr Ala Asn Ser Leu Ile Asn Pro
370                 375                 380

Phe Ile Tyr Ala Phe Phe Asn Arg Asp Leu Arg Thr Thr Tyr Arg Ser
385                 390                 395                 400

Leu Leu Gln Cys Gln Tyr Arg Asn Ile Asn Arg Lys Leu Ser Ala Ala
            405                 410                 415

Gly Met His Glu Ala Leu Lys Leu Ala Glu Arg Pro Glu Arg Ser Glu
        420                 425                 430

Phe Val Leu
        435
```

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is either Ala or Ser"

(xi) SEQUENCE DESCRIPTION: SEQ ID NO:12:

Cys Ala Ile Xaa Leu Asp Arg Tyr
   1          5

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is either Cys or Met"

(ix) FEATURE:
        (A) NAME/KEY: Modified-site
        (B) LOCATION: 3
        (D) OTHER INFORMATION: /note= "Xaa is either Leu or Cys"

(xi) SEQUENCE DESCRIPTION: SEQ ID NO:13:

Xaa Trp Xaa Pro Phe Phe Ile
   1          5

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa is either Val or Gly"

(ix) FEATURE:
        (A) NAME/KEY: Modified-site
        (B) LOCATION: 5
        (D) OTHER INFORMATION: /note= "Xaa is either Phe or Tyr"

(xi) SEQUENCE DESCRIPTION: SEQ ID NO:14:

Phe Xaa Ala Phe Xaa Ile Pro Leu
   1          5

(2) INFORMATION FOR SEQ ID NO:15:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

AGCTCCGCGG AGCTCTATGY GCNATHGCNY TNGAYMGNTA                              40

(2) INFORMATION FOR SEQ ID NO:16:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

AGCTCCGCGG AGCTCTATGY GCNATHWSNY TNGAYMGNTA                              40

(2) INFORMATION FOR SEQ ID NO:17:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

AGCTCCGCGG AGCTCDATRA ARAANGGNAR CCARCA                                  36

(2) INFORMATION FOR SEQ ID NO:18:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

AGCTCCGCGG AGCTCDATRA ARAANGGRCA CCACAT                                  36

(2) INFORMATION FOR SEQ ID NO:19:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO -continued (iv) ANTI-SENSE: NO (xi) SEQUENCE DESCRIPTION: SEQ ID NO:19:

ACGTGCGGCC GCNARNGGDA TRWARAANGC NMCRAA                36

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

TCGGACCCCG ACGCGTGCAC CATC                              24

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:21:

GTGAATAACA CCACGTGCGT GCTC                              24

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:22:

AAGGAGGGGA GCTGCCTGCT TGCC                              24

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:23:

```
GGATCCCATG CTTCTGCCGG                                                          20
```

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:24:

```
GCACCGCGGA GCTCAAGCTT CCCCCCCCCC CCCCCCCCCC C                                  41
```

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:25:

```
TGCCCAAGTG AGCAGGATCA TCACG                                                    25
```

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:26:

```
TGGCGCGTTA TTGACCAGTA GCGGT                                                    25
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:27:

```
GGCTGGGTGG TGCAGCTTCC G                                                        21
```

(2) INFORMATION FOR SEQ ID NO:28:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:28:

CAGCTACGGC GGCCGCAAGC TTAAAATGGA TTTTCTAAAC TCA                              43

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:29:

CTGTTTGTAAT CGTGATGCCA GCATGC                                               26

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa is either Leu or Ile"

(ix) FEATURE:
        (A) NAME/KEY: Modified-site
        (B) LOCATION: 5
        (D) OTHER INFORMATION: /note= "Xaa is either Leu or Ser"

(ix) FEATURE:
        (A) NAME/KEY: Modified-site
        (B) LOCATION: 8
        (D) OTHER INFORMATION: /note= "Xaa is either Leu or Phe"

(xi) SEQUENCE DESCRIPTION: SEQ ID NO:30:

Trp Xaa Gly Tyr Xaa Asn Ser Xaa
    1               5

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:31:

GCTCATCTAG ANARNSWRTT NVDRTANCCN ADCCA                                            35

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:32:

Phe Val Tyr Trp Lys Ile Tyr Lys
    1               5

(2) INFORMATION FOR SEQ ID NO:33:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

CTGGTGGTCG ACGGTACCTT YGTNTAYTGG AARATHAYAA                                       40

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

CCTCAGGAGT CTGAGACGGT ATTC                                                       24

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

GCTGTGGAGG TGAAGGACGT TCAC                                                       24

(2) INFORMATION FOR SEQ ID NO:36:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (xi) SEQUENCE DESCRIPTION: SEQ ID NO:36:

Met Ile Lys Glu Glu Leu Asn Gly Gln Val Leu Leu Glu Ser Gly Glu
       1               5                   10                  15

Lys (2) INFORMATION FOR SEQ ID NO:37:

(i) SEQUENCE CHARACTERISTICS:
            (A) LENGTH: 18 amino acids
            (B) TYPE: amino acid
            (D) TOPOLOGY: linear (ii) MOLECULE TYPE: peptide (xi) SEQUENCE DESCRIPTION: SEQ ID NO:37:

His Ser Thr Val Lys Ser Pro Arg Ser Glu Leu Lys His Glu Lys Ser
       1               5                   10                  15

Trp Arg (2) INFORMATION FOR SEQ ID NO:38:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:38:

Trp Thr Ile Thr Arg His Leu Gln Tyr Thr Leu Arg Thr Arg Arg Arg
       1               5                   10                  15

(2) INFORMATION FOR SEQ ID NO:39:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (xi) SEQUENCE DESCRIPTION: SEQ ID NO:39:

Val Val Pro Leu Pro Ala Thr Thr Gln Ala Lys Glu Ala Pro Gln Glu
       1               5                   10                  15

Ser Glu Thr Val
                   20

(2) INFORMATION FOR SEQ ID NO:40:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (xi) SEQUENCE DESCRIPTION: SEQ ID NO:40:

Arg Ala Thr Val Ala Phe Gln Thr Ser Gly Asp Ser Trp Arg Glu Gln
       1               5                   10                  15

```
        Lys Glu Lys Arg
                    20

(2) INFORMATION FOR SEQ ID NO:41:

(i) SEQUENCE CHARACTERISTICS:
         (A) LENGTH: 15 amino acids
         (B) TYPE: amino acid
         (D) TOPOLOGY: linear (ii) MOLECULE TYPE: peptide (xi) SEQUENCE DESCRIPTION: SEQ ID NO:41:

Lys Asn Tyr Asn Asn Ala Phe Lys Ser Leu Phe Thr Lys Gln Arg
    1               5                   10                  15

(2) INFORMATION FOR SEQ ID NO:42:

(i) SEQUENCE CHARACTERISTICS:
         (A) LENGTH: 19 amino acids
         (B) TYPE: amino acid
         (D) TOPOLOGY: linear (ii) MOLECULE TYPE: peptide (xi) SEQUENCE DESCRIPTION: SEQ ID NO:42:

Val Ser Pro Ile Pro Glu Ala Val Glu Val Lys Asp Ala Ser Gln His
    1               5                   10                  15

Pro Gln Met (2) INFORMATION FOR SEQ ID NO:43:

(i) SEQUENCE CHARACTERISTICS:
         (A) LENGTH: 15 amino acids
         (B) TYPE: amino acid
         (D) TOPOLOGY: linear (ii) MOLECULE TYPE: peptide (xi) SEQUENCE DESCRIPTION: SEQ ID NO:43:

Arg Ser Tyr Ser Ser Ala Phe Lys Val Phe Phe Ser Lys Gln Gln
    1               5                   10                  15

(2) INFORMATION FOR SEQ ID NO:44:

(i) SEQUENCE CHARACTERISTICS:
         (A) LENGTH: 19 amino acids
         (B) TYPE: amino acid
         (D) TOPOLOGY: linear (ii) MOLECULE TYPE: peptide (xi) SEQUENCE DESCRIPTION: SEQ ID NO:44:

Arg Lys Ser Ala Ala Lys His Lys Phe Pro Gly Phe Pro Arg Val Gln
    1               5                   10                  15

Pro Glu Ser (2) INFORMATION FOR SEQ ID NO:45:

(i) SEQUENCE CHARACTERISTICS:
         (A) LENGTH: 21 amino acids
         (B) TYPE: amino acid
         (D) TOPOLOGY: linear (ii) MOLECULE TYPE: peptide (xi) SEQUENCE DESCRIPTION: SEQ ID NO:45:
```

```
       Pro Glu Val Gly Arg Gly Leu Gln Asp Leu Ser Pro Asp Gly Ala
       1               5                   10                  15

His Pro Val Val Ser
                       20
```

(2) INFORMATION FOR SEQ ID NO:46:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:46:

```
       Ser Arg Leu Leu Lys His Glu Arg Lys Asn Ile Ser Ile Phe Lys Arg
       1               5                   10                  15

Glu Gln Lys
```

(2) INFORMATION FOR SEQ ID NO:47:

(i) SEQUENCE CHARACTERISTICS:
        (A) LENGTH: 52 amino acids
        (B) TYPE: amino acid
        (D) TOPOLOGY: linear (ii) MOLECULE TYPE: peptide (xi) SEQUENCE DESCRIPTION: SEQ ID NO:47:

```
       Met Glu Val Cys Asn Leu Ser Gly Ala Thr Pro Gly Ile Ala Phe Pro
       1               5                   10                  15

Pro Gly Pro Glu Ser Cys Ser Asp Ser Pro Ser Ser Gly Arg Ser Met
                       20                  25                  30

Gly Ser Thr Pro Gly Gly Leu Ile Leu Ser Gly Arg Glu Pro Pro Phe
                       35                  40                  45

Ser Ala Phe Thr
                   50
```

(2) INFORMATION FOR SEQ ID NO:48:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:48:

```
       Pro Leu Ser Leu Val Ser Glu Leu Ser Ala Gly Arg Arg Trp Gln Leu
       1               5                   10                  15

Gly Arg Ser Leu Cys His Val Trp Ile Ser Phe Asp
                       20                  25
```

(2) INFORMATION FOR SEQ ID NO:49:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:49:

```
       Ala Pro Leu Leu Phe Gly Trp Gly Glu Ala Tyr Asp Ala Arg Leu Gln
       1               5                   10                  15
```

```
    Arg Cys Gln Val Ser Gln Glu Pro Ser Tyr Ala Val Phe Ser Thr Cys
                 20                  25                  30

Gly (2) INFORMATION FOR SEQ ID NO:50:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:50:

Trp Ile Pro Phe Phe Leu Thr Glu Leu Val Ser Pro Leu Cys Ala Cys
    1               5                   10                  15

Ser Leu Pro Pro Ile Trp Lys Ser Ile Phe Leu Trp Leu Gly
                 20                  25                  30

(2) INFORMATION FOR SEQ ID NO:51:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:51:

Lys Asn Tyr Asn Asn Ala Phe Lys Ser Leu Phe Thr Lys Gln Arg
    1               5                   10                  15

(2) INFORMATION FOR SEQ ID NO:52:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:52:

Met Asp Leu Pro Ile Asn Leu Thr Ser Phe Ser Leu Ser Thr Pro Ser
    1               5                   10                  15

Thr Leu Glu Pro Asn Arg Ser Leu Asp Thr Glu Ala Leu Arg Thr Ser
                 20                  25                  30

Gln Ser Phe Leu Ser Ala Phe Arg
                 35                  40

(2) INFORMATION FOR SEQ ID NO:53:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:53:

Pro Leu Ser Leu Val His Glu Leu Ser Gly Arg Arg Trp Gln Leu Gly
    1               5                   10                  15

Arg Arg Leu Cys Gln Leu Trp Ile Ala Leu
                 20                  25

(2) INFORMATION FOR SEQ ID NO:54:
```

(i) SEQUENCE CHARACTERISTICS:
    (A) LENGTH: 33 amino acids
    (B) TYPE: amino acid
    (D) TOPOLOGY: linear (ii) MOLECULE TYPE: peptide (xi) SEQUENCE DESCRIPTION: SEQ ID NO:54:

Ala Pro Leu Leu Phe Gly Trp Gly Glu Thr Tyr Ser Glu Leu Ser Glu
1               5                   10                  15

Glu Cys Gln Val Ser Arg Glu Pro Ser Tyr Thr Val Phe Ser Thr Val
            20                  25                  30

Gly (2) INFORMATION FOR SEQ ID NO:55:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:55:

Val Thr Glu Leu Ile Ser Pro Leu Cys Ser Trp Asp Ile Pro Ala Leu
    1               5                   10                  15

Trp Lys Ser Ile Phe Leu Trp
                20

(2) INFORMATION FOR SEQ ID NO:56:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:56:

Arg Ser Tyr Ser Ser Ala Phe Lys Val Phe Ser Lys Gln Gln
    1               5                   10                  15

(2) INFORMATION FOR SEQ ID NO:57:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:57:

Met Asp Phe Leu Asn Ser Ser Asp Gln Asn Leu Thr Ser Glu Glu Leu
    1               5                   10                  15

Leu Asn Arg Met Pro Ser Lys
                20

(2) INFORMATION FOR SEQ ID NO:58:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:58:

```
Met Pro Phe Ser Ile Val Tyr Ile Val Arg Glu Ser Trp Ile Met Gly
1               5                   10                  15

Gln Gly Leu Cys Asp Leu Trp Leu Ser Val Asp
            20                  25
```

(2) INFORMATION FOR SEQ ID NO:59:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:59:

```
Phe Ile Ser Met Pro Leu Phe Trp Arg His Gln Gly Asn Ser Arg
1               5                   10                  15

Asp Asp Gln Cys Ile Ile Lys His Asp His Ile Val Ser Thr Ile Tyr
                20                  25                  30

Ser Thr Phe Gly
            35
```

(2) INFORMATION FOR SEQ ID NO:60:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:60:

```
Trp Leu Pro Phe Phe Val Lys Glu Leu Val Val Asn Ile Cys Glu Lys
1               5                   10                  15

Cys Lys Ile Ser Glu Glu Met Ser Asn Phe
                20                  25
```

(2) INFORMATION FOR SEQ ID NO:61:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:61:

```
Tyr Thr Ile Phe Asn Glu Asp Phe Lys Lys Ala Phe Gln Lys Leu Val
1               5                   10                  15

Arg Cys Arg Asn
            20
```

(2) INFORMATION FOR SEQ ID NO:62:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:62:

```
Met Asp Phe Leu Asn Ser Ser Asp Gln Asn Leu Thr Ser Glu Glu Leu
1               5                   10                  15

Leu Asn Arg Met Pro Ser Lys
            20
```

(2) INFORMATION FOR SEQ ID NO:63:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:63:

```
Met Pro Phe Ser Ile Val Tyr Ile Val Arg Glu Ser Trp Ile Met Gly
1               5                  10                  15

Gln Val Val Cys Asp Ile Trp Leu Ser Val Asp
            20                  25
```

(2) INFORMATION FOR SEQ ID NO:64:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:64:

```
Phe Ile Ser Val Pro Pro Leu Phe Trp Arg His Gln Gly Thr Ser Asp
1               5                  10                  15

Asp Glu Cys Ile Ile Lys His Asp His Ile Val Ser Thr Ile Tyr Ser
            20                  25                  30

Thr Phe Gly
        35
```

(2) INFORMATION FOR SEQ ID NO:65:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:65:

```
Trp Leu Pro Phe Phe Val Lys Glu Leu Val Val Asn Val Cys Asp Lys
1               5                  10                  15

Cys Lys Ile Ser Glu Glu Met Ser Asn Phe
            20                  25
```

(2) INFORMATION FOR SEQ ID NO:66:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:66:

```
Tyr Thr Ile Phe Asn Glu Asp Phe Lys Lys Ala Phe Gln Lys Leu Val
1               5                  10                  15

Arg Cys Arg Cys
        20
```

(2) INFORMATION FOR SEQ ID NO:67:

(i) SEQUENCE CHARACTERISTICS:

(A) LENGTH: 84 amino acids
        (B) TYPE: amino acid
        (D) TOPOLOGY: linear (ii) MOLECULE TYPE: peptide (xi) SEQUENCE DESCRIPTION: SEQ ID NO:67:

Met Met Asp Val Asn Ser Ser Gly Arg Pro Asp Leu Tyr Gly His Leu
    1               5                   10                  15

Arg Ser Leu Ile Leu Pro Glu Val Gly Arg Gly Leu Gln Asp Leu Ser
                    20                  25                  30

Pro Asp Gly Gly Ala His Pro Val Val Ser Ser Trp Met Pro His Leu
                35                  40                  45

Leu Ser Gly Phe Leu Glu Val Thr Ala Ser Pro Ala Pro Thr Trp Asp
    50                  55                  60

Ala Pro Pro Asp Asn Val Ser Gly Cys Gly Glu Gln Ile Asn Tyr Gly
    65                  70                  75                  80

Arg Val Glu Lys (2) INFORMATION FOR SEQ ID NO:68:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Region
        (B) LOCATION: (7^8)
        (D) OTHER INFORMATION: /note= "An unspecified amino acid
            residue is present in this location"

(xi) SEQUENCE DESCRIPTION: SEQ ID NO:68:

Met Pro Phe Val Ser Val Thr Leu Ile Gly Gly Lys Trp Ile Phe Gly
    1               5                   10                  15

His Phe Phe Cys Asn Val Phe Ile Ala Met Asp Val Met Cys Cys
                    20                  25                  30

(2) INFORMATION FOR SEQ ID NO:69:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (ix) FEATURE:
        (A) NAME/KEY: Region
        (B) LOCATION: (11^12)
        (D) OTHER INFORMATION: /note= "An unspecified amino acid
            residue is present in this location"

(xi) SEQUENCE DESCRIPTION: SEQ ID NO:69:

Thr Leu Pro Pro Leu Phe Gly Trp Ala Gln Asn Asn Asp Asp Lys Val
    1               5                   10                  15

Cys Leu Ile Ser Gln Asp Phe Gly Val Thr Ile Tyr Ser Thr Ala Val
                    20                  25                  30

Ala Phe (2) INFORMATION FOR SEQ ID NO:70:

(i) SEQUENCE CHARACTERISTICS:
        (A) LENGTH: 36 amino acids (B) TYPE: amino acid
            (D) TOPOLOGY: linear (ii) MOLECULE TYPE: peptide (xi) SEQUENCE DESCRIPTION: SEQ ID NO:70:

Phe Thr Val Cys Trp Leu Pro Phe Phe Leu Leu Ser Thr Ala Arg Pro
    1               5                   10                  15

Phe Ile Cys Gly Thr Ser Cys Ser Cys Ile Pro Leu Trp Val Glu Arg
                20                  25                  30

Thr Cys Leu Trp
            35

(2) INFORMATION FOR SEQ ID NO:71:

(i) SEQUENCE CHARACTERISTICS:
            (A) LENGTH: 47 amino acids
            (B) TYPE: amino acid
            (D) TOPOLOGY: linear (ii) MOLECULE TYPE: peptide (xi) SEQUENCE DESCRIPTION: SEQ ID NO:71:

Phe Phe Asn Arg Asp Leu Arg Thr Thr Tyr Arg Ser Leu Leu Gln Cys
    1               5                   10                  15

Gln Tyr Arg Asn Ile Asn Arg Lys Leu Ser Ala Ala Gly Met His Glu
                20                  25                  30

Ala Leu Lys Leu Ala Glu Arg Pro Glu Arg Ser Glu Phe Val Leu
            35                  40                  45

(2) INFORMATION FOR SEQ ID NO:72:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:72:

CAAGCAAGTA GGATTGCAAA G                                              21

(2) INFORMATION FOR SEQ ID NO:73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:73:

CACAAGCTTT TGGAATGCTT T                                              21

DNA ENCODING SEROTONIN RECEPTORS

STATEMENT OF GOVERNMENT SUPPORT

This invention was made with government support under Grant #F49620-92-J-0188 awarded by the Air Force Office of Scientific Research and Grant #GM 32355 and #NS 22347 awarded by the National Institutes of Health. The government has certain rights in the invention.

TECHNICAL FIELD

The present invention relates generally to the field of serotonin receptors. Specifically, the invention relates to isolated nucleic acid molecules encoding serotonin receptors, to isolated receptor proteins, and to uses of the nucleic acid molecules and proteins in methods for determining ligand binding, detecting expression of serotonin receptors, drug screening and therapeutic treatments involving human serotonin receptors.

BACKGROUND

Serotonin (5-hydroxytryptamine, 5-HT) regulates a wide variety of sensory, motor and behavioral functions in the mammalian central nervous system (CNS). This biogenic amine neurotransmitter is synthesized by neurons in the raphe nuclei of the brain stem that project throughout the CNS, with highest density in basal ganglia and limbic structures. Steinbusch, *Handbook of Chemical Neuroanatomy*, 3:68–125, Bjorklund et al., eds., Elsevier Science Publishers, B. V., (1984). Serotonergic transmission is thought to be involved with a variety of behaviors and psychiatric disorders including anxiety, sleep regulation, aggression, feeding and depression. Cowen, British J. Psych., 159:7–14 (1991); and Lucki, *Neurosci. & Biobehav. Rev.*, 16:83–93 (1992). Understanding how 5-HT mediates its diverse physiological actions requires the identification and isolation of the pertinent 5-HT receptors.

Molecular cloning has indicated that 5-HT receptors belong to at least two protein superfamilies: G-protein-associated receptors which have seven putative transmembrane domains (TMDs) ($5\text{-HT}_{1A/B/C/D/E}$, $5\text{-HT}_2$ and rat stomach fundus) and ligandgated ion channel receptors which have four putative TMDs ($5\text{-HT}_3$). Albert et al., *J. Biol. Chem.*, 265:5825–5832 (1990); Hamblin et al., *Biochem. & Biophys. Res. Comm.*, 184:752–759 (1992); Adham et al., *Molec. Pharm.*, 41:1–7 (1992); Voigt et al., *EMBO J.*, 10:4017–4023 (1991); Jin, et al., *J. Biol. Chem.*, 267:5735–5738 (1992); Maroteaux, et al., *Proc. Natl. Acad. Sci. USA*, 89:3020–3024 (1992); Julius, et al., *Science*, 241:558–564 (1988); Lubbert, et al., *Proc. Nat. Acad. Sci. USA*, 84:4332–4336 (1987); Hamblin, et al., *Mole. Pharm.*, 40:143–148 (1991); Zgombick, et al., *Mole. Pharm.*, 40:1036–1042 (1991); Weinshank, et al., *Proc. Natl. Acad. Sci. USA*, 89:3630–3634 (1992); Levy, et al.,*J. Biol. Chem.*, 267:7553–7562 (1992); McAllister, et al., *Proc. Natl. Acad. Sci. USA*, 89:5517–5521 (1992); Pritchett, et al., *EMBO J.*, 7:4135–4140 (1988); Foguet, et al., *EMBO J.*, 11:3481–3487 (1992); and Maricq, et al., *Science*, 254:432–437 (1991).

As a serotonin receptor cloning strategy, Libert et al., *Science*, 244:569–572 (1989), demonstrated that novel G-protein-associated receptors could be identified in a polymerase chain reaction (PCR) using degenerate primers corresponding to strongly conserved sequences within their TMDs.

The subtypes of serotonin receptors have been historically distinguished on the basis of their pharmacological binding profiles, on second messenger coupling, and based on physiological roles known for the better characterized serotonin receptors. Most of the characterizing data in the field is not based on the properties of a single purified receptor protein or gene, but rather based on experimental observations using a model tissue. Thus, there is a need for extensive molecular and corresponding pharmacological characterization of serotonin receptors in order to better understand the extent of the subfamilies and the physiological roles each plays.

BRIEF DESCRIPTION OF THE INVENTION

The invention relates to the discovery, cloning and characterization of several unique serotonin receptors.

Thus, in one embodiment, the invention describes a isolated protein that is a serotonin receptor selected from the group consisting of $5\text{-HT}_{1E\text{-}Like}$, $5\text{-HT}_{5\alpha}$, $5\text{-HT}_{5\beta}$ and $5\text{-HT}_6$.

The invention also describes a DNA segment encoding a serotonin receptor selected from the group consisting of $5\text{-HT}_{1E\text{-}Like}$, $5\text{-HT}_{5\alpha}$, $5\text{-HT}_{5\beta}$ and $5\text{-HT}_6$, vectors containing the DNA segments capable of expressing the serotonin receptor, and mammalian cells that contain the vectors and express the serotonin receptors.

Also described is a method for determining whether a ligand can bind to a preselected serotonin receptor which comprises;

(a) contacting a mammalian cell with a candidate ligand under conditions permitting binding of a known serotonin receptor ligand to the serotonin receptor, wherein the mammalian cell comprises a vector adapted for expressing a serotonin receptor in the mammalian cell, wherein the said comprises a DNA segment encoding the preselected serotonin receptor and expresses cell surface serotonin receptor; and (b) detecting the presence of any of the candidate ligand bound to the cell surface serotonin receptor, and thereby determining whether the ligand binds to the receptor.

In a related embodiment, the invention describes a method for screening drugs to identify a candidate drug that can activate a preselected serotonin receptor which comprises;

(a) contacting a mammalian cell with the candidate drug under conditions permitting activation of the serotonin receptor by a known serotonin receptor activating drug, the mammalian cell comprising a vector adapted for expressing a serotonin receptor in the mammalian cell, the vector comprising a DNA segment encoding the preselected serotonin receptor, and the mammalian containing a cell surface serotonin receptor; and (b) detecting the activation status of the cell surface serotonin receptor, and thereby determining whether the drug activates the receptor.

The invention also describes an isolated nucleic acid molecule probe comprising a nucleic acid segment of at least 10 nucleotides in length having a sequence corresponding to or complementary to a sequence included within the coding region of a nucleotide sequence that encodes a serotonin receptor selected from the group consisting of $5\text{-HT}_{1E\text{-}Like}$, $5\text{-HT}_{5\alpha}$, $5\text{-HT}_{5\beta}$ and $5\text{-HT}_6$. The probe is useful in a variety of diagnostic systems for detecting serotonin receptor genes and mRNA transcripts in vitro and in situ.

A therapeutic oligonucleotide of about 10 to 100 nucleotides in length is also described having a sequence capable of hybridizing specifically with a structural protein region of the nucleotide sequence that encodes a serotonin receptor of this invention, as are therapeutic methods for altering serotonin receptor gene expression in a cell comprising administering to a subject an amount of a pharmaceutical composition comprising a physiologically acceptable carrier and the therapeutic oligonucleotide.

Still further, the invention describes a serotonin receptor polypeptide having a length of no more than about 100 amino acid residues and a sequence that substantially corresponds to a portion of the sequence of a serotonin receptor of this invention.

Also described is an antibody comprising antibody molecules that immunoreact with a serotonin receptor of this invention, including a monoclonal antibody.

A transgenic nonhuman mammal is also described expressing a DNA segment that encodes a human serotonin receptor of this invention, and screening methods using the transgenic mammal.

Other embodiments will be apparent to one skilled in the art.

BRIEF DESCRIPTION OF THE DRAWINGS

In the figures forming a portion of this disclosure:

FIG. 1 illustrates the nucleotide sequence and predicted amino acid sequence of the rat MR22 cDNA clone as described in Example 4. The putative transmembrane domains are underlined, a putative N-glycosylation site is circled and putative protein kinase C phosphorylation sites are boxed.

FIG. 2 illustrates the nucleotide sequence and predicted amino acid sequence of the rat REC17 cDNA clone as described in Example 4. The putative transmembrane domains are underlined, two putative N-glycosylation sites are circled and putative protein kinase C phosphorylation sites are boxed.

FIG. 3 illustrates the nucleotide sequence and predicted amino acid sequence of the rat MR77 genomic clone as described in Example 4. The putative transmembrane domains are underlined. Arrows indicate potential N-linked glycosylation sites. The asterisk is located above the intron splice junction. The sequence upstream of this site in Bold print represents the MR77 cDNA sequence which is different from the genomic clone. The cDNA sequence downstream from the asterisk is identical to the genomic clone (not shown). Circled and squared amino acids are consensus phosphorylation sites for protein kinase C and calmodulin kinase II, respectively. Amino acids in italics beneath the rat amino acid sequence represent differences with human clone. The nucleotide sequences of the rat and human clones can be accessed from GenBank, accession numbers are L05596 and L05597, respectively.

FIG. 4 illustrates the PCR-based detection of MR77 mRNA expression described in Example 4.

FIG. 5 illustrates the nucleotide and predicted amino acid sequence of the rat REC20 cDNA clone as described in Example 4. The amino acid translation was determined for the longest open reading frame which begins with a methionine. The region surrounding the codon ATG for translation initiation conforms with the consensus sequence described by Kozak, *Nuc. Acids Res.*, 12:857–872 (1984). The putative transmembrane spanning regions are underlined and numbered (I-VII). Potential sites for N-linked glycosylation and protein kinase C phosphorylation are marked beneath the amino acid by solid circles and squares, respectively.

DETAILED DESCRIPTION OF THE INVENTION

A. Definitions

Figure 4A:
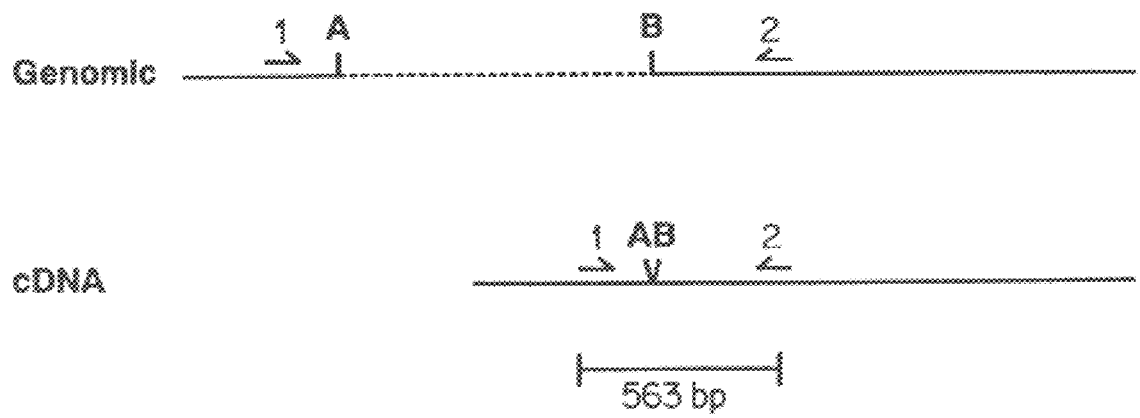
In FIG. 4A, point B corresponds to nucleotide 97 of the MR77 genomic clone shown in FIG. 3. The distance between, and including, oligonucleotides 1 and 2 is 563 base pairs on the cDNA clone. The distance between point A and B on the genomic clone is not known.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) molecule: a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors".

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the noncoding strand of the DNA or 5'- to 3'-direction along the RNA transcript.

Reading Frame: Particular sequence of contiguous nucleotide triplets (codons) employed in translation that define the structural protein encoding-portion of a gene, or structural gene. The reading frame depends on the location of the translation initiation codon.

B. Serotonin Receptor Proteins

The serotonin receptors are known in the art as a family of mammalian proteins that function as receptors for a variety of bioactive molecules which generally fall into the category of serotonin analogs. Based on the background review of the art, it is seen that there are many different serotonin receptors, which differ in amino acid residue sequence, tissue location, and function based on their ligand specificity.

The present invention provides the description of four new serotonin receptors, represented herein by the four prototype receptors MR77, MR22, REC17 and REC20, and that fall into three new serotonin subfamily classifications, 5-HT$_{1E-Like}$, 5-HT$_5$, and 5-HT$_6$. The MR77 serotonin receptor is the prototype receptor for the 5-HT$_{1E-Like}$ subfamily. The MR22 and REC17 serotonin receptors are prototype receptors for the 5-HT$_5$ subfamily, and can be further subdivided in to two subfamily types, 5-HT$_{5\alpha}$ and 5-HT$_{5\beta}$, for REC17 and MR22, respectively. The REC20 serotonin receptor is the prototype receptor for the 5-HT$_6$ subfamily.

The characterization of a serotonin receptor as a member of a serotonin receptor subfamily is based herein on the amino acid residue sequence homology of the receptor protein compared to other serotonin receptor amino acid sequences. Thus, a protein is considered to be a serotonin receptor of this invention if the protein has a total amino acid residue sequence homology of at least 60% with a prototype sequence, and is furthermore cosidered to be a member of that prototype's subfamily.

Variations are known in isolates of serotonin receptors, and such variations are not to be construed as limiting. For example, allelic variation within a mammalian species can tolerate a several percent difference between isolates of a type of serotonin receptor, which differences comprise non-deleterious variant amino acid residues. Thus a protein of about 95% homology, and preferably at least 98% homology, to a disclosed serotonin receptor is considered to be an allelic variant of the disclosed serotonin receptor, and therefore is considered to be a serotonin receptor of this invention.

In addition, "type" variants of a serotonin receptor are members of a subfamily exhibiting about 60% to 95% homology to each other, and more typically exhibiting about 60–80% homology. As an example, the REC17 and MR22 serotonin receptor proteins of this invention are shown herein to have approximately 68% sequence homology to one another, thereby belonging to the same subfamily, and yet are designated as different serotonin receptor types. A serotonin receptor is considered to be of the same "type" as a disclosed serotonin receptor if it has at least about 60% homology, and preferably 60–95% homology, to a disclosed serotonin receptor.

A serotonin receptor of this invention can be in a variety of forms, depending upon the use therefor, as described herein. For example, a serotonin receptor can be isolated from a natural tissue and be present in a composition in an isolated form, ie., comprising at least about 0.1 percent by weight of the total composition, preferably at least 1%, and more preferably at least about 90%. Particularly preferred is a substantially pure preparation of receptor, that is at least 90% by weight, and more preferably at least 99% by weight.

Alternatively, a serotonin receptor of this invention can be recombinant protein, that is, produced by recombinant DNA (rDNA) methods as described herein. A recombinant serotonin receptor need not necessarily be substantially pure, or even isolated, to be useful in certain embodiments, although recombinant production methods are a preferred means to produce a source for further purification to yield an isolated or substantially pure receptor composition. A recombinant serotonin receptor can be present in or on a mammalian cell line or in crude extracts of a mammalian cell line.

In one embodiment, a serotonin receptor is substantially free of serotonin receptors from other serotonin subfamilies, so that the purity of a receptor reagent and freedom from pharmacologically distinct receptors affords use in the screening methods. The recombinant production methods are ideally suited to produce absolute purity in this regard, although biochemical purification methods from natural sources are also contemplated. In this regard, a serotonin receptor is substantially free from other serotonin receptors if there are insufficient other receptors such that pharmacological cross-reactivity is not detected in conventional screening assays for ligand binding.

An isolated or recombinant serotonin receptor of this invention can be used for a variety of purposes, as described further herein. The receptor can be used as an immunogen to produce antibodies immunoreactive with a serotonin receptor. The receptor can be used in in vitro ligand binding assays for identifying ligand binding specificities, and to characterize candidate pharmaceutical compounds useful for modulating serotonin receptor function. Other uses will be readily apparent to one skilled in the art.

Furthermore, the invention contemplates analogs of a serotonin receptor of this invention. An analog is a man-made variant which exhibits the qualities of a serotonin receptor of this invention in terms of immunological reactivity, ligand binding capacity and the like functional properties of a serotonin receptor of this invention. An analog can therefore be a cleavage product of a serotonin receptor, can be a polypeptide corresponding to a portion of a serotonin receptor, and can be serotonin receptor polypeptide in which a membrane anchor has been removed, to name a few permutations.

Insofar as the present disclosure identifies serotonin receptors from different mammalian species, the present invention is not to be limited to a serotonin receptor derived from one or a few mammalian species. Thus, the invention contemplates a mammalian serotonin receptor of this invention, which receptor can be derived, by rDNA or biochemical purification from natural sources, from any of a variety of species including man, mouse, rabbit, rat, dog, cat, sheep, cow, and the like mammalian species, without limitation. Human and agriculturally relevant animal species are particularly preferred.

1. Serotonin Receptor Subfamily $5\text{-HT}_{1E\text{-}Like}$

In one embodiment, a $5\text{-HT}_{1E\text{-}Like}$ serotonin receptor in its various embodiments is contemplated. The prototype receptors of this subfamily are MR77 derived from rat hypothalamus or a human genomic library, as described herein. The amino acid residue sequence of human MR77 is shown in SEQ ID NO 9. The amino acid residue sequence of rat MR77 is shown in SEQ ID NO 7.

2. Serotonin Receptor Subfamily $5\text{-HT}_5$

In another embodiment, a $5\text{-HT}_5$ serotonin receptor in its various embodiments is contemplated. The prototype receptors of this subfamily are REC17 and MR22 derived from rat hypothalamus, as described herein, which represent two receptor types in this subfamily. The amino acid residue sequence of rat REC17 is shown in SEQ ID NO 4. The amino acid residue sequence of rat MR22 is shown in SEQ ID NO 2.

3. Serotonin Receptor Subfamily $5\text{-HT}_6$

In another embodiment, a $5\text{-HT}_6$ serotonin receptor in its various embodiments is contemplated. The prototype receptor of this subfamily is REC20 derived from rat hypothalamus, as described herein. The amino acid residue sequence of rat REC20 is shown in SEQ ID NO 11. A serotonin receptor of this invention can be prepared by a variety of means, although expression in a mammalian cell using a rDNA expression vector is preferred. Exemplary production methods for a recombinant serotonin receptor are described in the Examples, and include the production of MR77, REC17, MR22 and REC20.

Thus, the invention also provides a method for the production of isolated serotonin receptor comprising inducing cells to express a serotonin receptor of this invention, recovering the receptor from the resulting cells, and purifying the receptor so recovered by biochemical fractionation methods, using a specific antibody of this invention, or other chemical procedures. The inducing step can comprise inserting a rDNA vector encoding a serotonin receptor of this invention, which rDNA is capable of expressing the receptor, into a suitable host cell, and expressing the vector's serotonin receptor gene.

C. Nucleic Acid Molecules

The amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms.

Occasionally, a methylated variant of a purine or pyrimidine may be incorporated into a given nucleotide sequence. However, such methylations do not affect the coding relationship in any way.

A nucleic acid molecule is any polynucleotide, whether it be a polyribonucleotide of polydeoxyribonucleotide, ie., RNA or DNA, or analogs thereof. In preferred embodiments, a nucleic acid molecule is in the form of a segment of duplex DNA, although for certain molecular biological methodologies, single-stranded DNA or RNA is preferred.

The DNA segments of the present invention are characterized as including a DNA sequence that encodes a serotonin receptor of this invention. That is, the DNA segments of the present invention are characterized by the presence of a serotonin receptor structural gene. Preferably the gene is present as an uninterrupted linear series of codons where each codon codes for an amino acid residue found in the serotonin receptor protein, i.e., a gene free of introns.

One preferred embodiment is a DNA segment that codes an amino acid residue sequence that defines a serotonin receptor protein corresponding in sequence one of the serotonin receptors MR77, REC17, MR22 or REC20, and the DNA segment is capable of expressing the serotonin receptor. A preferred DNA segment codes for an amino acid residue sequence substantially the same as, and preferably consisting essentially of, the sequence shown in the sequence listing SEQ ID NOs 2, 4, 7, 9 or 11. Particularly preferred DNA segments have a sequence shown in SEQ ID NOs 1, 3, 5, 8 or 10. Representative and preferred DNA segments are described in the Examples.

Homologous DNA and RNA sequences that encode the above serotonin receptors are also contemplated.

DNA segments (i.e., synthetic oligonucleotides) that encode serotonin receptor proteins can easily be synthesized by chemical techniques, for example, the phosphotriester method of Matteucci, et al., (J. Am. Chem. Soc., 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

Furthermore, DNA segments consisting essentially of structural genes encoding a serotonin protein can be obtained from recombinant DNA molecules containing a gene that defines a serotonin receptor of this invention, and can be subsequently modified, as by site directed mutagenesis, to introduce any desired substitutions.

1. Cloning Serotonin Receptors

Serotonin receptors of this invention can be cloned by a variety of cloning methods and from any mammalian species. The cloning is based on the observation that there is a significant degree of homology between mammalian species for any given serotonin receptor of this invention, and therefor can be carried according to the general methods described in the Examples, using nucleic acid homology strategies.

A typical degree of homology required to successfully clone a serotonin receptor of the same subfamily from a different species as is disclosed herein is at least about 80% homologous at the DNA level, and at least about 90% homologous at the protein level. Preferred cloning strategies for isolating a nucleic acid molecule that encodes a serotonin receptor molecule of this invention are described in the Examples, and includes the recitation of polynucleotide probes useful for the screening of libraries of nucleic acid molecules believed to contain a target serotonin receptor gene.

Sources of libraries for cloning a serotonin receptor gene of this invention can include genomic DNA or messenger RNA (mRNA) in the form of a cDNA library from a tissue believed to express a serotonin receptor of this invention. Preferred tissues are brain tissues, particularly hypothalamus.

2. Oligonucleotides

The invention also contemplates oligonucleotides useful for methods to detect the presence of a serotonin receptor gene or gene transcript (mRNA) in a tissue by diagnostic detection methods based on the specificity of nucleic acid hybridization or primer extension reactions.

Thus, in one embodiment, any polynucleotide probe having a sequence of a portion of a serotonin receptor gene of this invention, or a related and specific sequence, is contemplated. Particularly preferred are polynucleotides containing a portion of the nucleotide sequence shown in SEQ ID NOs 1, 3, 5, 8 or 10 that encode MR77, REC17, MR22 or REC20.

Hybridization probes can be of a variety of lengths from about 10 to 5000 nucleotides long, although they will typically be about 20 to 500 nucleotides in length. Hybridization methods are extremely well known in the art and will not be described further here.

In a related embodiment, detection of serotonin receptor genes can be conducted by primer extension reactions such as the polymerase chain reaction (PCR). To that end, PCR primers are utilized in pairs, as is well known, based on the nucleotide sequence of the gene to be detected.

Particularly preferred PCR primers can be derived from any portion of a serotonin receptor DNA sequence, but are preferentially from regions which are not conserved in cell receptors, particularly cell membrane receptors, such as the protein region that is an intracellular on extracellular loop area of the sequence.

A preferred PCR primer pair useful for detecting MR77 have the nucleotide sequences:

CAAGCAAGTAGGATTGCAAAG, and

CACAAGCTTTTGGAATGCTTT, and correspond to nucleotides 870–890 and the reverse complement of 1310–1290, respectively (SEQ ID NOs 72 and 73). Nucleotide primers from the corresponding region of the other serotonin receptors described herein are readily prepared and used to as PCR primers for detection of the presence or expression of the corresponding receptor gene.

3. Expression Vectors

In addition, the invention contemplates a recombinant DNA molecule (rDNA) containing a DNA segment of this invention encoding a serotonin receptor described herein. A rDNA can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. A vector adapted for expression of a gene product and capable of directing the expression of a serotonin receptor gene is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of a serotonin receptor structural gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of a serotonin receptor gene in a bacterial host cell, such as E. coli, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), pRc/CMV (Invitrogen, Inc.), the vector pCMV4 described herein, and the like eucaryotic expression vectors.

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982). Alternatively, the selectable marker can be present on a separate plasmid, and the two vectors are introduced by co-transfection of the host cell, and selected by culturing in the appropriate drug for the selectable marker.

4. Inhibitory Nucleic Acids

In accordance with one embodiment of the invention, nucleic acid molecules can be used in methodologies for the inhibition of serotonin receptor gene expression, thereby inhibiting the function of the receptor by blocking its expression.

To that end, the invention contemplates isolated nucleic acid molecules, preferably single-stranded nucleic acid molecules (oligonucleotides), having a sequence complementary to a portion of a structural gene encoding a serotonin receptor of this invention. Typical oligonucleotides for this purpose are about 10 to 5,000, preferably about 20–1000, nucleotides in length and have a sequence capable of hybridizing specifically with a structural protein region of the nucleotide sequence that encodes a serotonin receptor of this invention.

In one embodiment, the invention contemplates repetitive units of the nucleotide sequence complementary to a portion of a serotonin receptor structural gene so as to present multiple sites for complementary binding to the structural gene. This feature may be provided in a single nucleic acid segment having repeating sequences defining multiple portions of a structural gene, by physical conjugation of DNA segments each containing a single portion of a structural gene, or a combination thereof comprising conjugates of DNA segments, each having one or more sequences complementary to a structural gene.

It is also contemplated that nucleotide base modifications can be made to provide certain advantages to a DNA segments of this invention, referred to as nucleotide analogs.

A nucleotide analog refers to moieties which function similarly to nucleotide sequences in a nucleic acid molecule of this invention but which have non-naturally occurring portions. Thus, nucleotide analogs can have altered sugar moieties or inter-sugar linkages. Exemplary are the phosphorothioate and other sulfur-containing species, analogs having altered base units, or other modifications consistent with the spirit of this invention.

Preferred modifications include, but are not limited to, the ethyl or methyl phosphonate modifications disclosed in U.S. Pat. No. 4,469,863 and the phosphorothioate modified deoxyribonucleotides described by LaPlanche et al., *Nucl. Acids Res.*, 14:9081, 1986; and Stec et al., *J. Am. Chem. Soc.*, 106:6077, 1984. These modifications provide resistance to nucleolytic degradation, thereby contributing to the increased half-life in therapeutic modalities. Preferred modifications are the modifications of the 3'-terminus using phosphothioate (PS) sulfurization modification described by Stein et al., *Nucl. Acids Res.*, 16:3209, 1988.

In accordance with the methods of this invention in certain preferred embodiments, at least some of the phosphodiester bonds of the nucleotide sequence can be substituted with a structure which functions to enhance the ability of the compositions to penetrate into the region of cells where the serotonin receptor structural gene to be inhibited is located. It is preferred that such linkages be sulfur containing as discussed above, such as phosphorotioate bonds. Other substitutions can include alkyl phosphothioate bonds, N-alkyl phosphoramidates, phosphorodithioates, alkyl phosphonates, and short chain alkyl or cycloalkyl structures. In accordance with other preferred embodiments, the phosphodiester bonds are substituted with structures which are, at once, substantially nonionic and non-chiral.

D. Cell Lines Expressing Serotonin Receptors

The invention also contemplates a host cell transformed with a recombinant DNA (rDNA) molecule of the present invention. The host cell can be either procaryotic or eucaryotic, although eucaryotic cells are preferred, particularly mammalian cells. Preferred cells are isolated, that is, substantially homogeneous and therefor free from other cell types or other cells having different serotonin receptor subfamily members or types.

A cell expressing a serotonin receptor of this invention has a variety of uses according to this invention. Particularly preferred are uses in panels of cell lines, each expressing a different serotonin receptor subfamily (or type) member for the purpose of screening pharmaceutical compound banks for the presence of receptor-specific ligands, i.e., in drug screening assays as described herein. Thus, particularly preferred are cells containing a rDNA molecule that expresses a serotonin receptor protein of this invention, and particularly that express a serotonin receptor as a cell surface receptor protein.

Eucaryotic cells useful for expression of a serotonin receptor protein are not limited, so long as the cell line is compatible with cell culture methods and compatible with the propagation of the expression vector and expression of the serotonin receptor protein gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 (ATCC CRL 1658), baby hamster kidney cells (BHK), COS-7, COS-1, HEK293 (ATCC CRL 1573), Ltk-1, AV-12 (ATCC CRL 9595), and the like eucaryotic tissue culture cell lines. Particularly preferred and exemplary are HELA cells (ATCC CCL 2) or the COS-M6 cell, a subclone of COS-7 obtainable from J. L. Goldstein (Univ. of Texas Health Sciences, Dallas) described herein.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982).

With regard to transformation of vertebrate cells with vectors containing rDNAs, see, for example, Graham et al., *Virol.*, 52:456 (1973); Wigler et al., *Proc. Natl. Acad. Sci. USA*, 76:1373–76 (1979), and the teachings herein.

Successfully transformed cells, i.e., cells that contain a rDNA molecule of the present invention, can be identified by well known techniques. For example, cells resulting from the introduction of an rDNA of the present invention can be cloned to clonally homogeneous cell populations that contain the rDNA. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of serotonin receptor, or by the detection of the serotonin binding activity of the serotonin receptor.

For example, cells successfully transformed with an expression vector produce proteins displaying serotonin receptor antigenicity or biological activity. Samples of cells suspected of being transformed are harvested and assayed for either serotonin biological activity or antigenicity.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying serotonin receptor antigenicity or biologically activity.

Nutrient media useful for culturing transformed host cells are well known in the art and can be obtained from several commercial sources. In embodiments wherein the host cell is mammalian, a "serum-free" medium can be used.

E. Methods for Identifying a Serotonin Receptor Ligand

As discussed in the background, studies on the individual subfamily and subtype serotonin receptors that have been previously described in the published literature reveal characteristic differences in their abilities to bind a number of ligands. However, the structural basis of the distinct ligand-binding properties is not known. Physiologists and pharmacologists classify these different serotonin receptors to different anatomical locations, to different physiological functions and thus to performing different roles in the body to the extent the known receptors are understood.

The ability to selectively bind/modulate function of a serotonin receptor by a ligand is at the heart of useful serotonin receptor pharmacology, and depends on identifying pharmacological molecules which can act a selective ligands for one species of serotonin receptor and not the others. To that end, the elucidation of new serotonin receptors, such as those described herein, provides valuable tools for the search for selective ligands, tools that are useful in ligand binding assays, and in screening assays which indicate selective drug response depending on the serotonin receptor.

Thus, the invention contemplates methods for determining whether a ligand binds to, and preferably whether the ligand activates, a preselected serotonin receptor. The method comprises (1) contacting a cell comprising a recombinant DNA molecule that encodes and expresses a serotonin receptor of this invention under conditions permitting binding of ligands known to bind the serotonin receptor with a candidate ligand, and (2) detecting the presence of the candidate ligand bound to the serotonin receptor, thereby determining whether the ligand binds to the serotonin receptor. The receptor is typically a cell surface protein when expressed by the above cells.

It is also possible to use the above method to determine whether the ligand which binds to the serotonin receptor also activates or motivates the receptor's function. Thus, by evaluating in the detecting step whether the serotonin receptor is activated, one determines whether the ligand is bioactive. Methods for detecting activation of the serotonin receptor can vary, but typically involve measuring changes in intracellular levels of a secondary messenger effected as a result of ligand binding.

Exemplary measurements are described in the Examples.

Thus, a related embodiment contemplates a method for screening drugs to identify a candidate that can activate a preselected serotonin receptor. The method comprises (a) contacting a mammalian cell with said candidate drug under conditions permitting activation of said serotonin receptor by a known serotonin receptor activating drug, said mammalian cell comprising a vector adapted for expressing a serotonin receptor in said mammalian cell, said vector comprising a DNA segment encoding said preselected serotonin receptor selected from the group consisting of $5\text{-HT}_{1E\text{-Like}}$, $5\text{-HT}_{5\alpha}$, $5\text{-HT}_{5\beta}$ and $5\text{-HT}_6$ and said mammalian containing a cell surface serotonin receptor expressed from said vector; and (b) detecting the activation status of said cell surface serotonin receptor, and thereby determining whether the drug activates said receptor.

In a related embodiment, the screening methods can utilize a panel of cell lines each with a different serotonin receptor, thereby providing a panel of serotonin receptors for screening a ligand. The panel can comprise the serotonin receptors of this invention, and can optionally include other serotonin receptors, thereby rendering the panel even more complete. The production of binding data for a ligand against several different serotonin receptors is referred to as a binding profile.

The data in the Examples illustrates a binding profile for a large variety of known serotonin receptor ligands. The profile illustrates that each ligand typically exhibits a different pattern across a series of different serotonin receptors. Similarly, the profile illustrates that each serotonin receptor of this invention is unique in its ligand binding profile, when compared to the profile for a known serotonin receptor.

In a related embodiment, the invention contemplates methods for evaluating the therapeutic effectiveness of a candidate serotonin receptor ligand in vivo. The in vivo evaluation method involves the use of a transgenic animal as described herein.

The transgenic animal can be a "knockout" animal, i.e., having the gene for a target serotonin receptor removed or otherwise defective. In this embodiment, the invention comprises screening for ligands which replenish deficiencies in the serotonin receptor gene that has been knocked out (mutated). The method comprises administering a test amount of a serotonin receptor ligand to be evaluated to the knockout animal, and observing changes in the symptoms indicative of the genetic deficiency, and thereby observing the effectiveness of the ligand at modifying those symptoms.

In a related embodiment, the invention contemplates a drug screening method using a knockout animal which has a human serotonin receptor transgene, that is, the animal is reconstituted with a human serotonin receptor gene. The method involves administering a test amount of a serotonin receptor ligand to be evaluated to the reconstituted knockout animal, and observing changes in the symptoms in the animal associated with the administered ligand, and thereby observing the effectiveness of the ligand at modifying those symptoms mediated by the human serotonin receptor gene.

A further related embodiment involves a screening method in which the reconstituted gene is a mutant serotonin receptor gene, which mutation reflects a known human genetic deficiency. Thus the reconstituted animal provides a model system for studying the defective human gene, and its effect on a whole organism. Furthermore, the reconstituted animal is ideal for screening drugs for effectiveness in treating the symptoms associated with the serotonin receptor gene deficiency.

The preparation of a knockout animal, and reconstituting the serotonin receptor gene in the knockout that was removed, is described elsewhere herein.

F. Polypeptides

As used herein, the phrase "serotonin receptor polypeptide" refers to a polypeptide having an amino acid residue sequence that comprises an amino acid residue sequence that corresponds, and preferably is identical, to a portion of a serotonin receptor of this invention.

A serotonin receptor polypeptide of the present invention has a variety of uses according to the present invention.

Thus, a serotonin receptor polypeptide of this invention is characterized by its ability to immunologically mimic an epitope (antigenic determinant) expressed by a serotonin receptor of this invention. Such a polypeptide is useful herein as a component in an inoculum for producing antibodies that immunoreact with native serotonin receptor. Representative and preferred serotonin receptor polypeptides for use as an immunogen in an inoculum are shown in Tables 3 and 4 herein.

As used herein, the phrase "immunologically mimic" in its various grammatical forms refers to the ability of a serotonin receptor polypeptide of this invention to immunoreact with an antibody of the present invention that recognizes a conserved native epitope of a serotonin receptor as defined herein.

It should be understood that a subject polypeptide need not be identical to the amino acid residue sequence of a serotonin receptor, so long as it includes the required sequence.

In addition, certain serotonin receptor polypeptides derived from ligand binding portions of the serotonin receptor have capacity to inhibit the binding of a ligand that would normally bind the serotonin receptor. Such inhibitors of ligand binding are referred to as therapeutic polypeptides because of their inhibitory capacity.

A serotonin receptor polypeptide is preferably no more than about 200 amino acid residues in length for reasons of ease of synthesis. Thus, it more preferred that a serotonin receptor polypeptide be no more that about 100 amino acid residues, still more preferably no more than about 50 residues, and most preferably less than 30 amino acid residues in length. In one embodiment, a MR77 serotonin receptor polypeptide of the present invention has a length of no more than about 100 amino acid residues, has an amino acid residue sequence that corresponds to the sequence of human MR77 shown in SEQ ID NO 9, respectively, and includes an amino acid residue sequence represented by a formula selected from the group consisting of:

—MIKEELNGQVLLESGEK—, and (SEQ ID NO 36)
—HSTVKSPRSELKGEKSWR—. (SEQ ID NO 37)

An exemplary and preferred polypeptide in this embodiment has an amino acid residue sequence selected from the group consisting of:

MIKEELNGQVLLESGEK, and (SEQ ID NO 36)
HSTVKSPRSELKGEKSWR. (SEQ ID NO 37)

In a related embodiment, a MR22 serotonin receptor polypeptide of the present invention has a length of no more than about 100 amino acid residues, has an amino acid residue sequence that corresponds to the sequence of MR22 shown in SEQ ID NO 2, and includes an amino acid residue sequence represented by a formula selected from the group consisting of:

—WTITRHLQYTLRTRRR—, (SEQ ID NO 38)
—VVPLPATTQAKEAPQESETV—, (SEQ ID NO 39)
—RATVAFQTSGDSWREQKEKR—, and (SEQ ID NO 40)
—KNYNNAFKSLFTKQR—, (SEQ ID NO 41)

An exemplary and preferred polypeptide in this embodiment has an amino acid residue sequence selected from the group consisting of:

WTITRHLQYTLRTRRR, (SEQ ID NO 38)
VVPLPATTQAKEAPQESETV, (SEQ ID NO 39)
RATVAFQTSGDSWREQKEKR, and (SEQ ID NO 40)
KNYNNAFKSLFTKQR, (SEQ ID NO 41)

In a related embodiment, a REC17 serotonin receptor polypeptide of the present invention has a length of no more than about 100 amino acid residues, has an amino acid residue sequence that corresponds to the sequence of REC17 shown in SEQ ID NO 4, and includes an amino acid residue sequence represented by a formula selected from the group consisting of:

—VSPIPEAVEVKDASQHPQM—, and (SEQ ID NO 42)
—RSYSSAFKVFFSKQQ—. (SEQ ID NO 43)

An exemplary and preferred polypeptide in this embodiment has an amino acid residue sequence selected from the group consisting of:

VSPIPEAVEVKDASQHPQM, and (SEQ ID NO 42)
RSYSSAFKVFFSKQQ. (SEQ ID NO 43)

In a related embodiment, a REC20 serotonin receptor polypeptide of the present invention has a length of no more than about 100 amino acid residues, has an amino acid residue sequence that corresponds to the sequence of REC20 shown in SEQ ID NO 11, and includes an amino acid residue sequence represented by a formula selected from the group consisting of:

—RKSAAKHKFPGFPRVQPES—, (SEQ ID NO 44)
—PEVGRGLQDLSPDGGAHPVVS—, and (SEQ ID NO 45)
—SRLLKHERKNISIFKREQK—. (SEQ ID NO 46)

An exemplary and preferred polypeptide in this embodiment has an amino acid residue sequence selected from the group consisting of:

RKSAAKHKFPGFPRVQPES, (SEQ ID NO 44)
PEVGRGLQDLSPDGGAHPVVS, and (SEQ ID NO 45)
SRLLKHERKNISIFKREQK. (SEQ ID NO 46)

The invention also contemplates serotonin receptor polypeptides which are specifically designed for their capacity to mimic exposed regions of serotonin receptor involved in serotonin receptor binding interactions and thereby receptor function. Therefore, these polypeptides have the capacity to function as analogs to the serotonin receptor, and thereby block function.

In addition, these polypeptides corresponding to exposed domains have the ability to induce antibody molecules that immunoreact with a serotonin receptor of this invention at portions of the serotonin receptor involved in receptor protein function, and therefor the antibodies are also useful at modulating normal receptor function.

Candidate polypeptides derived from exposed regions of a serotonin receptor are shown in Table 4, with the domain of the receptor being indicated also. For example, amino terminus region polypeptides are indicated by "N-terminus", extracellular loop structures are indicated by "EC loop #", and carboxy terminus region polypeptides are indicated by "C-terminus".

Thus, the present invention also contemplates a serotonin receptor polypeptide that has a length of no more than about 100 amino acid residues, has an amino acid residue sequence that corresponds to the sequence of its corresponding serotonin receptor shown in the sequence listings, and includes an amino acid residue sequence represented by a formula selected from the group consisting of the polypeptides shown in Table 4. In this embodiment, the polypeptide is further characterized as having the ability to mimic a serotonin receptor epitope and thereby inhibits receptor function in a classic receptor activation assay.

Preferred exposed region polypeptides have the sequence shown in Table 4.

Due to the three dimensional structure of a native folded serotonin receptor molecule, the present invention contemplates that multiple regions of protein serotonin receptor are involved in receptor function, which multiple and various regions are defined by the various serotonin receptor polypeptides described above. The ability of the above-described serotonin receptor polypeptides to inhibit receptor-ligand binding can readily be measured in a ligand binding assay as is shown in the Examples herein. Similarly, the ability of the above-described serotonin receptor polypeptides to inhibit receptor function can readily be measured in a receptor activation assay as is described herein.

Thus, in another embodiment, the invention contemplates serotonin receptor polypeptide compositions that comprise one or more of the different serotonin receptor polypeptides described above which inhibit serotonin receptor function, admixed in combinations to provide simultaneous inhibition of multiple contact sites on the serotonin receptor. A subject polypeptide includes any analog, fragment or chemical derivative of a polypeptide whose amino acid residue sequence is shown herein so long as the polypeptide is capable of mimicking an epitope of a serotonin receptor. Therefore, a present polypeptide can be subject to various changes, substitutions, insertions, and deletions where such changes provide for certain advantages in its use. In this regard, a serotonin receptor polypeptide of this invention corresponds to, rather than is identical to, the sequence of a serotonin receptor where one or more changes are made and it retains the ability to induce antibodies that immunoreact with a serotonin receptor of this invention.

The term "analog" includes any polypeptide having an amino acid residue sequence substantially identical to a sequence specifically shown herein in which one or more residues have been conservatively substituted with a functionally similar residue and which displays the ability to induce antibody production as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a serotonin receptor, it is typically because one or more conservative or non-conservative substitutions have been made, usually no more than about 30 number percent, more usually no more than 20 number percent, and preferably no more than 10 number percent of the amino acid residues are substituted. Additional residues may also be added at either terminus for the purpose of providing a "linker" by which the polypeptides of this invention can be conveniently affixed to a label or solid matrix, or carrier. Preferably the linker residues do not form a serotonin receptor epitopes, i.e., are not similar is structure to a serotonin receptor.

Labels, solid matrices and carriers that can be used with the polypeptides of this invention are described hereinbelow.

Amino acid residue linkers are usually at least one residue and can be 40 or more residues, more often 1 to 10 residues, but do not form a serotonin receptor epitopes. Typical amino acid residues used for linking are tyrosine, cysteine, lysine, glutamic and aspartic acid, or the like. In addition, a subject polypeptide can differ, unless otherwise specified, from the natural sequence of a serotonin receptor by the sequence being modified by terminal-$NH_2$ acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, a serotonin receptor polypeptide of the present invention is capable of inducing antibodies that immunoreact with serotonin receptor. In view of the well established principle of immunologic cross-reactivity, the present invention therefore contemplates antigenically related variants of the polypeptides shown in Tables 3 and 4.

An "antigenically related variant" is a subject polypeptide that is capable of inducing antibody molecules that immunoreact with a polypeptide from Tables 3 or 4 and with a serotonin receptor of this invention.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono—, di— and tri-alkyl and aryl amines (e.g. triethylamine, diisopropyl amine, methyl amine, dimethyl amine and the like) and optionally substituted ethanolamines (e.g. ethanolamine, diethanolamine and the like).

A serotonin receptor polypeptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A serotonin receptor polypeptide can be used, inter alia, in the diagnostic methods and systems of the present invention to detect a serotonin receptor present in a body sample, or can be used to prepare an inoculum as described herein for the preparation of antibodies that immunoreact with conserved epitopes on a serotonin receptor.

In addition, certain of the serotonin receptor polypeptides of this invention can be used in the therapeutic methods of the present invention to inhibit serotonin receptor function as described further herein.

G. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

An antibody of the present invention, i.e., an anti-serotonin receptor antibody, in one embodiment is characterized as comprising antibody molecules that immunoreact with a recombinant serotonin receptor of this invention. Preferably, an antibody further immunoreacts with a serotonin receptor polypeptide of the present invention.

More preferably, an anti-serotonin receptor antibody is substantially free of the ability to immunoreact with other different serotonin receptor proteins from other subfamilies. Thus a preferred antibody is immunospecific for the serotonin receptor with which it immunoreacts, and can be used diagnostically to selectively detect the subfamily and type of serotonin receptor present in a tissue or body sample according to the diagnostic methods described further herein.

By "substantially free" means that the antibody molecules do not immunoreact with the stated antigen at levels within one order of magnitude, and preferably within two orders of magnitude, of the level of immunoreaction with a species of antigen recited to immunoreact with the antibody molecule when immunoreaction is expressed as an equilibrium constant between bound (immunoreacted) and nonbound antigen.

Thus, the invention claims an anti-serotonin receptor polypeptide antibody that immunoreacts with any of the serotonin receptor polypeptides of this invention, and also immunoreacts with the corresponding recombinant serotonin receptor protein. Preferably, and antibody is substantially free from immunoreaction with a serotonin receptor from a different subfamily or type. Assays for immunoreaction useful for assessing immunoreactivity are described herein.

In one embodiment, antibody molecules are described that immunoreact with a serotonin receptor polypeptide of the present invention and that have the capacity to immunoreact with an exposed site on a serotonin receptor that is required for serotonin receptor function. Thus, preferred antibody molecules in this embodiment also inhibit serotonin receptor function, and are therefore useful therapeutically to block the receptor's function.

Exemplary serotonin receptor inhibitory antibodies immunoreact with a serotonin receptor polypeptide described herein that defines an exposed region of a serotonin receptor that is involved in serotonin receptor function, such as ligand binding.

An antibody of the present invention is typically produced by immunizing a mammal with an inoculum containing an serotonin receptor polypeptide of this invention and thereby induce in the mammal antibody molecules having immunospecificity for immunizing polypeptide. The antibody molecules are then collected from the mammal and isolated to the extent desired by well known techniques such as, for example, by using DEAE Sephadex to obtain the IgG fraction. Exemplary antibody preparation methods using serotonin receptor polypeptides in the immunogen are described herein in the Examples.

The preparation of antibodies against polypeptide is well known in the art. See Staudt et al., *J. Exp. Med.*, 157:687–704 (1983), or the teachings of Sutcliffe, J. G., as described in U.S. Pat. No. 4,900,811, the teaching of which are hereby incorporated by reference.

Briefly, to produce a peptide antibody composition of this invention, a laboratory mammal is inoculated with an immunologically effective amount of a serotonin receptor polypeptide, typically as present in a vaccine of the present invention. The anti-serotonin receptor polypeptide antibody molecules thereby induced are then collected from the mammal and those immunospecific for both the serotonin receptor polypeptide and the corresponding recombinant serotonin receptor are isolated to the extent desired by well known techniques such as, for example, by immunoaffinity chromatography.

To enhance the specificity of the antibody, the antibodies are preferably purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" in its various grammatical forms is used herein to describe a composition containing a serotonin receptor polypeptide of this invention as an active ingredient used for the preparation of antibodies against a serotonin receptor polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used.

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. No. 4,493,795, No. 3,791,932 and No. 3,839,153. In addition, a site-directed coupling reaction can be carried out so that any loss of activity due to polypeptide orientation after coupling can be minimized. See, for example, Rodwell et al., *Biotech.*, 3:889–894 (1985), and U.S. Pat. No. 4,671,958.

Exemplary additional linking procedures include the use of Michael addition reaction products, dialdehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly D-lysine:D-glutamic acid, and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen is well known in the art. Inocula typically contain polypeptide concentrations of about 10 micrograms ($\mu$g) to about 500 milligrams (mg) per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The antibody so produced can be used, inter alia, in the diagnostic methods and systems of the present invention to detect a serotonin receptor present in a sample such as a tissue section or body fluid sample. Anti-serotonin receptor antibodies that inhibit serotonin receptor function can also be used in vivo in therapeutic methods as described herein.

A preferred anti-serotonin receptor antibody is a monoclonal antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A preferred monoclonal antibody of this invention comprises antibody molecules that immunoreact with a 1) recombinant serotonin receptor, and 2) a serotonin receptor polypeptide of the present invention as described for the anti-serotonin receptor antibodies of this invention.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, Nature, 256:495–497 (1975), the description of which is incorporated by reference. The hybridoma supernates so prepared can be screened for the presence of antibody molecules that immunoreact with a serotonin receptor polypeptide, or for inhibition serotonin receptor function.

Briefly, to form the hybridoma from which the monoclonal antibody composition is produced, a myeloma or other self-perpetuating cell line is fused with lymphocytes obtained from the spleen of a mammal hyperimmunized with a serotonin receptor antigen, such as is present in a serotonin receptor polypeptide of this invention. The polypeptide-induced hybridoma technology is described by Niman et al., Proc. Natl. Acad. Sci., USA, 80:4949–4953 (1983), the description of which is incorporated herein by reference.

It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in Example 4.

A monoclonal antibody of the present invention can also be produced by initiating a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's Minimal Essential Medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Other methods of producing a monoclonal antibody, a hybridoma cell, or a hybridoma cell culture are also well known. See, for example, the method of isolating monoclonal antibodies from an immunological repertoire as described by Sastry, et al., Proc. Natl. Acad. Sci. USA, 86:5728–5732 (1989); and Huse et al., Science, 246:1275–1281 (1989).

The monoclonal antibodies of this invention can be used in the same manner as disclosed herein for antibodies of the present invention.

For example, the monoclonal antibody can be used in the therapeutic, diagnostic or in vitro methods disclosed herein where immunoreaction with a serotonin receptor is desired.

Also contemplated by this invention is the hybridoma cell, and cultures containing a hybridoma cell that produce a monoclonal antibody of this invention.

H. Therapeutic Methods and Compositions

1. Therapeutic Methods

It is contemplated that the certain reagents described in the present invention have the capacity to modulate serotonin receptor function, and therefore are useful in therapeutic methods for conditions mediated by the serotonin receptor.

Serotonin receptor polypeptides that mimic exposed regions of a serotonin receptor have the ability to function as analogs and compete for binding to the natural ligand, or for other agents that would normally interact with the receptor, thereby inhibiting binding of that ligand/agent to the receptor.

Furthermore, antibodies and monoclonal antibodies of the present invention that bind to exposed regions of a serotonin receptor of this invention have the capacity to alter serotonin receptor function by blocking natural interactions with ligand or other agents that normally interact at the site. Exemplary antibodies are the anti-serotonin receptor polypeptide antibodies described earlier that bind "exposed" serotonin receptor polypeptides.

Finally, oligonucleotides are described herein which are complementary to mRNA that encodes a serotonin receptor of this invention and that are useful for reducing gene expression and translation of the serotonin receptor mRNA.

Thus, in one embodiment, the present invention provides a method for modulating serotonin receptor function in a animal or human patient comprising administering to the patient a therapeutically effective amount of a physiologically tolerable composition containing a serotonin receptor polypeptide, anti-serotonin receptor antibody or monoclonal antibody of the present invention.

A therapeutically effective amount of a serotonin receptor polypeptide is a predetermined amount calculated to achieve the desired effect, i.e., to inhibit receptor interaction with its normal target, and thereby interfere with normal receptor function.

Similarly, a therapeutically effective amount of an anti-serotonin receptor antibody is a predetermined amount calculated to achieve the desired effect, i.e., to immunoreact with the receptor, and thereby inhibit the receptor's ability to interaction with its normal target, and thereby interfere with normal receptor function.

The in vivo inhibition of a serotonin receptor function using a serotonin receptor polypeptide or anti-serotonin receptor antibody of this invention is a particularly preferred embodiment and is desirable in a variety of clinical settings, such as where the patient is exhibiting symptoms of an over or under activated serotonin receptor.

A therapeutically effective amount of a serotonin receptor polypeptide of this invention is typically an amount of serotonin receptor polypeptide such that when administered in a physiologically tolerable composition is sufficient to achieve a plasma concentration of from about 0.1 micromolar ($\mu$M) to about 100 $\mu$M, and preferably from about 0.5 $\mu$M to about 10 $\mu$M.

A therapeutically effective amount of an antibody of this invention is typically an amount of antibody such that when administered in a physiologically tolerable composition is sufficient to achieve a plasma concentration of from about 0.1 microgram ($\mu$g) per milliliter (ml) to about 100 $\mu$g/ml, preferably from about 1 $\mu$g/ml to about 5 $\mu$g/ml, and usually about 5 $\mu$g/ml.

The effectiveness of the therapy can be determined by observing ablation of the symptoms associated with the function of the serotonin receptor being inhibited.

The therapeutic compositions containing a serotonin receptor polypeptide or anti-serotonin receptor antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are particular to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective therapeutic amounts of a serotonin receptor polypeptide, antibody, or monoclonal antibody, a diagnostic method of this invention for detecting a serotonin receptor polypeptide, antibody, or monoclonal antibody, respectively, in the subject's blood is useful to characterize the fate of the administered therapeutic composition. Suitable diagnostic (monitoring) assays are described herein.

2. Methods for Inhibiting Gene Expression

In another embodiment, the invention contemplates the use of nucleic acids encoding portions of a serotonin receptor gene for inhibiting gene expression and function.

Thus, the present invention provides for a method for inhibiting expression of serotonin receptor gene products and thereby inhibiting the function of the target serotonin receptor. The DNA segments and their compositions have a number of uses, and may be used in vitro or in vivo. In vitro, the compositions may be used to block function and/or expression of serotonin receptor in cell cultures, tissues, organs and the like materials that can express serotonin receptor. In vivo, the compositions may be used prophylactically or therapeutically for inhibiting expression of a serotonin receptor gene, and by inhibiting diseases associated with the expression of the serotonin receptor gene.

The method comprises, in one embodiment, contacting human cells with a therapeutically effective amount of a pharmaceutically acceptable composition comprising a DNA segment of this invention. In a related embodiment, the contacting involves introducing the DNA segment composition into cells having a serotonin receptor.

The DNA segment can be in a variety of forms, but is preferably in a single-stranded form to facilitate complementary hybridization to the target mRNA in the cell in which the serotonin receptor gene expression is to be altered.

The term "cells" is intended to include a plurality of cells as well as single cells. The cells can be isolated, or can be cells that form a larger organization of cells to form a tissue or organ.

In a further embodiment, the invention contemplated the method of inhibiting the expression of serotonin receptor genes in a patient comprising administration to the patient of a therapeutically effective amount of a DNA segment composition of this invention in a pharmaceutically acceptable excipient. In cases where the distribution of the serotonin receptor is believed to be disseminated in the body, the administration of therapeutic oligonucleotide can be systemic. Alternatively, the target serotonin receptor can be localized to a tissue, and the therapeutic method can likewise be directed at delivering the therapeutic DNA segment to the tissue to be treated.

The therapeutic compounds and compositions are generally administered so as to contact the cells or the tissue containing cells which contain the target serotonin receptor. This administration can be accomplished by introduction of the composition internally such as orally, intravenously, intramuscularly, intranasally or via inhalation of aerosols containing the composition, and the like, or by introduction into or onto a tissue system as by introduction transdermally, topically or intralesionally, in suppositories, or by intra-orbital injection, and the like.

The concentration of the active DNA segment ingredient in a therapeutic composition will vary, depending upon the desired dosage, use, frequency of administration, and the like. The amount used will be a therapeutically effective amount and will depend upon a number of factors, including the route of administration, the formulation of the composition, the number and frequency of treatments and the activity of the formulation employed.

The use of therapeutic DNA segments, and therefore the delivery of those DNA segments into cells where they are effective, has been described in a variety of settings. It is generally known that therapeutically effective intracellular levels of nucleic acids, and particularly smaller nucleic acids such as DNA segments and oligonucleotides, can be achieved by either exposing cells to solutions containing nucleic acids or by introduction of the nucleic acids into the inside of the cell. Upon exposure, nucleic acids are taken up by the cell where they exert their effectiveness. In addition, direct introduction into the cell can be provided by a variety of means, including microinjection, delivery by the use of specific uptake vehicles, and the like.

The pharmaceutical composition containing the therapeutic oligonucleotide preferably also contains physiologically acceptable carriers, in particular hydrophobic carriers which facilitate carrying the oligonucleotide through the cell membrane.

Exemplary descriptions of the delivery of therapeutic DNA segments and oligonucleotides into cells can be found in the teachings of U.S. Pat. Nos. 5,04,820, 4,806,463, 4,757,055, and 4,689,320, which teachings are hereby incorporated by reference.

A therapeutically effective amount is a predetermined amount calculated to achieve the desired effect, i.e., to bind to a serotonin receptor gene present and thereby inhibit function of the gene.

As is apparent to one skilled in the art, the copy number of a serotonin receptor gene may vary, thereby presenting a variable amount of target with which to hybridize. Thus it is preferred that the therapeutic method achieve an intracellular concentration of a therapeutic DNA segment of this invention in molar excess to the copy number of the gene in the cell, and preferably at least a ten-fold, more preferably at least a one-hundred fold, and still more preferably at least a one thousand-fold excess of therapeutic DNA segments relative to the gene copy number per cell. A preferred effective amount is an intracellular concentration of from about 1 nanomolar (nM) to about 100 micromolar ($\mu$M), particularly about 50 nM to about 1 $\mu$M.

Alternatively, a therapeutically effective amount can be expressed as an extracellular concentration. Thus it is preferred to expose an cell containing a serotonin receptor gene to a concentration of from about 100 nM to about 10 millimolar (mM), and preferably about 10 $\mu$M to 1 mM. Thus, in embodiments where delivery of a therapeutic DNA segment composition is designed to expose cells to the nucleic acid for cellular uptake, it is preferred that the local concentration of the DNA segment in the area of the tissue to be treated reach the extracellular concentrations recited above.

For patient dosages, using a 20 nucleotide base double-stranded DNA segment as the standard, a typical dosage of therapeutic composition for a 70 kilogram (kg) human contains in the range of about 0.1 milligram (mg) to about 1 gram of 20-mer DNA segment per day, and more usually in the range of about 1 mg to 100 mg per day. Stated differently, a dosage of about 1 $\mu$g/kg/g day to about 15 mg/kg/day, and preferably about 15 to 1500 $\mu$g/kg/day is contemplated.

The in vivo inhibition of serotonin receptor gene expression and/or function by a therapeutic composition of this invention is desirable in a variety of clinical settings, such as where the patient is at risk for disease based on expression of the serotonin receptor gene. The disease depends on the particular serotonin receptor and the physiological role that receptor plays in the subject patient.

Serotonin receptors are known to participate in a variety of neurological processes and pathologies including dementia, Parkinson's disease, eating disorders, pathological anxiety, migraine headaches, insomnia and other conditions.

In view of the evidence herein that the serotonin receptor 5-HT$_6$ (REC20) participates in managing circadian rhythms of the superchiasmatic nucleus, the therapeutic reagents described herein specific for REC20 are particularly suited to therapeutic methods for altering the phase of the circadian rhythm clock in a mammal. Therefor, the invention contemplates a method for altering the circadian rhythm phasing of a mammal, or treating any disorder associated with phasing of the clock, comprising administering a therapeutic composition of this invention specific for REC20 in an amount sufficient to inhibit REC20 serotonin receptor function.

3. Therapeutic Compositions

The present invention contemplates therapeutic compositions useful for practicing the therapeutic methods described herein. Therapeutic compositions of the present invention contain a physiologically tolerable carrier together with a therapeutic reagent of this invention, namely a serotonin receptor polypeptide, an anti-serotonin receptor antibody or monoclonal antibody, or oligonucleotide as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

As described herein, for intracellular delivery of oligonucleotides, specialized carriers may be used which facilitate transport of the oligonucleotide across the cell membrane. These typically are hydrophobic compositions, or include additional reagents which target delivery to and/or into cells.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an amount of a serotonin receptor polypeptide or anti-serotonin receptor antibody molecule of the present invention sufficient to inhibit serotonin receptor function. Typically this is an amount of at least 0.1 weight percent, and more preferably is at least 1 weight percent, of peptide or antibody per weight of total therapeutic composition. A weight percent is a ratio by weight of peptide or antibody to total composition. Thus, for example, 0.1 weight percent is 0.1 grams of polypeptide per 100 grams of total composition.

I. Diagnostic Systems and Methods

1. Diagnostic Systems

The present invention also describes a diagnostic system, preferably in kit form, for assaying for the presence of a serotonin receptor of this invention in a body sample, such brain tissue, cell suspensions or tissue sections, or body fluid samples such as blood, plasma or serum, where it is desirable to detect the presence, and preferably the amount, of a serotonin receptor in the sample according to the diagnostic methods described herein.

In a related embodiment, a nucleic acid molecule can be used as a probe (an oligonucleotide) to detect the presence of a gene or mRNA in a cell that is diagnostic for the presence or expression of a serotonin receptor gene in the cell. The nucleic acid molecule probes were described in detail earlier.

The diagnostic system includes, in an amount sufficient to perform at least one assay, a subject serotonin receptor polypeptide, a subject antibody or monoclonal antibody, and/or a subject nucleic acid molecule probe of the present invention, as a separately packaged reagent.

In another embodiment, a diagnostic system, preferably in kit form, is contemplated for assaying for the presence of a serotonin receptor polypeptide or anti-serotonin receptor antibody in a body fluid sample such as for monitoring the fate of therapeutically administered serotonin receptor polypeptide or anti-serotonin receptor antibody. The system includes, in an amount sufficient for at least one assay, a subject serotonin receptor polypeptide and/or a subject antibody as a separately packaged immunochemical reagent.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a polypeptide, polyclonal antibody or monoclonal antibody of the present invention. Thus, for example, a package can be a glass vial used to contain milligram quantities of a contemplated polypeptide or antibody or it can be a microtiter plate well to which microgram quantities of a contemplated polypeptide or antibody have been operatively affixed, i.e., linked so as to be capable of being immunologically bound by an antibody or antigen, respectively.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention preferably also includes a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Anti-* body As a Tool, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$ indium or $^3$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of a serotonin receptor in a sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in some embodiments, a serotonin receptor polypeptide, an antibody or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron ($\mu$) to about 5 millimeters (mm) in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

2. Diagnostic Methods

The present invention contemplates various assay methods for determining the presence, and preferably amount, of a serotonin receptor in a body sample such as a tissue sample, including tissue mass or section, or a biological fluid sample using a polypeptide, polyclonal antibody or monoclonal antibody of this invention as an immunochemical reagent to form an immunoreaction product whose amount relates, either directly or indirectly, to the amount of a serotonin receptor in the sample.

Those skilled in the art will understand that there are numerous well known clinical diagnostic chemistry procedures in which an immunochemical reagent of this invention can be used to form an immunoreaction product whose amount relates to the amount of serotonin receptor in a body sample. Thus, while exemplary assay methods are described herein, the invention is not so limited.

Additionally, one can use the nucleic acid molecule probes described herein to detect the presence in a cell or tissue of a serotonin receptor gene or expressed gene in the form of mRNA encoding a serotonin receptor of this invention, as described further herein. Suitable probe-based assays are described in Sutcliffe, U.S. Pat. No. 4,900,811, the disclosures of which are incorporated by reference.

Various heterogenous and homogeneous protocols, either competitive or noncompetitive, can be employed in performing an assay method of this invention.

For example, one embodiment contemplates a method for assaying the amount of serotonin receptor in a sample that utilizes an anti-serotonin receptor antibody to immunoreact with a serotonin receptor in a sample. In this embodiment, the antibody immunoreacts with a serotonin receptor to form a serotonin receptor-antibody immunoreaction complex, and the complex is detected indicating the presence of a serotonin receptor.

An immunoassay method using an anti-serotonin receptor antibody molecule for assaying the amount of serotonin receptor in a sample typically comprises the steps of:

(a) Forming an immunoreaction admixture by admixing a sample with an anti-serotonin receptor antibody of the present invention, preferably a monoclonal antibody. The sample is typically in the form of a fixed tissue section in a solid phase such that the immunoreaction admixture has both a liquid phase and a solid phase, and the antibody functions as a detection reagent for the presence of a serotonin receptor in the sample.

Preferably, the sample is a brain tissue sample that has been prepared for immunohistological staining as is well known, although other tissue samples may be adsorbed onto a solid phase, including tissue extracts or body fluid. In that case the adsorption onto a solid phase can be conducted as described for well known Western blot procedures.

(b) The immunoreaction admixture is maintained under biological assay conditions for a predetermined time period such as about 10 minutes to about 16–20 hours at a temperature of about 4° C. to about 45° C. that, such time being sufficient for the serotonin receptor present in the sample in the solid phase to immunoreact with (immunologically bind) the antibody and form a serotonin receptor-containing immunoreaction product (immunocomplex) in the solid phase.

Biological assay conditions are those that maintain the biological activity of the immunochemical reagents of this invention and the serotonin receptor sought to be assayed. Those conditions include a temperature range of about 4° C. to about 45° C., a pH value range of about 5 to about 9 and an ionic strength varying from that of distilled water to that of about one molar sodium chloride. Methods for optimizing such conditions are well known in the art.

(c) The amount of serotonin receptor-containing immunoreaction product that formed in step (b) is determined, thereby determining the amount of serotonin receptor present in the sample.

Determining the amount of the immunoreaction product, either directly or indirectly, can be accomplished by assay techniques well known in the art, and typically depend on the type of indicating means used.

Preferably, the determining of step (c) comprises the steps of:

(i) admixing the serotonin receptor-containing immunoreaction product in the solid phase with a second antibody to form a second immunoreaction admixture having a liquid phase and a solid phase, said second antibody molecule having the capacity to immunoreact with the first antibody (primary) in the solid phase immunoreaction product.

Antibodies useful as the second antibody include polyclonal or monoclonal antibody preparations raised against the primary antibody.

(ii) maintaining said second immunoreaction admixture for a time period sufficient for said second antibody to complex with the immunoreaction product and form a second immunoreaction product in the solid phase, and (iii) determining the amount of second antibody present in the second immunoreaction product and thereby the amount of immunoreaction product formed in step (c).

In one embodiment, the second antibody is a labelled antibody such that the label provides an indicating means to detect the presence of the second immunoreaction product formed. The label is measured in the second immunoreaction product, thereby indicating the presence, and preferably amount, of second antibody in the solid phase.

Alternatively, the amount of second antibody can be determined by preparation of an additional reaction admixture having an indicating means that specifically reacts with (binds to) the second antibody, as is well known. Exemplary are third immunoreaction admixtures with a labelled anti-immunoglobulin antibody molecule specific for the second antibody. After third immunoreaction, the formed third immunoreaction product is detected through the presence of the label.

Exemplary methods involve the use of in situ immunoreaction methods using tissue sections, or Western blot procedures, as described by Sutcliffe in U.S. Pat. No. 4,900,811.

Another embodiment is contemplated for assaying the amount of therapeutically administered serotonin receptor polypeptide or anti-serotonin receptor antibody in a body fluid sample such as blood, plasma or serum. The method utilizes a competition reaction in which either a serotonin receptor polypeptide or an anti-serotonin receptor antibody molecule of this invention is present in the solid phase as an immobilized immunochemical reagent, and the other of the two reagents is present in solution in the liquid phase, in the form of a labeled reagent. A fluid sample is admixed thereto to form a competition immunoreaction admixture, and the resulting amount of label in the solid phase is proportional, either directly or indirectly, to the amount of serotonin receptor polypeptide or antibody in the fluid sample, depending upon the format.

Thus one version of this embodiment comprises the steps of:

(a) Forming a competition immunoreaction admixture by admixing a vascular fluid sample with:

(1) an anti-serotonin receptor antibody according to this invention containing antibody molecules that immunoreact with a serotonin receptor, said antibody being operatively linked to a solid matrix such that the competition immunoreaction admixture has both a liquid phase and a solid phase, and (2) a polypeptide or recombinant serotonin receptor protein of the present invention that is immunoreactive with the added antibody. The admixed polypeptide/protein in the liquid phase (labeled competing antigen) is operatively linked to an indicating means as described herein.

(b) The competition immunoreaction admixture is then maintained for a time period sufficient for the competing antigen and the body sample antigen present in the liquid phase to compete for immunoreaction with the solid phase antibody. Such immunoreaction conditions are previously described, and result in the formation of an indicating means-containing immunoreaction product comprising the labeled competing antigen in the solid phase.

(c) The amount of indicating means present in the product formed in step (b) is then determined, thereby determining the presence, and preferably amount, of sample antigen present in the vascular fluid sample.

Determining the indicating means in the solid phase is then conducted by the standard methods described herein.

A reverse version of this embodiment comprises the steps of:

(a) Forming a competition immunoreaction admixture by admixing a vascular fluid sample with:

(1) an anti-serotonin receptor antibody according to the present invention; and (2) a serotonin receptor polypeptide or recombinant serotonin receptor of the present invention (capture antigen) that is immunoreactive with the antibody and is operatively linked to a solid matrix such that the competition immunoreaction admixture has both a liquid phase and a solid phase.

(b) The competition immunoreaction admixture is then maintained for a time period sufficient for any serotonin receptor antigen or anti-serotonin receptor antibody in the vascular fluid to compete with the admixed antibody molecules for immunoreaction with the solid phase capture antigen and form an antibody-containing immunoreaction product in the solid phase.

(c) The amount of antibody present in the product formed in step (b) is then determined, thereby determining the presence and/or amount of target material in the vascular fluid sample.

In preferred embodiments, the antibody is operatively linked to an indicating means such that the determining in step (c) comprises determining the amount of indicating means present in the product formed in step (b).

Preferably, the vascular fluid sample is provided to a competition immunoreaction admixture as a known amount of blood, or a blood derived product such as serum or plasma. Further preferred are embodiments wherein the amount of immunochemical reagent in the liquid phase of the immunoreaction admixture is an excess amount relative to the amount of reagent in the solid phase. Typically, a parallel set of competition immunoreactions are established using a known amount of purified recombinant serotonin receptor or polypeptide in a dilution series so that a standard curve can be developed, as is well known. Thus, the amount of product formed in step (c) when using a vascular fluid sample is compared to the standard curve, thereby determining the amount of target antigen present in the vascular fluid.

In another embodiment, the method for assaying the amount of serotonin receptor in a sample utilizes a first capture antibody to capture and immobilize serotonin receptor in the solid phase and a second indicator antibody to indicate the presence of the captured serotonin receptor antigen. In this embodiment, one antibody immunoreacts with a serotonin receptor to form a serotonin receptor-antibody immunoreaction complex, and the other antibody is able to immunoreact with the serotonin receptor while present in the serotonin receptor-antibody immunoreaction complex. This embodiment can be practiced in two formats with the immobilized capture antibody being either of the two above-identified antibodies, and the indicator antibody being the other of the two antibodies.

Where a antibody is in the solid phase as a capture reagent, a preferred means for determining the amount of solid phase reaction product is by the use of a labeled serotonin receptor polypeptide, followed by the detection means described herein for other labeled products in the solid phase. Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

J. Transgenic Animals

In another embodiment, the present invention describes provides transgenic non-human animals.

The transgenic animal can have a exogenous serotonin receptor of this invention due to the presence of a gene encoding and expressing that receptor. By "exogenous" is meant that the animal harbors a gene derived from a different species. Preferably, the transgenic animal harbors a gene that encodes a human serotonin receptor of this invention, and is useful as a model for human serotonin receptor function.

Alternatively, a transgenic animal can have a mutation in a particular member of its own native serotonin receptor subfamily, thereby rendering the native receptor non-functional (i.e., a "knockout" transgenic animal). Such an animal is useful as it presents the clinical conditions associated with the defects in the mutated serotonin receptor, and further can be a model for evaluation of candidate therapeutics that would treat subjects with defects in that serotonin receptor.

Still further, a transgenic animal may be a knockout animal for a preselected serotonin receptor, and further contain an exogenous gene that encodes a homolog of the defective serotonin receptor derived from a different species, such as a human. Such a transgenic animal has a reconstituted serotonin receptor and thereby provides a model for studying the function of the homolog. Particularly preferred is a transgenic animal which contains a human serotonin receptor of this invention in place of the corresponding native serotonin receptor.

Such transgenic animals are useful as models to screen for therapeutic reagents that activate or inhibit the serotonin receptor function, and as models for evaluating efficacy or toxicity of a candidate therapeutic.

Transgenic animals are generally well known, as is their methods of production. Those methods necessarily depend having a cloned gene of interest to transfer, or to mutate, as the case may be.

In accordance with this invention, at least one copy of at least one serotonin receptor gene of this invention is introduced into cells of a non-human animal. Preferably, substantially all of the cells of the animal will contain the transgene.

Thus, the present invention contemplates a nonhuman animal containing a serotonin receptor gene of the present invention integrated in the genome of the animal's somatic and germ cells, i.e., a transgenic animal. Particularly preferred are transgenic mammals, and are utilized as exemplary herein.

Animals containing a transgene encoding a serotonin receptor of the present invention are typically prepared using the standard transgenic technology described in Hogan et al, *Manipulating the Mouse Embryo: A Laboratory Manual*, Cold Spring Harbor, N.Y. (1987); and Palmiter et al, *Ann. Rev. Genet.*, 20:465–499 (1986); which methods are described further herein. Production of transgenic mammals is also possible using the homologous recombination transgenic systems described by Capecchi, *Science*, 244:288–292 (1989). Preparation of transgenic mammals has also been described in U.S. Pat. Nos. 4,736,866, 4,870,009, 4,873,191 and 4,873,316.

One technique for transgenically altering a mammal is to microinject a rDNA into the male pronucleus of the fertilized mammalian egg to cause one or more copies of the rDNA to be retained in the cells of the developing mammal. Usually up to 40 percent of the mammals developing from the injected eggs contain at least 1 copy of the rDNA in their tissues. These transgenic mammals usually transmit the gene through the germ line to the next generation. The progeny of the transgenically manipulated embryos may be tested for the presence of the construct by Southern blot analysis of a segment of tissue. Typically, a small part of the tail is used for this purpose. The stable integration of the rDNA into the genome of the transgenic embryos allows permanent transgenic mammal lines carrying the rDNA to be established.

Alternative methods for producing a non-human mammal containing a rDNA of the present invention include infection of fertilized eggs, embryo-derived stem cells, totipotent embryonal carcinoma (Ec) cells, or early cleavage embryos with viral expression vectors containing the rDNA. See for example, Palmiter et al, *Ann. Rev. Genet.*, 20:465–499 (1986) and Capecchi, *Science*, 244:1288–1292 (1989).

A transgenic mammal can be any species of mammal, including agriculturally significant species, such as sheep, cow, lamb, horse and the like. Preferred are animals significant for scientific purposes, including but not limited to rabbits, primates and rodents, such as mice, rats and the like. A transgenic animal is not human.

A transgenic animal is an animal that has been transformed by the introduction of a recombinant nucleic acid molecule into its genome. Typically, the recombinant nucleic acid molecule will be present in all of the germ cells and somatic cells of the transgenic animal. See for example, Gasser et al, *Science*, 244:1293–1299 (1989); European Pat. Application No. 0257472 filed Aug. 13, 1987 by De La Pena et al; PCT Pub. No. WO 88/02405 filed Oct. 1, 1987 by Trulson et al; PCT Pub. No. WO 87/00551 filed Jul. 16, 1986 by Verma, and PCT Pub. No. WO 88/09374 filed May 20, 1988 by Topfer et al.

Methods for producing transgenic animals containing a rDNA of the present invention include standard transgenic technology; infection of the zygote or organism by viruses including retroviruses; infection of a tissue with viruses and then reintroducing the tissue into an animal; and introduction of a rDNA into an embryonic stem cell of a mammal followed by appropriate manipulation of the embryonic stem cell to produce a transgenic animal. See for example, Wagner et al, U.S. Pat. No. 4,873,191 (Oct. 10, 1989); Rogers et al, *Meth. in Enzvmol.*, 153:253–277 (1987); Verma et al, PCT Publication No. W087/00551; Cocking et al, *Science*, 236:1259–1262 (1987); and Luskin et al, *Neuron* 1:635–647 (1988).

Transgenic animals having at least 1 cell containing the rDNA's of the present invention can be produced using methods well known in the art. See for example, Wagner et al, U.S. Pat. No. 4,873,191 (Oct. 10, 1989); Hogan et al, Manipulating the Mouse Embryo: A Laboratory Manual, Cold Springs Harbor, N.Y. (1987); Capecchi, *Science*, 244:288–292 (1989); and Luskin et al, *Neuron* 1:635–647 (1988).

In preferred embodiments a transgenic mammal of the present invention is produced by:

1) microinjecting a subject rDNA into a fertilized mammalian egg to produce a genetically altered mammalian egg;
2) implanting the genetically altered mammalian egg into a host female mammal;
3) maintaining the host female mammal for a time period equal to a substantial portion of a gestation period of said mammal;
4) harvesting a transgenic mammal having at least one cell containing a rDNA that has developed from the genetically altered mammalian egg.

A fertilized mammalian egg may be obtained from a suitable female mammal by inducing superovulation with gonadotropins. Typically, pregnant mare's serum is used to mimic the follicle-stimulating hormone (FSH) in combination with human chorionic gonadotropin (hCG) to mimic luteinizing hormone (LH). The efficient induction of superovulation in mice depends as is well known on several variables including the age and weight of the females, the dose and timing of the gonadotropin administration, and the particular strain of mice used. In addition, the number of superovulated eggs that become fertilized depends on the reproductive performance of the stud males. See, for example, *Manipulating the Embryo: A Laboratory Manual*, Hogan et al, eds., Cold Spring Harbor, N.Y. (1986).

The rDNA may be microinjected into the mammalian egg to produce a genetically altered mammalian egg using well known techniques. Typically, the rDNA is microinjected directly into the pronuclei of the fertilized mouse eggs as has been described by Gordon et al, *Proc. Natl. Acad. Sci., USA*, 77:7380–7384 (1980). This leads to the stable chromosomal integration of the rDNA in approximately 10 to 40 percent of the surviving embryos. See for example, Brinster et al, *Proc. Natl. Acad. Sci., USA*, 82:4438–4442 (1985). In most cases, the integration appears to occur at the 1 cell stage, as a result the rDNA is present in every cell of the transgenic animal, including all of the primordial germ cells. The number of copies of the foreign rDNA that are retained in each cell can range from 1 to several hundred and does not appear to depend on the number of rDNA injected into the egg as is well known.

An alternative method for introducing genes into the animal's germ line is the infection of embryos with virus vectors. The embryos can be infected by either wild-type or recombinant viruses leading to the stable of integration of viral genomes into the host chromosomes. See, for example, Jaenisch et al, *Cell*, 24:519–529 (1981). One particularly useful class of viral vectors are virus vector derived from retroviruses. Retroviral integration occurs through a precise mechanism, leading to the insertion of single copies of the virus on the host chromosome. The frequency of obtaining transgenic animals by retroviral infection of embryos can be as high as that obtained by microinjection of the rDNA and appears to depend greatly on the titer of virus used. See, for example, van der Putten et al, *Proc. Natl. Acad. Sci., USA*, 82:6148–6152 (1985).

Another method of transferring new genetic information into an animal embryo involves the introduction of the rDNA into embryonic stem cells and then introducing the embryonic stem cells into the embryo. The embryonic stem cells can be derived from normal blastocysts and these cells have been shown to colonize the germ line regularly and the somatic tissues when introduced into the embryo. See, for example, Bradley et al, *Nature*, 309:255–256 (1984). Typically, the embryo-derived stem cells are transfected with the rDNA and the embryo-derived stem cells further cultured for a time period sufficient to allow the rDNA to integrate into the genome of the cell. In some situations this integration may occur by homologous recombination with a gene that is present in the genome of the embryo-derived stem cell. See, for example, Capecchi, *Science*, 244:1288–1292 (1989). The embryo stem cells that have incorporated the rDNA into their genome may be selected and used to produce a purified genetically altered embryo derived stem cell population. See, for example, Mansour et al, *Nature*, 336:348 (1988). The embryo derived stem cell is then injected into the blastocoel cavity of a preimplantation mouse embryo and the blastocyst is surgically transferred to the uterus of a foster mother where development is allowed to progress to term. The resulting animal is chimeric in that it is composed from cells derived of both the donor embryo derived stem cells and the host blastocyst. Heterozygous siblings are interbred to produce animals that are homozygous for the rDNA. See for example, Capecchi, *Science*, 244:1288–1292 (1989).

The genetically altered mammalian egg is implanted into host female mammals. Methods for implanting genetically altered mammalian eggs into host females are well known. See, for example, Hogan et al, *Manipulating the Mouse Embryo: A Laboratory Manual*, Cold Spring Harbor Laboratory, Cold Spring Harbor, N.Y. (1986). Pseudopregnant recipient females may be produced by mating females in natural estrus with vasectomized or genetically sterile males. After mating with a sterile male, the female reproduction tract becomes receptive for transferred embryos even though her own unfertilized eggs degenerate. The genetically altered mammalian eggs are then transferred to the ampullae or the uterine horns of the pseudopregnant recipient. If the genetically altered mammalian egg is transferred into the ampullae it must be enclosed in a zona pellucida membrane. If it is transferred into the uterine horns the genetically altered mammalian egg does not require a zona pellucida membrane.

The host female mammals containing the implanted genetically altered mammalian eggs are maintained for a sufficient time period to give birth to a transgenic mammal having at least 1 cell containing a rDNA of the present invention that has developed from the genetically altered mammalian egg. Typically this gestation period is between 19 to 20 days depending on the particular mouse strain. The breeding and care of mice is well known. See for example, *Manipulating the Mouse Embryo: A Laboratory Manual*, Hogan et al, eds., Cold Spring Harbor, N.Y., (1986).

The infection of cells within an animal using a replication incompetent retroviral vector has been described by Luskin et al, *Neuron*, 1:635–647 (1988).

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of MR22 and REC17 Isolated Serotonin Receptors

Molecular cloning has indicated that serotonin (5-hydroxytryptamine, also referred to as 5-HT) receptors belong to at least two protein superfamilies: G-protein-associated receptors which have seven putative transmembrane domains (TMDs) (5-$HT_{1A/B/C/D/E}$, 5-$HT_2$ and rat stomach fundus) and ligand-gated ion channel receptors which have four putative TMDs (5-$HT_3$). Presently, ten distinct mammalian genes encoding G-protein-coupled serotonin receptors have been cloned: five coupled to the inhibition of adenylate cyclase (5-$HT_{1A,1B,1D,1E,1F}$) as described by Albert et al., *J. Biol. Chem.*, 265:5825–5832 (1990), Voigt et al., *EMBO J.*, 10:4017–4023 (1991), Zgombick et al., *Mol. Pharmacol.*, 40:1036–1042 (1991), McAllister et al., *Proc. Natl. Acad. Sci., USA*, 89:5517–5521 (1992), and Amlaiky et al., *J. Biol. Chem.*, 267:19761–19764 (1992), three coupled to phosphotidylinositol-4,5-bisphosphate hydrolysis (5-$HT_{1C,2,2F}$) as described by Julius et al., *Science*, 241:558–564 (1988), Pritchett et al., *EMBO J.*, 7:4135–4140 (1988), and Foguet et al., *EMBO J.*, 11:3481–3487 (1992), and two of unknown coupling (5-$HT_{5A,5B}$) as described Plassat et al., *EMBO J.*, 11:4779–4786 (1992). In addition, the 5-$HT_3$ receptor gene has been cloned, but this receptor belongs to the family of ligand-gated ion channels. Novel G-protein-associated receptors were identified in a polymerase chain reaction (PCR) using degenerate primers corresponding to strongly conserved sequences within their TMDs as described by Libert et al., *Science*, 244:569–572 (1989), the disclosure of which is hereby incorporated by reference.

This strategy has been refined in this invention so as to target novel serotonin-like receptors specifically. The isolation of novel receptors that only bound indoleamine was accomplished by the methods of this invention where two sequential rounds of nested PCR were performed on a rat brain hypothalamic cDNA template. In the second round of PCR, degenerate primers corresponding to conserved residues specific to indoleamine-binding receptors were used to amplify only those receptors. The resulting products were then cloned into pKS pBluescript vectors. Resultant colonies were screened and plasmids from selected colonies were then sequenced. The plasmid fragments were then used to probe a rat hypothalamus cDNA library to obtain full length clones encoding the isolated receptors described in Example 1. The cloning and identification of a novel subfamily of 5-HT receptors of this invention whose members belong to the G-protein-associated superfamily is more fully described below.

A. PCR Amplification

Serotonin receptors were examined as a group to determine whether they contained amino acid sequences that distinguished them from other G protein-coupled receptors. Sequences in TMD V received extra scrutiny because previous site-directed mutagenesis experiments of catecholamine receptors had demonstrated that this region is required for binding the catechol ring structure. See, Strader et al., *FASEB J.*, 3:1825–1832 (1989). The sequences required to bind indoleamine ring structures were surmised to replace catechol-binding sequences in TMD V and that differences between indoleamine and catecholamine-binding sequences could be exploited experimentally to isolate indoleamine binders specifically. In the sequences of all known 5-HT receptors available (5-$HT_{1A}$, 5-$HT_{1C}$ and 5-$HT_2$), a consensus in TMD V existed that differed in 2 positions from catechol-binding receptors.

To test this hypothesis, cDNA was produced from rat hypothalamic mRNA as described below and amplified in two sequential rounds of PCR. The primers in the first PCR round were degenerate, encoding all possible codons of Cys-Ala-Ile-Xaa-Leu-Asp-Arg-Tyr (SEQ ID NO 12) where Xaa is either Ala or Ser in TMD III and the complement of $Xaa_1$-Trp-$Xaa_2$-Pro-Phe-Phe-Ile (SEQ ID NO 13) where $Xaa_1$ was either Cys or Met and $Xaa_2$ was either Leu or Cys in TMD VI. This first round was expected to amplify sequences corresponding to most known catechol and all known serotonin (5-HT) receptors. Amplified PCR products from this reaction were used as the substrate for a second round of PCR with the same 5' primer and a different 3' primer for TMD V, the latter of which was a degenerate complement of all possible codons of Phe-$Xaa_1$-Ala-Phe-$Xaa_2$-Ile-Pro-Leu, (SEQ ID NO 14) where $Xaa_1$ was either Val or Gly and $Xaa_2$ was either Phe or Tyr. This primer pair was expected to amplify sequences corresponding to 5-$HT_{1A}$, 5-$HT_{1C}$, and 5-$HT_2$ receptors, and possibly those of novel 5-HT receptors. For preparing the hypothalamic cDNA, polyadenylated (poly(A)$^+$) RNA was isolated from dissected rat hypothalami using Micro Fast Track kits (Invitrogen, San Diego, Calif.) and used as a template for first strand synthesis of cDNA by Maloney murine leukemia virus (MMLV)-Reverse Transcriptase (Stratagene, La Jolla, Calif.). The resulting cDNAs were then subjected to amplification by PCR with the use of a set of highly degenerate oligonucleotide primers. The first round of PCR on the rat hypothalamus cDNA prepared above was performed using degenerate primers corresponding to conserved regions in TMDs III and VI of both catecholamine and serotonin receptors. Nucleotide sequences of the pool of the 5' end TMD III degenerate oligonucleotide primers used in the first round were 5'-AGCTCCGCGGAGCTCTATGYGCNAT-HGCNYTNGAYMGNTA-3' (SEQ ID NO 15) and 5'-AGCTCCGCGGAGCTCTATGYGCNATHWSNYTNGAYM-GNTA-3' (SEQ ID NO 16), where N was either A, C, G or T; Y was either T or C; H was either T, C or A; M was either A or C; W was either A or T; and S was either C or G. The restriction sites, SacI-SstI, designed into the III degenerate oligonucleotides in tandem for facilitating cloning into pKS pBluescript, are indicated by the underlined nucleotides. Nucleotide sequences of the pool of the 3' end TMD VI degenerate oligonucleotide primers used in the first round were 5'-AGCTCCGCGGAGCTCDATRAARAANGGNA-RCCARCA-3' (SEQ ID NO 17) and 5'-AGCTCCGCGG-AGCTCDATRAARAANGGRCACCACAT-3' (SEQ ID NO 18) where N was either A, C, G or T;.D was either G, A or T; and R was either A or G. The restriction sites, SacI-SstI, designed into the VI degenerate oligonucleotides in tandem for facilitating cloning into pKS pBluescript, are indicated by the underlined nucleotides.

The first PCR amplification was performed for 30 cycles where each cycle consisted of 95° degrees Celsius (94° C.) for 1 minute, 45° C. for 1 minute, and 72° C. for 3 minutes with a Perkin Elmer Cetus 9600 thermal cycler (Perkin Elmer Cetus, Norwalk, Conn.). The reaction mixture was prepared by admixing 10 microliters ($\mu$l) of 10×PCR buffer (Perkin Elmer Cetus), 5 $\mu$l dimethylsulfoxide, 4 $\mu$l of 25 millimolar (mM) deoxynucleotides (dNTP's), 7.5 micrograms ($\mu$g) each of the 5' and 3' pools of oligonucleotide primers, 2.5 u/$\mu$l Taq polymerase (Perkin Elmer Cetus), 2 $\mu$l MgCl$_2$ and water for a final volume of 100 $\mu$l.

The resultant products that exceeded 500 bases were then isolated by agarose gel electrophoresis and used as templates for a second PCR amplification with oligonucleotide primer pools III and V. The 3' end oligonucleotide degenerate primer V corresponded to a conserved region of TMD V, the amino acid residue sequence of which is shown above, specific only for serotonin receptors. The nucleotide sequence of the pool of the V degenerate oligonucleotide primers used in the second round was 5'-ACGTGCGGCCGCNARNGGDATRWARAANGCN-MCRAA-3' (SEQ ID NO 19) where N was either A, C, G or T;.D was either G, A or T; R was either A or G; W was either A or T; and M was either A or C. Adapter sequences on the 5' ends of the primers were designed into the oligonucleotide primers to provide for directional ligation of the resultant doubly-amplified cDNAs into recipient pKs pBluescript vectors. The restriction sites SacI-SstI were built into the oligonucleotide III. The restriction site, NotI, was built into the oligonucleotide V. Thus, the doubly-amplified PCR fragments had SacI-SstI and NotI restriction sites respectively at the 5' and 3' ends of the fragments.

B. Cloning and Sequence Analysis

The products resulting from the PCR amplifications performed in Example 1A were then digested with SacI and NotI for ligation into SacI-NotI linearized plasmid pKs pBluescript vector (Stratagene). The resultant vectors containing the amplified sequences were then used to transform competent DH5 bacteria (BRL, Bethesda, Md.) by the calcium chloride method. A pool of radiolabeled oligonucleotides at 100 nanograms (ng) each diluted in approximately 5 milliliters (ml) of hybridization buffer corresponding to a non-conserved portion of the third intracellular loop for the rat 5-HT$_{1A}$ (nts 1002-976) (5'-TCGGACCCCGACGCGTGCACCATC-3' SEQ ID NO 20), 5-HT$_{1C}$ (nts 879-856) (5'-GTGAATAACACCACGTGCGTGCTC-3' SEQ ID NO 21), and 5-HT$_2$ (nts 1515-1488) (5'-AAGGAGGGGAGCTGCCTGCTTGCC-3 SEQ ID NO 22) receptors to screen approximately 1000 transformed DH5 bacterial colonies. By using the specified pool of oligonucleotide probes for screening the transmembrane domain-specific amplified transformed cells, clones corresponding to these known receptors were successfully eliminated from further consideration. In this negative selection screening protocol, only the clones that failed to hybridize to the pool of nucleotide probed were selected for further cloning, sequencing and characterization.

Two clones, MR22 and MR77, failed to hybridize and were shown to have sequences distinct from one another. All sequencing was performed according to the dideoxy-termination method described by Sanger et al., *Proc. Natl. Acad. Sci., USA*, 74:5463–5467 (1977) and analyzed using Genetics Computer Group sequence software (Madison, Wisc.) as described by Devereux et al., *Nuc. Acids Res.*, 12:387–395 (1984).

The MR22 PCR cDNA clone selected from the screening procedure above was then used to probe an amplified rat hypothalamic cDNA library (4×10$^6$ recombinants in unamplified library) constructed in lambda ZAPII. Of the clones obtained from screening the hypothalamic library, two clones hybridized strongly and six clones hybridized weakly.

The two strongly hybridizing clones had identical inserts of 1905 base pairs (bp), containing an exact match to the original MR22 sequence; thus, the MR22 nomenclature was maintained to identify this clone. The six weakly hybridizing clones had identical inserts of 1511 bp. Because the nucleotide sequence was only 65% identical to that of MR22 and thus distinct, this clone was designated REC17. Anchored PCR (APCR) was performed with dG-tailed hypothalamic cDNAs used as a template in order to obtain full length clones encoding MR22 and REC17. Anchored PCR was performed by first converting poly(A)+-selected RNA extracted from rat brain to first strand cDNA using random hexamer oligonucleotide primers and MMLV-reverse transcriptase. The cDNAs were subsequently tailed with dGTP using terminal transferase. Anchored PCR was performed as described by Frohman et al., *Proc. Natl. Acad. Sci., USA*, 85:8998–9002 (1988) using this dG-tailed cDNA as a template.

For MR22 APCR, a primer complementary to nucleotides 385 to 404 (5'-GGATCCCATGCTTCTGCCGG-3') (SEQ ID NO 23) of the determined MR22 sequence and an anchored primer (5'-GCACCGCGGAGCTCAAGCTTC-CCCCCCCCCCCCCCCCCCCC-3') (SEQ ID NO 24) were used. ACPR was performed as described for PCR above with the exception of the primers listed above and the 10×APCR buffer, the latter of which was prepared by admixing 16.7 ml of 1M (NH$_4$)$_2$SO$_4$, 67 ml of 1M Tris-HCl at pH 8.8, 5 ml of 2% gelatin, 6.7 ml 1M MgCl$_2$ and 4.6 ml water for a total volume of 100 ml. Ten percent of the resulting products were separated by gel electrophoresis and transferred onto nitrocellulose. The nitrocellulose filter was then hybridized with a radioactively labeled oligonucleotide representing nucleotides 320 to 340 of the MR22 sequence listed in SEQ ID NO 1. A major band of approximately 400 bp was detected.

The remaining product was digested with HindIII, separated by electrophoresis, and the 400 bp fragment excised and subcloned into the HindIII site of pKS pBluescript for nucleotide sequence determination. An additional 319 base pairs (bp) of the 5' end of the clone was isolated using this procedure. In composite, the MR22 cDNA (SEQ ID NO 1) is 2226 bp in length and contains an open reading frame (ORF) encoding 370 amino acids beginning 303 nucleotides from the 5' end as shown in FIG. 1. The derived amino acid residue sequence of the MR22 cDNA clone, also shown in FIG. 1, is listed as SEQ ID NO 2.

Figure 2A:
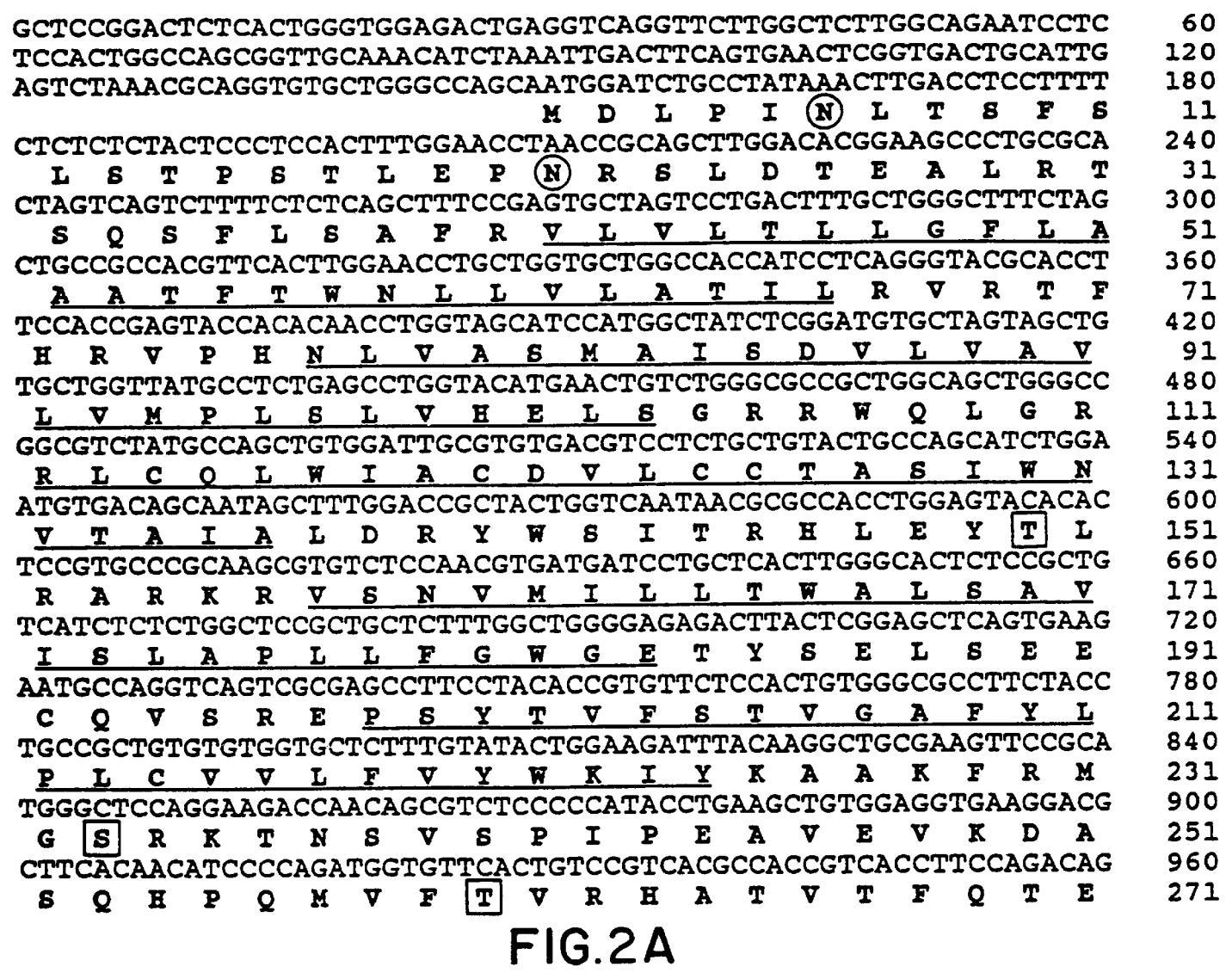

For the REC17 APCR, a primer complementary to nucleotides 626 to 650 of REC17 was used (5'-TGCCCAAGTGAGCAGGATCATCACG-3') (SEQ ID NO 25) and the radiolabeled REC17-specific probe was complementary to nucleotides 562 to 586 (5'-TGGCGCGTTATTGACCAGTAGCGGT-3') (SEQ ID NO 26). A major band of approximately 700 bp hybridized to the labeled probe and was excised, subcloned, and sequenced as described for MR22. Anchored PCR provided an additional 644 bp of sequence. In composite, the REC17 cDNA in SEQ ID NO 3 contains an ORF encoding 357 amino acids as shown in FIG. 2. The amino acid sequences of the putative MR22 (SEQ ID NO 2) and REC17 (SEQ ID NO 4) proteins are 68% identical and can be optimally aligned with 3 gaps.

Thus, by performing the amplification strategies, PCR-derived cDNAs were obtained and used to probe a rat hypothalamus cDNA library (MR22 or REC17) to obtain MR22 and REC17-specific clones spanning the entire coding regions as described above. Based on the determined nucleotide sequence, they were found to putatively encode a protein with the amino acid residue sequence characteristic of the G-protein-coupled, seven-TMD receptor superfamily. Confirmation of the identity and relationship of MR22 and REC17 receptors to known serotonin receptors was accomplished by nucleotide sequence comparison analysis, mRNA distribution and abundance mapping, and protein functional characterization as described in Example 4.

C. Expression

In order to produce recombinant MR22 and REC17 receptor proteins for use in this invention, the MR22 and REC17 cDNAs prepared above were subcloned into the eucaryotic expression vector, pCMV4. The pCMV4 expression vector, obtained from Dr. David Russel, Department of Molecular Genetics, University of Texas, Southwestern Medical Center, Dallas, Tex., was prepared as described by Russel et al., *J. Biol. Chem.*, 264:8222–8229 (1989), the disclosure of which is hereby incorporated by reference. An alternative expression vector for use in expressing the serotonin receptors of this invention is pRc/CMV commercially available from Invitrogen, San Diego, Calif. with the catalog number V750-20. The pRc/CMV expression vector contains enhancer and promoter sequences from the immediate early gene of human cytomegalovirus (CMV) for high level transcription. The vector also contains the ampicillin resistance gene and ColE1 origin for selection and maintenance in *E. coli*.

For subcloning MR22 cDNA into pCMV4, the joining of the two overlapping cDNAs of MR22, which in composite contained the entire coding region, was required prior to subcloning into pCMV4. By using an unique but overlapping restriction site PflMI, these two cDNAs were joined together and subcloned into pKs pBluescript. To subclone into the pCMV4 expression vector, MR22 in pbluescript and pCMV4 were then double digested in parallel with KpnI and XbaI and then the MR22 cDNA containing the entire coding region was directionally ligated into the linearized pCMV4 expression vector to form pCMV4MR22.

For subcloning REC17 into pCMV4, as with MR22, the joining of the two cDNAs representing as a whole the entire coding region of REC17 was required prior to subcloning into pCMV4. This was accomplished with the same procedure as described for MR22. The REC17 complete cDNA in pBluescript was then digested with KpnI and HindIII and directionally ligated into a similarly digested pCMV4 expression vector to form pCMVREC17.

CosM6 cells, a subclonal line of COS-7 cells (American Type Culture Collection (ATCC) accession number 1651, ATCC, Rockville, Md.), or HeLa cells (ATCC accession number CCL2) were then separately transfected with pCMV4MR22 (MR22 cDNA) and pCMVREC17 (REC17 cDNA) prepared above. Also transfected into the host cells were the following control expression vectors: 1) pDP5HT1a, for expressing a known serotonin receptor of subclass $5\text{-}HT_{1a}$ as described by Kobilka et al., *Nature*, 329:75–79 (1987) and 2) pBC12BIBeta2 for expressing a known hamster beta2-adrenergic receptor as described by Kobilka et al., *Proc. Natl. Acad. Sci., USA*, 84:46–50 (1987). The latter gene was cloned into the pBC12BI eucaryotic expression vector (ATCC accession number 67617).

The transfections into the CosM6 cells and HeLa cells were respectively performed by the DEAE dextran and calcium phosphate methods with 10 μg of a selected cesium chloride-purified plasmid per 10 centimeter dish. Alternative cell lines for either transient or stable expression of recombinant serotonin receptor proteins of this invention include NIH3T3 (ATCC accession number CRL1658) (stable), COS-7 (transient), HEK293 (ATCC accession number CRL1573) (stable, Ltk (stable), AV-12 (ATCC accession number CRL9595) (stable), COS-1 (transient), and the like.

Approximately 60 hours after transfection, CosM6 cells were removed from dishes using Versene (Gibco, Gaithersburg, Md.) and a cell scraper, then collected by centrifugation (1,000 rpm for 5 minutes). Pellets were resuspended in 50 mM Tris-HCl, pH 7.6 with a polytron homogenizer, centrifuged (40,000×g for 20 minutes) and resuspended in the same buffer (500 μl/10 cm dish). Once expressed and purified, the recombinant serotonin receptor proteins, MR22 and REC17, were then used in binding assays as described in Example 4D.

2. Preparation of MR77 Isolated Serotonin Receptors

A. PCR Amplification

Highly degenerate oligonucleotides were designed corresponding to conserved amino acid sequences in putative transmembrane domains III, V, and VI of the $5\text{-}HT_{1A}$, $5\text{-}HT_{1C}$, and $5\text{-}HT_2$ receptor. These oligonucleotides were used in sequential polymerase chain reactions (PCR) as described in Example 1A with rat hypothalamus cDNA as the template to generate a series of clones. Complementary DNA was prepared from poly $(A)^+$-enriched RNA as described in Example 1A. Oligonucleotides of degenerate sequence were synthesized corresponding to conserved amino acid sequences of portions of putative transmembrane domains III, V, and VI of the $5\text{-}HT_{1A}$ and $5\text{-}HT_{1C}$ receptors as shown in Example 1A. The two rounds of PCR were performed as described in Example 1A with the same pairs of oligonucleotide primers used in each reaction. The resultant PCR amplification products were then cloned into pBluescript vectors as described below.

B. Cloning and Sequence Analysis

The resulting amplification products prepared in Example 2A were then ligated into pKs pBluescript (Stratagene) and used to transform DH5 bacteria (BRL) as described in Example 1A. Bacterial transformation resulted in approximately 1000 colonies, of which more than 95% hybridized to a mixture of radiolabeled oligonucleotides corresponding to non-conserved regions located between transmembrane domains III and V of the rat 5-HT$_{1A}$ (nts 1002-976) (5'-TCGGACCCCGACGCGTGCACCATC-3' SEQ ID NO 20), 5-HT$_{1C}$ (nts 879-856) (5'-GTGAATAACACCACGTGCGTGCTC-3' SEQ ID NO 21), and 5-HT$_2$ (nts 1515-1488) (5'-AAGGAGGGGAGCTGCCTGCTTGCC-3' SEQ ID NO 22) receptors. Thirty six colonies which showed either minimal or no hybridization were picked, reprobed with the same oligonucleotide mixture, and partial sequences of non-hybridizing clones were determined. From this screening, two distinct cDNA clones were isolated whose sequences had significant similarity to G-protein-associated receptors. One of the cDNA clones, designated MR77, is a novel serotonin receptor-encoding CDNA of this invention.

A rat hypothalamus cDNA library was screened as described in Example 1B with the MR77 cDNA. No clones were obtained in this screen. Since many neurotransmitter receptor genes of this superfamily do not contain introns, it was hypothesized that a genomic clone may contain an intact open reading frame. Thus, a rat genomic library (Stratagene) was probed with radiolabeled MR77 DNA prepared as described for MR22 and REC17 DNA in Example 2B. This screen resulted in the isolation and subsequent subcloning of a 2.5 kb fragment which contained an apparently intronless open reading frame of 1098 nucleotides. However, the reading frame upstream from an apparent initiation codon was also open.

Anchor-PCR protocol was then performed as described in Example 1B with an oligonucleotide primer complementary to nucleotides 311 to 289 (5'-GGCTGGGTGGTGCAGCTTCCG-3') (SEQ ID NO 27) of the determined MR22 sequence and an anchored primer (5'-GCACCGCGGAGCTCAAGCTTCCCCCCCCCCCC-CCCCCCCCC-3') (SEQ NO 24) were used. The template used was dG-tailed rat brain CDNA. The largest product was cloned.

All sequencing was performed according to the dideoxy-termination method as described in Example 1A using Sequenase (United States Biochemical). Sequence data were compiled and analyzed using Genetics Computer Group sequence software (Madison, Wisc.).

The sequence of this partial MR77 cDNA clone shown in FIG. 3 (SEQ ID NO 5) was identical to the genomic clone from nucleotide 97 to 311, but was completely different at its 5' end beginning 41 nucleotides upstream from the presumed initiation codon. The rat MR77 cDNA sequence contained stop codons in frame with the putative coding sequence suggesting that the assignment of the initiation codon was correct. Upon closer examination of the genomic clone, an intron acceptor site was detected at nucleotide 97 as shown in FIG. 3 denoted by the asterisk (*). The sequence shown in FIG. 3 in bold print and listed in SEQ ID NO 6 represents the MR77 cDNA sequence which is different from the genomic clone. The intron lies upstream from the complete open reading frame encoding the putative receptor. Because the open reading frame encoded a 366 amino acid sequence shown in FIG. 3 and SEQ ID NO 7 that is highly related to known receptors throughout its entire length, the mRNA was determined to not contain additional introns.

Human homologs of all of the receptor genes of this invention can be obtained by low stringency hybridization of the rat receptor probes to cDNA or genomic libraries constructed from human tissue. Many libraries are commercially available from companies such as Stratagene, La Jolla, Calif., and Clontech, Palo Alto, Calif.

The MR77 cDNA was used to probe a commercially available human genomic library (Stratagene, catalog #943202). The human library was screened following the same procedure described herein for screening the rat hypothalamus cDNA library. The sequence of the human MR77 homolog was determined which is 86% and 93% identical to rat MR77 at the nucleic acid and amino acid sequence levels, respectively. The human amino acids that differ from those of rat are shown in italics in FIG. 3. The nucleotide and amino acid residue sequences of the human MR77 are respectively listed in SEQ ID NO 8 and 9. The nucleotide sequences of the rat and human clones can be accessed from GenBank, accession numbers are L05596 and L05597, respectively.

Further characterization of the novel MR77 serotonin receptor was determined by comparison of the nucleic and derived protein sequence of MR77 with known serotonin receptors is described in Example 4A. The tissue distribution of the mRNA as described in Example 4B and the comparison with other known serotonin receptors along with the new receptors of this invention are described in Example 4E.

C. Expression

The original subclone of MR77 prepared in Example 2A contained several ATGs in the DNA sequence upstream of the translational start codon. Therefore, to guarantee correct expression of the MR77 protein in eucaryotic cells, the MR77 cDNA subclone contained within the pCMV4 vector needed to be devoid of these upstream DNA sequences. The overall strategy for subcloning was as follows: PCR amplification of the DNA encoding the N-terminal portion of MR77 (from the start codon, ATG to a unique SphI site) was completed using the original MR77 DNA as template. For the amplification via PCR the 5' primer containing the ATG sequence and flanking NotI and HindIII sites was 5'-CAGCTACGGCGGCCGCAAGCTTAAAATGGATT-TTCTAAACTCA-3' (SEQ ID NO 28) and the 3' primer containing the internal unique SphI site was 5'-CTGTTGTAATCGTGATGCCAGCATGC-3' (SEQ ID NO 29).

The resulting PCR products were then double digested in parallel with the original MR77 clone which was cloned in pBluescript as described in Example 1B. The digested PCR products were subcloned into the digested and linearized MR77-containing pBluescript vector, thus replacing the original MR77 5' end and subsequently the upstream and undesirable ATGs. This new MR77 subclone was then double digested with HindIII and SmaI and directionally ligated into a similarly digested pCMV4 expression vector prepared as described in Example 1B. The resultant expression vector, designated pCMV4MR77, contained the entire coding region of MR77.

The recombinant MR77 serotonin receptor protein was expressed as described for MR22 and REC17 proteins in Example 1C. The MR77 protein was then used in binding assays as described in Example 4D to confirm the specificity of the novel receptor.

3. Preparation of REC20 Isolated Serotonin Receptors

In order to gain an understanding of the role of serotonin in circadian rhythms and hypothalamic function, a paradigm targeted for discovering new serotonin and indoleamine receptors, such as melatonin which is also thought to modulate endogenous clock function, was designed. In an attempt to identify more receptors which belong to the recently characterized family of 5-HT$_5$ receptors, a PCR strategy similar to those previously described in Examples 1 and 2 was designed as described below.

A. PCR Amplification

For isolating the novel REC20 serotonin receptor of this invention, a different amplification procedure was designed than that used to amplify MR22, REC17 and MR77 as described in Examples 1 and 2. As will be described herein, degenerate primers corresponding to regions of TMD III and TMD VII that are conserved among catecholamine and serotonin receptors, were used in the first round of PCR. Then, the second round of PCR was performed using a degenerate primer corresponding to residue in TMD V specific to MR22 and REC17 in conjunction with the previously used TMD VII primer.

The two step PCR amplification procedure was performed as described in Example 1A with a few modifications. Oligonucleotides of degenerate sequence where synthesized corresponding to conserved transmembrane domains (TMD) III and VII of known serotonin receptors. The amino acid sequence of domain III along with the nucleotide sequence of the degenerate oligonucleotide primer pool for amplifying this region is described in Example 1A. The amino acid sequence of the TMD VII is Trp-Xaa$_1$-Gly-Tyr-Xaa$_2$-Asn-Ser-Xaa$_3$ (SEQ ID NO 30) where Xaa$_1$ was either Leu or Ile, Xaa$_2$ was either Leu or Ser and Xaa$_3$ was either Leu or Phe. The degenerate 3' oligonucleotide primer pool for amplifying the TMD VII region has the nucleotide sequence 5'-GCTCATCTAGANARNSWRTTNVDRTANCCNAD-CCA-3' (SEQ ID NO 31), where N was either A, C, G or T, R was either A or G, S was either G or C, W was either A or T, V was either A, G or C, and D was either A, G or T. The underlined nucleotides indicate an XbaI restriction site to facilitate the directional cloning of the amplified products.

These oligonucleotides were used to amplify rat brain cDNA as described in Example 1A. The template included cDNA from whole brain, hypothalamus, hippocampus, and cerebral cortex. The products of this reaction were then used as template in a second reaction with the same TM VII oligonucleotide shown above, but with the 5' degenerate oligonucleotide primer pool corresponding to a region downstream of TMD V, conserved only between the 5-HT$_{5A}$ and 5-HT$_{5B}$ receptors having the amino acid residue sequence Phe-Val-Tyr-Trp-Lys-Ile-Tyr-Lys (SEQ ID NO 32). The V degenerate oligonucleotide pool was derived from the nucleotide sequence 5'-CTGGTGGTCGACGG-TACCTTYGTNTAYTGGAARATHAYAA-3', (SEQ ID NO 33) where N was either A, C, G or T, Y was either T or C, R was either A or G and H was either T, C or A. The TMD V degenerate oligonucleotide contained tandemly arranged restriction endonuclease sites, SalI-KpnI, at the 5' end of the primer as indicated by the underlined nucleotides. The second set of primers were highly degenerate in sequence, but corresponded to regions conserved only in the identified 5-HT$_{5A}$ and 5-HT$_{5B}$ receptor genes described in Example 1, respectively REC17 and MR22.

The second round of PCR amplification with the V and VII oligonucleotide primer pools with the first PCR amplification products as a template was performed as described in Example 1A. The resultant PCR amplification products contained the restriction sites, SalI-KpnI and XbaI, respectively at the 5' and 3' ends to allow for directional ligation into pBluescript as described in Example 3B.

B. Cloning and Sequence Analysis

The products of the second PCR amplification prepared above were subcloned into pBluescript (Stratagene) and used to transform DH5 cells (BRL) as described in Example 1B. The resultant colonies were probed with a mixture a radiolabeled oligonucleotides that were 20 nucleotides in length specific to 5-HT$_{5A}$ and 5-HT$_{5B}$ receptors. The probes used in the screening had the following nucleotide sequences: 5'-CCTCAGGAGTCTGAGACGGTATTC-3' (SEQ ID NO 34) and 5'-GCTGTGGAGGTGAAGGACGTTCAC-3' (SEQ ID NO 35). Negative selection was performed as described in Example 1B. The two colonies which did not hybridize were picked, grown, and the sequence of the plasmid inserts determined. One of these fragments, number 20, was radiolabeled and used to then screen a rat hypothalamus cDNA library also as described in Example 1B. Positive clones were purified, digested with EcoRI, subcloned, and their sequence determined according to the dideoxy-termination method as described in Example 1B using Sequenase (USB, Cleveland, Ohio).

Thus, this PCR amplification strategy and screening resulted in the selection of a novel serotonin receptor designated REC20. The nucleotide and derived amino acid sequence of REC20, shown in FIG. 5, are listed respectively in SEQ ID NO 10 and 11. The 5-HT$_6$ receptor cDNA, isolated from a rat hypothalamus library, encodes a putative protein of 435 amino acids and has seven predicted transmembrane domains. Primary sequence analysis indicates that 5-HT$_6$ represents a new class of 5-HT receptors within the G-protein coupled family. Additional characterization of the REC20 based on nucleotide sequence and amino acid sequence is also described in Examples 4A and 4E. The recombinant REC20 receptor protein was expressed as described below.

The human homologs of REC20 was also isolated from screening a human genomic library obtained from Stratagene with the REC20 cDNA clone as a probe as described in Example 2B for MR77.

C. Expression

The initial clone of REC20 was 3.6 kb. A 2 kb fragment of the 3.6 kb clone was subcloned into the EcoRI site of pBluescript (Stratagene). A fragment containing most of the coding sequence (minus the first 122 nucleotides of the coding sequence) with digested with SacI, blunt-ended this fragment, and ligated into pCMV4, prepared in Example 1C, which had been predigested with SmaI and treated with phosphatase. The resultant plasmid vector containing the insert was designated pCMV4-20. A new fragment containing the first 122 nucleotides, starting with the initiator, ATG, was PCR amplified using an oligonucleotide containing the ATG (preceded by a restriction endonuclease site for HindIII) and an oligonucleotide corresponding to the reverse complement of nucleotides 1568–592 of the original 2 kb clone. This fragment was digested with HindIII and NheI and ligated into pCMV4-20 which had been similarly digested. The resulting clone was sequence-confirmed. All sequencing was performed according to the dideoxy-termination method as described in Example 1A using Sequenase (United States Biochemical). Sequence data were compiled and analyzed using Genetics Computer Group sequence software (Madison, Wisc.). The REC20 recombinant protein was then used for binding assays as described in Example 4D.

4. Characterization of Expressed Novel Serotonin Receptors

A. Nucleotide and Protein Sequence Comparison

1) MR22 and REC17

Both MR22 and REC17 contain seven putative membrane spanning regions, and putative N-glycosylation and phosphorylation sites in positions similar to known receptors as shown in FIGS. 1 and 2, consistent with the hypothesis that these two proteins belong to the G-protein-associated receptor superfamily. A search of the protein and nucleic acid databases with the entire MR22 putative protein sequence revealed the greatest amino acid sequence identities in the 30–35% range to alpha- and beta-adrenergic and 5-HT receptors from various species. REC17 yielded very similar results.

Comparison of only the putative TMD regions of MR22 and REC17 with TMDs of other known G-protein-associated receptors gave qualitatively similar results, although the identities were in the 40–48% range, with none exhibiting dominant similarity. Thus, MR22 and REC17 are probable G-protein-associated receptors much more related to one another than to known receptors for various ligands. Consequently, sequence analysis did not provide the identity of the endogenous ligands interacting with MR22 and REC17.

2) MR77

The MR77 protein sequence predicted from the CDNA clone contains seven hydrophobic regions as determined by hydropathy calculations performed as described by Kyte et al, *J. Mol. Biol.*, 157:105–132 (1982). In addition, the N-terminal putative extracellular domain has two potential sites for asparagine-linked glycosylation at amino acids five and ten as shown by the arrows in FIG. 3. There are several potential protein kinase C (circles) and calmodulin kinase II phosphorylation (squares) sites in the large intracellular loop between putative transmembrane domains V and VI as shown in FIG. 3. These potential post-translational modifications are similar to those predicted for a variety of G-protein-coupled receptors. See, Savarese et al., *Biochem. J.*, 283:1–19 (1992) and Rands et al., *J. Biol. Chem.*, 265:10759–10764 (1990).

MR77 exhibits considerable amino acid homology, particularly within the transmembrane domains, with known 5-HT receptors that are coupled to the inhibition of adenylate cyclase: human S31 (5-HT$_{1E}$), dog 5-HT$_{1D}$, rat 5-HT$_{1B}$, rat 5-HT$_{1A}$, and rat 5-HT$_{1C}$ with 55%, 48%, 46%, 35%, and 30% overall identity. The primary amino acid sequence of MR77 is most closely related to the recently described human S31 receptor described by Levy et al., *FEBS Lett.*, 296:201–206 (1992) which has been identified as the 5-HT$_{1E}$ receptor as described by McAllister et al., *Proc. Natl. Acad. Sci., USA*, 89:5517–5521 (1992).

3) REC20

As described in Example 3B, the REC20 clone obtained from using a unique PCR amplification and screening strategy was 3.1 kb in length and had an open reading frame encoding a putative protein of 435 amino acids as shown in FIG. 5. Hydrophobicity analysis of the REC20 amino acid sequence predicted the presence of seven major membrane spanning domains. In addition, the receptor encoded by REC20 contains potential sites for N-linked glycosylation, protein kinase C phosphorylation, and cAMP-dependent phosphorylation. REC20 also has transmembrane-specific amino acid residues conserved among all biogenic amine receptors (Asp164, Pro254, Tyr262, Phe339, Trp343, Pro345, Trp374, Asn383, Pro384) as described by Trumpp-Kallmeyer et al., *J. Med. Chem.*, 35:3448–3462 (1992).

REC20 exhibited highest identity, within the conserved transmembrane domains, with the Drosophila 5-HTdrol receptor (54%) as described by Witz et al., *Proc. Natl. Acad. Sci., USA*, 87:8940–8944 (1990). However, the entire REC20 sequence did not exhibit preferential identity to any known 5-HT receptor subgroup (5-HTdrol, 39%; 5-HT$_{1D}$, 39%; 5-HT$_{1A}$, 37%; 5-HT$_{1E}$, 39%; 5-HT$_5$, 33%) and is therefore classified as a novel 5-HT receptor, 5-HT$_6$. The 5-HT$_6$ nomenclature has previously been given to a novel mouse receptor as described by Amlaiky et al., *J. Biol. Chem.*, 267:19761–19764 (1992).

B. Northern Analysis and Semi-Quantitative PCR

1) MR22 and REC17

MR22 and REC17 cDNAs were hybridized to blots containing RNA from rat brain regions and heart, liver and kidney to determine the tissue distribution of the mRNA encoding the respective serotonin receptors. To perform Northern analysis, total RNA was first isolated from frozen tissues of adult Sprague-Dawley rats by extraction with guanidinium isothiocyanate as described by Chirgwin et al., *Biochem.*, 18:5294–5299 (1979). Oligo(dT)-cellulose chromatography, performed as described by Aviv et al., *Proc. Natl. Acad. Sci., USA*, 69:1408–1412 (1972) was used to enrich for poly(A)$^+$ RNA. For RNA blots, 10 μg poly(A)$^+$ RNA was loaded per lane, except 1.5 μg for the medulla sample, and was subsequently resolved by electrophoresis on a 1.2% agarose—1.2M formaldehyde gel, transferred to nitrocellulose membrane and hybridized to either $^{32}$P-labeled MR22 cDNA (entire insert) or the 3' untranslated region of REC17 (nucleotides 1200 to 1719). To confirm that similar amounts of intact RNA were loaded in each gel lane, blots were stripped and hybridized with a [$^{32}$P]-cDNA probe for ubiquitously expressed cyclophilin mRNA as described by Danielson et al., *DNA*, 7:261–267 (1988).

Detection of RNAs with either MR22 or REC17 cDNAs prepared in Example 1 required 2–3 week exposures with 5 μg poly(A)$^+$-enriched RNA samples. MR22 cDNA hybridized to three distinct RNAs with the approximate sizes of 1.5, 1.8 and 3.0 kilobases (kb) that were detectable only in the hippocampal tissue sample. Given that the originally isolated MR22 PCR cDNA and the subsequent cDNA clone was obtained from a hypothalamus CDNA library, the hybridization to only hippocampal mRNA was unexpected. The probable explanation is that MR22 is expressed in the hypothalamus but at a level below detection by RNA blots; this is consistent with the isolation of only one distinct MR22 cDNA clone from a hypothalamic cDNA library containing more than 106 recombinants. In contrast, REC17 detected RNA species with the approximate sizes of 3.8 and 4.5 kb in most regions of rat brain, with highest concentrations in hippocampus and hypothalamus, and lower concentrations in cortex, thalamus, pons, striatum and medulla. Neither MR22 nor REC17 mRNAs were detectable in heart, kidney and liver. The tissue distribution of MR22 and REC17 is compared with the other serotonin receptors of this invention in Table 1 below.

2) MR77

The tissue distribution of MR77 expression could not be determined by Northern blotting because of the low expression of the mRNA. However, with the use of PCR and the fact that the MR77 gene contained an intron in its 5' untranslated region, semi-quantitative PCR could be performed to obtain tissue distribution information on MR77. Primers were designed so as to amplify MR77, producing a 563 base pair fragment from cDNA templates, but not from genomic DNA, as shown in FIG. 4A.

For this semi-quantitative PCR assay, two oligonucleotide primers were designed: one was the inverse complement of nucleotides 590–615 of MR77 cDNA (SEQ ID NO 1) and the other corresponded to the region of the cDNA 20 nucleotides upstream from the putative splice site. In a PCR assay, these primers amplify a 563 bp fragment from cDNA template, but not from genomic DNA. dissected rat tissues including several brain regions. First strand cDNA was synthesized from 1 μg of poly A$^+$RNA from each tissue using MMLV-Reverse Transcriptase. Two μl of a ¹⁄₁₀ dilution of each cDNA was used as template in a PCR reaction performed as described in Example 1A using the above described primers for 30 amplification cycles. Thirty cycles were determined to be within the linear amplification range under the conditions used. Equal aliquots (10 μl) of each PCR reaction were subjected to agarose gel electrophoresis. The resulting gel was denatured, neutralized, transferred to nitrocellulose membrane, and probed with a radiolabeled oligonucleotide complementary to nucleotides 364–385 of the MR77 cDNA clone (SEQ ID NO 1), corresponding to nucleotides 257–278 of the genomic clone.

Figure 4B:
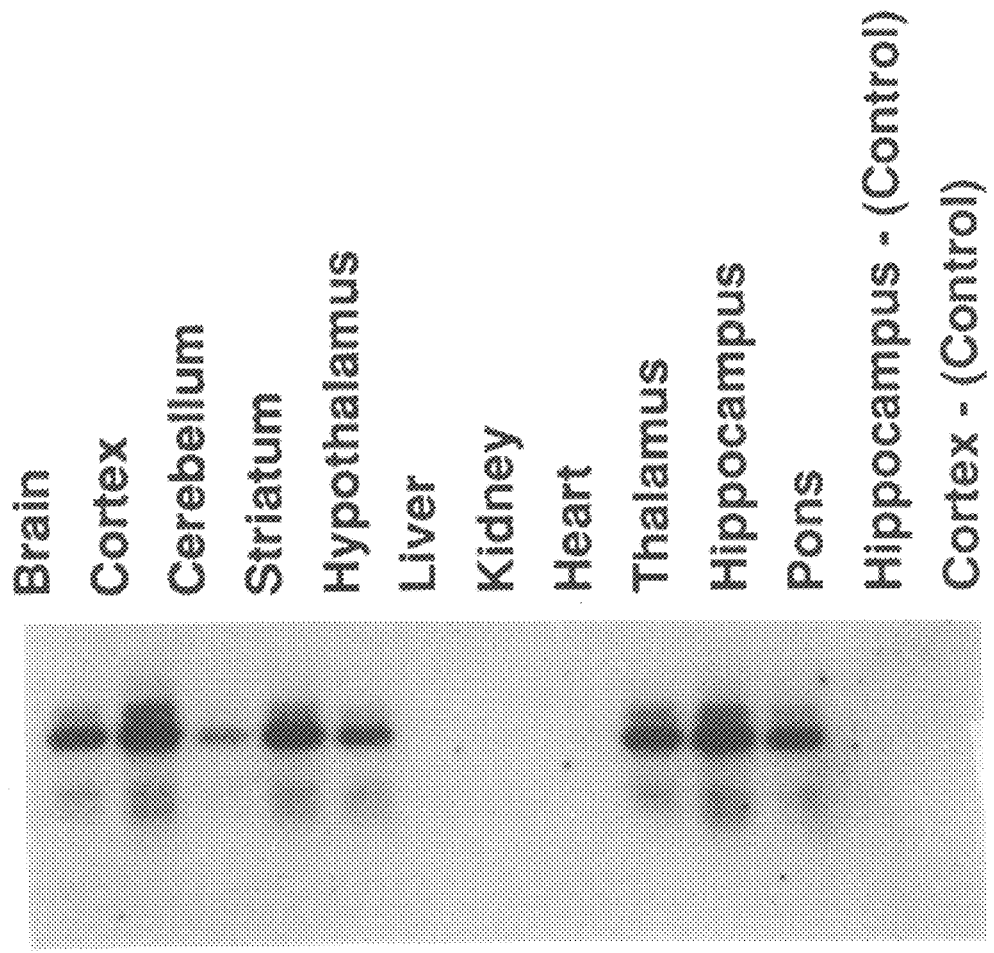
In FIG. 4B, the regional distribution of MR77 mRNA expression is shown. cDNAs from the tissues listed were used as templates for the PCR reaction described above (A). The major band (middle band) migrates at approximately 570 base pairs. The blot was probed with an $^{32}P$-labeled oligonucleotide corresponding to nucleotides 257–278 of the genomic clone. The control lanes 12 and 13 used mRNA templates that had not been reverse transcribed.

Therefore, detection of the amplified products were expected to be diagnostic for the presence of MR77 mRNA. Equal amounts of cDNA made from mRNA extracted from a variety of rat tissues were subjected to PCR and a major band migrating at approximately 570 base pairs was observed with some templates as shown in FIG. 4B. The 570 bp PCR product was subcloned and its sequence was shown to be identical to the appropriate region of the MR77 cDNA. The MR77 PCR product was detected in approximately the following abundance: cortex=striatum= hippocampus>thalamus =pons>hypothalamus>cerebellum. The tissue distribution of MR77 is compared with the other serotonin receptors of this invention in Table 1 below.

This distribution is consistent with known central nervous system terminal fields for serotonergic pathways. The abundance of MR77 mRNA in the cerebral cortex was estimated to be approximately 0.0001% of total mRNA, based on the comparison of the PCR product formed from cortex CDNA template to the product formed from known amounts of cloned MR77 DNA template. No PCR product was detected with liver, kidney, or heart cDNA templates. To show that the PCR products were not the result of amplification of genomic DNA, the same hippocampus and cortex mRNAs that were used to make cDNA template were additionally used as templates here but had not been reverse transcribed in this instance in PCR. These reactions did not yield any products as shown in lanes 12 and 13 in FIG. 4B.

3) REC20

The anatomical distribution of REC20 mRNA expression in rat brain was determined by northern blot analysis with the REC20 clone performed as described in Example 4B1). The results that showed selective REC20 mRNA expression in the hypothalamus, thalamus, hippocampus, cortex, pons, and medulla. No mRNA expression was detected in the cerebellum, striatum, or peripheral tissues such as heart, liver, kidney, adrenal glands, testes, ovaries, or spleen. The tissue distribution of REC20 is compared with the other serotonin receptors of this invention in Table 1 below.

C. Localization of mRNA Encoding Serotonin Receptors by In Situ Hybridization

1) MR22 and REC17

In-situ hybridization studies were performed to determine the cellular location of MR22 mRNAs within rat brain using a sensitive method as described by Strader et al., *FASEB J.*, 3:1825–1832 ((1989), the disclosure of which is hereby incorporated by reference. Free floating in situ hybridization was performed as adapted from Gallet al., *Science*, 245:758–761 (1989). Coronal sections, 25 μm thick, from 4 young adult Sprague Dawley rats were hybridized at 55° C. for 16 hours with $1.5 \times 10^7$ cpm/ml of $^{35}$S-labeled single-stranded RNA probes. Free floating sections were then digested with 4 μg/ml of RNase A in 50 mM Tris-HCl, 0.5M NaCl, 1 mM EDTA (pH 7.5) for 1 hour at 37° C. Washes were performed in 50% formamide-0.5×SSC containing 14 mM beta-mercaptoethanol at 60° C. for three hours. Further washes were carried out in 0.1×SSC-0.5% N-lauryl-sarkosinate at 68° C. for 1 hour. Sections were mounted on coated slides, dehydrated and exposed to Kodak XAR films for 5 days at room temperature. Autoradiography was performed by dipping slides in Ilford K4 emulsion diluted 1:1 with water, and exposing them with desiccant at 4° C. for 5 weeks. Slides were developed in Kodak D19, counterstained and mounted in Permount.

The most intense hybridization was detected in the hippocampus, medial and lateral habenular nuclei and raphe. Within the hippocampus, MR22 mRNA was exclusively detected in CA1 region and subiculum; within CA1, MR22 hybridization was most prominent over the pyramidal layer. Very low silver grain densities, just above background, were found in piriform cortex and supraoptic nucleus of hypothalamus. Thus, the cellular localization of MR22 mRNA is consistent with the Northern blot data described in Example 1B. The preliminary in situ hybridization data for REC17 is also consistent with the Northern blot data; REC17 mRNAs were detectable in many regions of the rat CNS (piriform cortex, hippocampus, amygdala, septum, and several thalamic nuclei.

The ventral ascending serotonergic pathway originating from the mesencephalic raphe nuclei innervates a number of rostral structures including the medial habenula and hippocampus, but also including the hypothalamus, amygdala and several cortical regions. The significance of the observation that MR22 mRNAs in the hippocampus were mostly restricted to CA1 is unclear, although the rat 5-HT$_{1B}$ receptor, which is expressed in many areas of the brain, appears to be restricted in the hippocampus to synaptic terminals of CA1 efferents. See, Voigt et al., *EMBO J.*, 10:4017–4023 (1991). The tissue distribution of MR22 and REC17 is compared with the other serotonin receptors of this invention in Table 1 below.

2) REC20

To define the cellular distribution of REC20, the mRNA expression by in situ hybridization in rat brain slices was performed as described in Example 4C1). Expression was clearly noted in the thalamus, particularly in the ventrolateral, ventromedial, anteroventral, mediodorsal, and paraventricular thalamic nuclei. Hybridization was also detected in the hippocampus, predominantly in the CA3 region, the subicular complex, and the medial septal nuclei. Moderate expression was found in the anterior, lateral, and ventromedial hypothalamic nuclei. Hybridization was also found in the suprachiasmatic nuclei of the anterior hypothalamus. In addition, REC20 mRNA was detectable in the piriform and cingulate cortices, as well as layers II and III of the neocortex. No hybridization was detected in the midbrain raphe nuclei.

Thus, northern blot and in situ hybridization studies demonstrated 5-HT$_6$ REC20 mRNA expression in the thalamus, hypothalamus, cortex, pons, and hippocampus, but not in the cerebellum, heart, liver, or kidney.

The comparison of the tissue distribution of the four novel serotonin receptor proteins of this invention is summarized in Table 1.

TABLE 1

| Region | Rec20 | MR77 | MR22 | Rec17 |
|---|---|---|---|---|
| Cortex | Yes | Yes | No | Yes |
| Amygdala | No | No | No | Yes |
| Hippocampus | Yes | Yes | Yes | Yes |
| Septum | Yes | nd | No | Yes |
| Thalamus | Yes | Yes | No | No |

TABLE 1-continued

| Region | Rec20 | MR77 | MR22 | Rec17 |
| --- | --- | --- | --- | --- |
| Hypothalamus | Yes | Yes | No | No |
| Raphe Nuclei | No | nd | Yes | nd |
| Cerebellum | No | No | No | No |
| Heart | No | No | No | No |
| Liver | No | No | No | No |
| Kidney | No | No | No | No | nd = not determined

D. LSD Binding Assays for Determining the Specificity of MR22, REC17, MR77 and REC20 Serotonin Receptors To determine the ligand(s) for MR22, REC17, MR77 and REC20 empirically, the four cDNAs were separately transfected into a eucaryotic expression vector (pCMV4) and transiently transfected CosM6 cells as described in Examples 1C, 2C and 3C. For the [$^{125}$I]-LSD binding assays, after the expressed proteins were purified and resuspended, [$^{125}$I]-LSD (NEN, 2200 Ci/mmol) binding was assessed in a 100 µl final volume and contained 0.02% ascorbate, CosM6 membranes (15 µg protein), [$^{125}$I]-LSD (final concentration, 1 nM), and various unlabeled test compounds identified in Table 2. Nonspecific binding was determined using 100 micromolar (µM) serotonin and typically was less than 10% of total disintegrations per minute (dpm). Following 60 minutes at 37° C., 2 ml of ice-cold 50 mM Tris-HCl were added to each tube and bound ligand was isolated on 0.1% polyethyleneimine-soaked GF/B glass fiber filters, washed twice, and counted for radioactivity. Protein concentration was measured using the Bradford dye binding method (BioRad, Richmond, Calif.). Binding data was analyzed using non-linear regression analysis.

When tested in the above assay, broken cell preparations from transfected cells, that have expressed either MR22, REC17, MR77 and REC20 recombinant serotonin receptor proteins, exhibited saturable binding for [$^{125}$I]-LSD, a non-selective serotonergic ligand.

To relate each of the serotonin receptors to known members of the 5-HT receptor family, the ability of selective 5-HT agonists and antagonists were measured for their ability to displace LSD from the membrane preparations. The assays measuring IC50 values for competition with $^{125}$I·LSD (nM) were performed as described above and the data is summarized in Table 2 below.

TABLE 2

| Ligand | Rec20 | MR77 | MR22 | Rec17 |
| --- | --- | --- | --- | --- |
| 8-OH-DPAT | 97 | >1000 | >1000 | >1000 |
| 5-CT | 0.8 | >1000 | 285 | 20.4 |
| Methysergide | 32 | 14 | >1000 | 310 |
| Ergotamine | 33 | 55 | 22 | 10 |
| Metergoline | 17 | 535 | >1000 | >1000 |
| Mesulergine | 17 | >1000 | >1000 | >1000 |
| 5-HT | 9 | 70 | 1613 | 380 |
| Methiothepin | 1.3 | >1000 | 176 | 45 |
| Sumatriptan | >1000 | 67 | >1000 | >1000 |
| Ritanserin | 60 | — | — | — |
| Clozapine | 48 | — | — | — |
| Yohimbine | >1000 | 570 | >1000 | >1000 |
| Pindolol | >1000 | — | — | — |

The binding of radiolabeled LSD to MR77 is sensitive to sumatriptan, a 5-HT$_{1D}$ agonist, but insensitive to 5-carboxyamidotryptamine (5-CT), a mixed 5-HT$_{1A/1D}$ agonist, and 8-OH-DPAT, a 5-HT$_{1A}$ agonist. The pharmacological profile of MR77 is similar to that of the 5-HT$_{1E}$ receptor. MR22 and REC17 have similar pharmacological profiles which do no readily fit to any pharmacologically defined 5-HT receptors which have been previously described. Both receptors are sensitive to ergotamine, 5-CT and methiothepin but insensitive to sumatriptan and 8-OH DPAT. REC20 has a pharmacological profile that is unique in that the binding of radiolabeled LSD is displace by 5-HT$_{1A}$ agonists 8-OH DPAT and 5-CT but is also sensitive to the 5-HT$_2$ antagonist ketanserin.

These pharmacological profiles in conjunction with the amino acid residue sequence as described below allows for the classification of the four novel serotonin receptors of this invention into three new subfamilies of the serotonin receptor family.

E. Dendrogram Classification of the Novel Serotonin Receptor Proteins Based on Amino Acid Residue Sequence Historically, the classification of serotonin receptors (5-HT) has been based on their pharmacological properties as reviewed in Frazer et al., *Ann. Rev. Pharmacol. Toxicol.*, 30:307–348 (1990). Thus, 5-HT$_1$-like receptors have been classified as (i) potently antagonized by methiothepin and/or methysergide, (ii) not antagonized by molecules binding specifically to 5-HT$_2$, and (iii) potent agonism to 5-CT (greater than or equal to 5-HT). See, Bradley et al., *Neuropharm.*, 25:563–576 (1986). With the advent of molecular cloning of 5-HT receptors, their classification has changed from being based purely on pharmacological criteria to a more structurally based definition. Hartig, *TIPS*, 10:64–69 (1989) and Peroutka, *Neuropharm.*, 31:609–613 (1992) have suggested that the receptor nomenclature for 5HT receptors be primarily based on amino acid sequence. The use of primary structure to catalogue 5-HT receptors is appropriate as it allows for an absolute identification of each 5-HT receptor.

Figure 6:
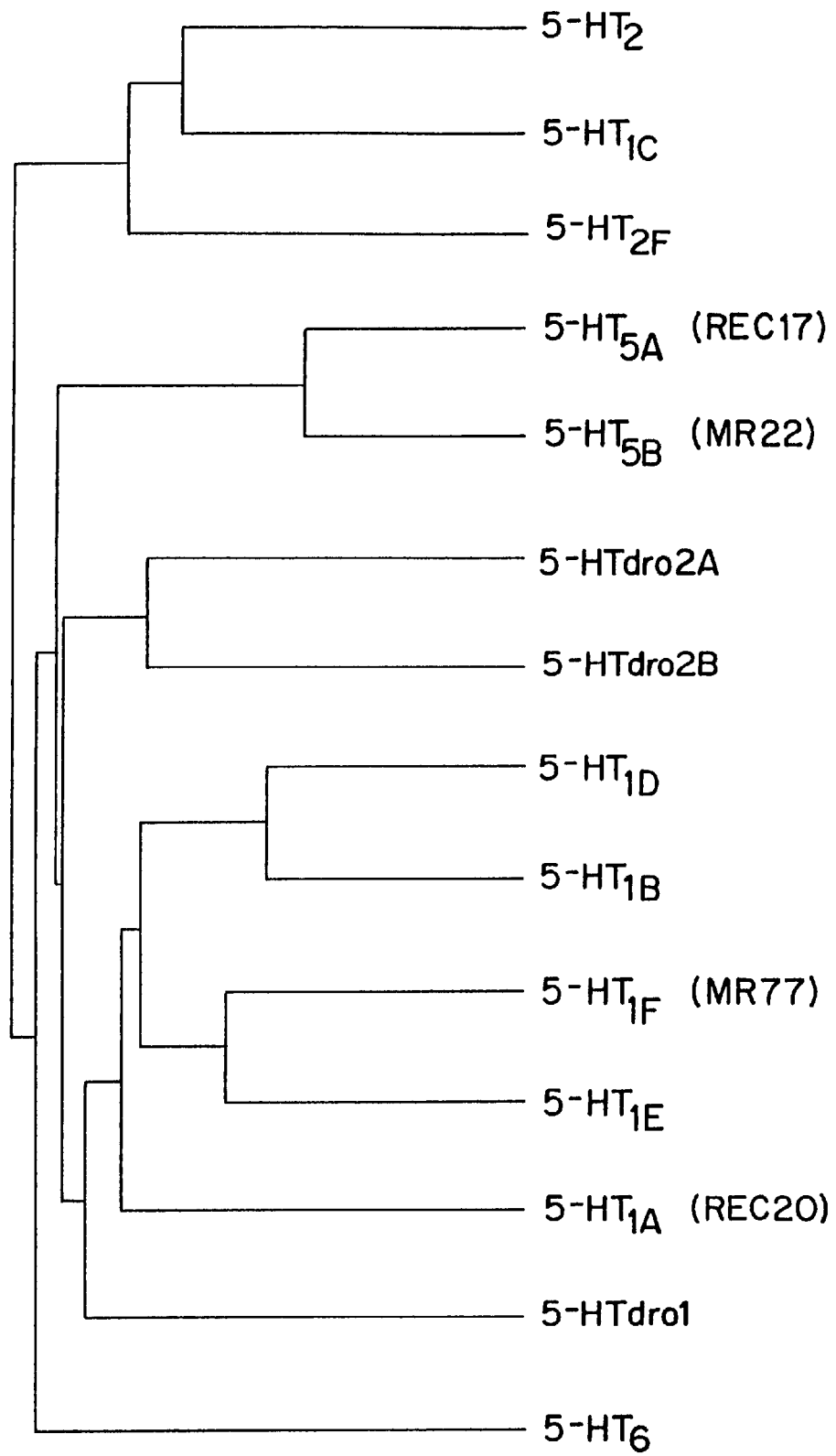
FIG. 6 illustrates the dendrogram analysis of serotonin G-protein coupled receptor family. This figure demonstrates how subgroups of serotonin (5-HT) receptors including the four novel serotonin receptor proteins of this invention cluster according to sequence similarity. The length of the horizontal line is inversely proportional to primary structure identity between the sequence pairs. Species from which primary structure are derived is as follows: $5-HT_{1A,B,C,2}$ are rat, $5-HT_{1E}$ is human and $5-HT_{1D}$ is canine. The Drosophila 5-HTdro1, dro2A, dro2B receptors were included to show sequence relationships. The amino acid sequence data used in generating the dendrogram were compiled and analyzed using the Genetics Computer Group sequence software Lineup and Pileup (Madison, Wisc.). The dendrogram placement of the novel serotonin receptor proteins of this invention, MR22, REC17, MR77 and REC20, is discussed in Example 4E.
Figure 7A:
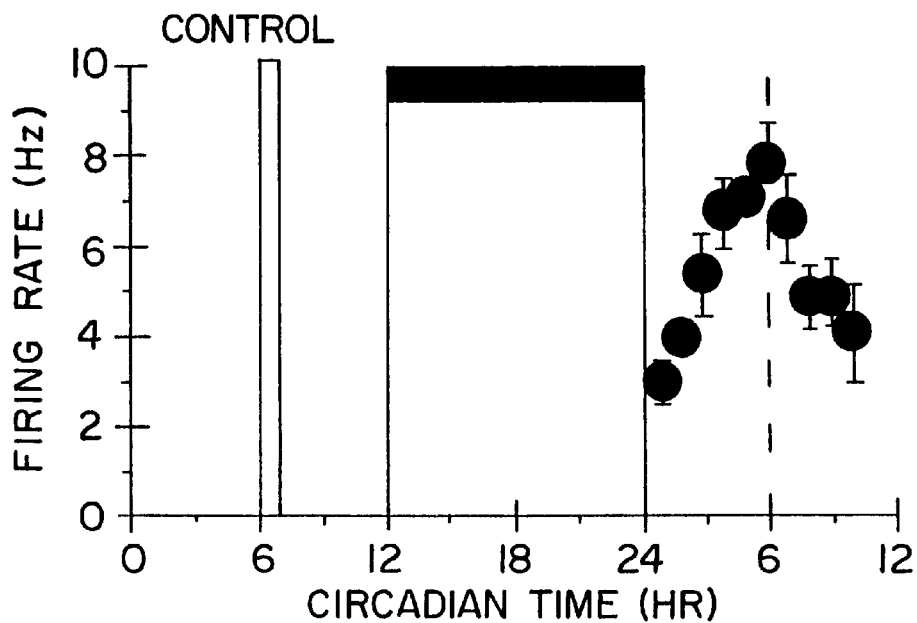
FIG. 7A–D illustrates the effects of serotonergic agents on the neuronal activity as measured against circadian time in the suprachiasmatic nucleus (SCN) as described in Example 7. The procedures used in measuring the circadian time involving slice preparation and maintenance, electrophysiological recordings, and data analysis were performed as described by Prosser et al., *J. Neurosci.*, 9:1073–1081 (1989). Slice treatment consisted of stopping perfusion and replacing bath medium for 1 hour with medium containing no additional compounds (=control) or 8-OH-DPAT. In blocking experiments, bath medium was first replaced for 15 minutes with perfusion medium containing either pindolol or ritanserin (dissolved in 100% ethanol and then diluted to the proper concentration), followed by replacement for 1 hour with medium containing 8-OH-DPAT and either pindolol or ritanserin, followed by an additional 15 minute treatment with medium containing pindolol or ritanserin. This was followed by the normal perfusion medium. Horizontal bars: time of lights-off in donor colony; vertical bars: time of treatment; dotted line: mean time of peak in untreated slices.
Figure 7B:
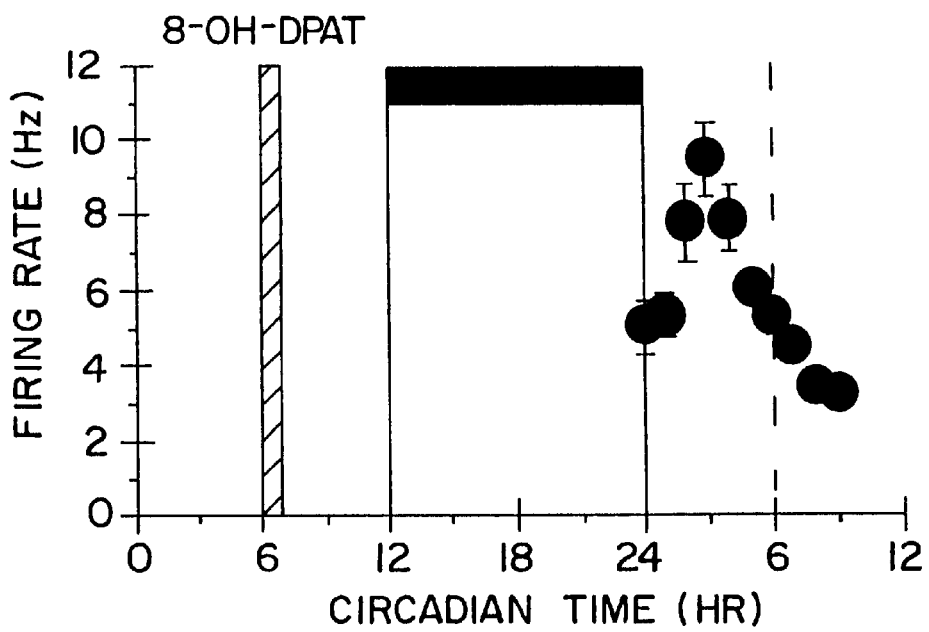
Figure 7C:
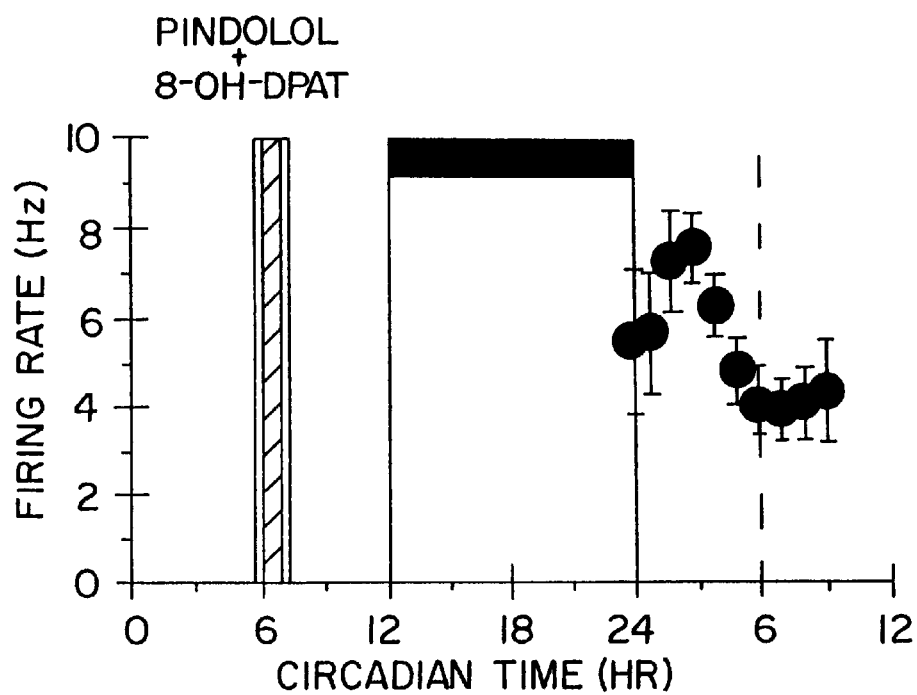
Figure 7D:
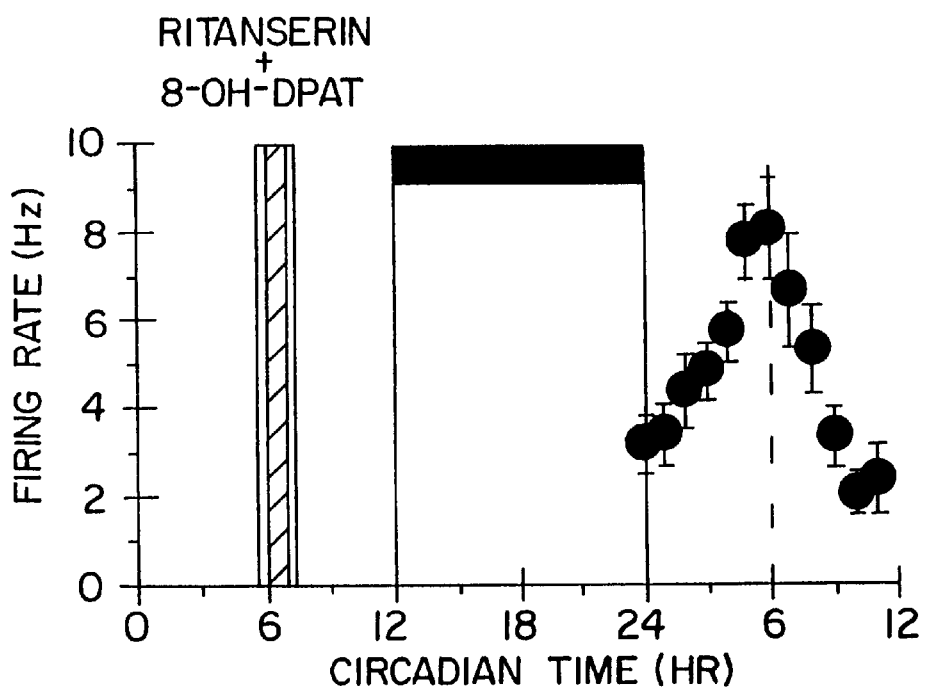

The relationships among the known G-protein coupled serotonin receptors is graphically illustrated as a dendrogram as shown in FIG. 6. The dendrogram mapping of the novel serotonin receptors of this invention are described below.

1) MR22 and REC17

Two of the four novel serotonin receptors of this invention, MR22 and REC17, have no greater sequence identity to the known 5-HT receptors than to other previously cloned cationic binding receptors. The amino acid sequences of REC17 and MR22 were compared to all known 5-HT receptors, using the program PILEUP (GCG, Univ. of Wisconsin) which ranked (by pairwise sequence identity) each receptor in relation to the others being examined. When the relationships were plotted as a dendrogram as shown in FIG. 6, in which sequence identity is inversely proportional to the length of the horizontal line, REC17 and MR22 were seen to form a distinct subfamily between that of the 5HT$_1$-like (5HT$_{1A/B/D/E}$ and 5HT$_2$-like families (5HT$_{1C/2}$). Plassat et al., *EMBO J.*, 11:4779–4786 (1992) have recently reported identification of the apparent mouse homolog of REC17, which they have referred to as 5-HT$_5$. Because the primary structures of REC17 and MR22 are distinct from other known 5-HT receptors, REC17 and MR22 have been designated as novel serotonin receptors, 5-HT$_{5\alpha}$ and 5-HT$_{5\beta}$, respectively.

2) MR77

The rat MR77 clones and its human homolog correspond to a novel 5-HT receptor, more closely related in sequence to the recently cloned human S31 receptor (5-HT$_{1E}$) than any described 5-HT receptor but clearly a new member of the 5-HT$_1$ receptor family. The data presented in the preceding Examples on MR77 demonstrate that the MR77 gene encodes a novel 5-HT receptor protein that is expressed predominantly in the central nervous system. The MRNA distribution pattern in the brain is consistent with terminal fields for some serotonergic neurons. The identification of receptor genes has recently outpaced traditional pharmacological identification. It has therefore become increasingly difficult to classify novel receptor gene products on a basis other than amino acid sequence. Given that the sequence of MR77 is most similar to 5-HT$_{1E}$, the MR77 gene of this invention has been identified as another member of the 5-HT$_{1E}$ receptor subgroup.

The 5-HT$_{1B}$ and 5-HT$_{1D}$ receptors and the MR77 and 5-HT$_{1E}$ receptors form distinct subfamilies, more similar to each other collectively than to 5-HT$_{1A}$, as determined by amino acid sequence comparisons. This may be due in part to the longer putative third intracellular loop in 5-HT$_{1A}$ compared to the other receptors. Previously cloned 5-HT receptors have fallen into either 5-HT$_1$ or 5-HT$_2$ families by both significant sequence identity and pharmacological profiles.

3) REC20

As described in Example 3, degenerate PCR was used to target and identify a novel G-protein coupled receptor. The isolated clone was designated as REC20 and was determined to have a nucleotide sequence 3.1 kb in length which exhibited an open reading frame encoding a putative protein of 435 amino acids (FIG. 5). REC20 exhibited highest identity, within the conserved transmembrane domains, with the Drosophila 5-HTdrol receptor (54%). However, the entire REC20 sequence did not exhibit preferential identity to any known 5-HT receptor subgroup and is therefore classified as a novel 5-HT receptor, 5-HT$_6$.

This grouping is graphically illustrated as a dendrogram in FIG. 6 that includes three other novel serotonin receptor clones of this invention which have been identified as the putative 5-HT$_{5A}$ and 5-HT$_{5B}$ receptors, REC17 and MR22, respectively, and the 5-HT$_{1E}$-like (5-HT$_{1F}$) receptor designated MR77. From this analysis, REC20 was determined to represent a separate class of 5-HT receptors, with distant similarity more to 5-HT$_{1A}$, and 5-HTdrol receptors than other subclasses. It is perhaps significant that REC20 bears little resemblance to the 5-HT$_5$ receptors to which it was targeted. This finding speaks to the power of degenerate PCR, whereas this discovery would not have occurred with traditional low-stringency hybridization screening.

In summary, the molecular cloning and the pharmacological profile described herein of these four novel serotonin receptors, MR22, REC17, MR77 and REC20, will provide pharmacologists to study each receptor in isolation; this in turn will allow the development of rational drug design, thereby leading to successful therapeutic reagents.

5. Preparation of Synthetic Polypeptides of Novel Serotonin Receptors

A. Synthesis of Polypeptides

Synthetic polypeptides, listed in Table 3 and 4 below, were derived from the derived amino acid residue sequence of the novel serotonin receptor proteins, MR22, REC17, MR77 and REC20, prepared in Examples 1–3. Polypeptides for diagnostic use are listed in Table 3 while polypeptides for use in generating blocking reagent antisera are listed in Table 4. Methods for the preparation of synthetic polypeptides corresponding to amino acid residue sequences of portions of naturally occurring proteins translated from brain-specific mRNAs is described in U.S. Pat. No. 4,900,811, the disclosure of which is hereby incorporated by reference. The polypeptides of this invention were produced by the simultaneous multiple peptide synthesis method using the solid-phase technique described by Houghten, Proc. Natl. Acad. Sci., USA, 82:5131–5135 (1985). The peptides are hereinafter referred to by their corresponding serotonin receptor and their SEQ ID NO as listed in Table 3 and 4. In addition, the polypeptides listed in Table 4are referred to by the regions of the serotonin receptor protein from which the polypeptides were derived.

All polypeptides were synthesized in the carboxy-terminal amide form. The synthesized peptides were then analyzed by reverse phase high performance liquid chromatography (HPLC) on a Vydac C-18 column (Alltech Associates, Inc., Ill.) with a 0–60% acetonitrile linear gradient in 0.1% trifluoroacetic acid. Peptides were then purified to homogeneity by preparative HPCL using optimal conditions suggested by the analytical chromatography. Amino acid compositions and concentrations of isolated peptides were determined by subjection to 24 hour hydrolysis in 6N HCl in evacuated tubes at 110 degrees Celsius (110° C.) and subsequent analysis on a Beckman Model 6300 High Performance Analyzer. Purified peptides were separately resuspended in distilled water to form a dissolved peptide solution prior to use as compositions in the methods of this invention.

TABLE 3

| Serotonin Receptor | SEQ ID NO | AMINO ACID RESIDUE SEQUENCE |
| --- | --- | --- |
| MR77: | 36 | MIKEELNGQVLLESGEK |
|  | 37 | HSTVKSPRSELKHEKSWR |
| MR22: | 38 | WTITRHLQYTLRTRRR |
|  | 39 | VVPLPATTQAKEAPQESETV |
|  | 40 | RATVAFQTSGDSWREQKEKR |
|  | 41 | KNYNNAFKSLFTKQR |
| REC17: | 42 | VSPIPEAVEVKDASQHPQM |
|  | 43 | RSYSSAFKVFFSKQQ |
| REC20: | 44 | RKSAAKHKFPGFPRVQPES |
|  | 45 | PEVGRGLQDLSPDGGAHPVVS |
|  | 46 | SRLLKHERKNISIFKREQK |

TABLE 4

| Serotonin Receptor | SEQ ID NO | AMINO ACID RESIDUE SEQUENCE* |
| --- | --- | --- |
| MR22 |  |  |
| N-terminus | 47 | MEVCNLSGATPGIAFPPGPESCSDSPSSG-RSMGSTPGGLILSGREPPFSAFT |
| EC loop 1 | 48 | PLSLVSELSAGRRWQLGRSLCHVWISFD |
| EC loop 2 | 49 | APLLFGWGEAYDARLQRCQVSQEPSYAVF-STCG |
| EC loop 3 | 50 | WIPFFLTELVSPLCACSLPPIWKSIFLWLG |
| C-terminus | 51 | KNYNNAFKSLFTKQR |
| REC17 |  |  |
| N-terminus | 52 | MDLPINLTSFSLSTPSTLEPN-RSLDTEALRTSQSFLSAFR |
| EC loop 1 | 53 | PLSLVHELSGRRWQLGRRLCQLWIAL |
| EC loop 2 | 54 | APLLFGWGETYSELSEECQVSREPSYTVF-STVG |
| EC loop 3 | 55 | VTELISPLCSWDIPALWKSIFLW |
| C-terminus | 56 | RSYSSAFKVFFSKQQ |
| MR77 |  |  |
| N-terminus | 57 | MDFLNSSDQNLTSEELLNRMPSK |
| EC loop 1 | 58 | MPFSIVYIVRESWIMGQGLCDLWLSVD |
| EC loop 2 | 59 | FISMPPLFWRHQGNSRDDQCIIKHD-HIVSTIYSTFG |

TABLE 4-continued

| Serotonin Receptor | SEQ ID NO | AMINO ACID RESIDUE SEQUENCE* |
|---|---|---|
| EC loop 3 | 60 | WLPFFVKELVVNICEKCKISEEMSNF |
| C-terminus | 61 | YTIFNEDFKKAFQKLVRCRN |
| HumMR77 | | |
| N-terminus | 62 | MDFLNSSDQNLTSEELLNRMPSK |
| EC loop 1 | 63 | MPFSIVYIVRESWIMGQVVCDIWLSVD |
| EC loop 2 | 64 | FISVPPLFWRHQGTSDDECIIKHD-HIVSTIYSTFG |
| EC loop 3 | 65 | WLPFFVKELVVNVCDKCKISEEMSNF |
| C-terminus | 66 | YTIFNEDFKKAFQKLVRCRC |
| REC20 | | |
| N-terminus | 67 | MMDVNSSGRPDLYGHLRSLILPEVG-RGLQDLSPDGGAHPVVSSWMPHL-LSGFLEVTASPAPTWDAPPDNVS-GCGEQINYGRVEK |
| EC loop 1 | 68 | MPFVSVTOLIGGKWIFGHFFCN-VFIAMDVMCC |
| EC loop 2 | 69 | TLPPLFGWAQNUNDDKVC-LISQDFGVTIYSTAVAF |
| EC loop 3 | 70 | FTVCWLPFFLLSTARPFIC-GTSCSCIPLWVERTCLW |
| C-terminus | 71 | FFNRDLRTTYRSLLQCQYRNINR-KLSAAGMHEALKLAERPERSEFVL |

EC = extracellular
Hum = human clone
*= The sequence of the polypeptides is listed in the order it appears in the serotonin molecule from N- to C-terminus The synthetic serotonin receptor-derived polypeptides prepared as described herein are then used in ligand binding assays to determine the polypeptide's binding characteristics. The binding assays are performed as described in Example 4D with radiolabeled LSD used as a serotonin analog for binding to serotonin receptors.

6. Preparation of Polyclonal Antisera to Synthetic Polypeptides

A. Preparation of Immunogen

For preparation of a peptide immunogen, the synthetic polypeptides listed in Table 3 were prepared as described in Example 5. The preparation of polypeptide antisera to synthetic polypeptides has been described in U.S. Pat. No. 4,900,811, the disclosure of which is hereby incorporated by reference. The synthesized polypeptides were separately coupled to keyhole-limpet-hemocyanin (KLH) (Sigma, St. Louis, Mo.) using the heterobifunctional crosslinking agent, N-succinimidyl-3-(2-pyridyldithio) propionate (SPDP) (Pierce Biochemicals, Rockford, Ill.).

For the coupling procedure, 80 $\mu$l of 10 mg/ml SPDP dissolved in dimethylformamide were admixed dropwise to 400 $\mu$l 15 mg/ml KLH in 0.1M phosphate, 0.1M NaCl at pH 8.5 under continuous stirring conditions for 30 minutes at 22° C. in order to form SPDP-activated KLH. The resultant SPDP-activated KLH was then extensively dialyzed at 4° C. against a buffered solution of 0.1M phosphate and 0.1M NaCl at pH 7.4 in order to remove uncoupled SPDP. Six mg of the prepared polypeptides were first dissolved in 2 ml of 0.1M phosphate and 0.1M NaCl at pH 7.4 and then admixed with SPDP-activated KLH prepared above under continuous stirring conditions. The degree of coupling of the individual polypeptides with KLH was monitored by diluting an aliquot of the mix 1:100 at time zero, and each hour thereafter, and measuring the release of pyridine-2-thione at 343 nm in a spectrophotometer. The end point of coupling was determined to be an increase of 0.2 in absorbency, or upon visualization of precipitate at which point KLH conjugates peptide was formed, and designated polypeptide-KLH immunogen.

B. Immunization and Collection of Polyclonal Antisera

To form anti-peptide antibodies, the separate polypeptide immunogens prepared in Example 6A were emulsified using Adjuvant Complete Freund (DIFCO Laboratories, Detroit, Mich.) for the first injection and Adjuvant Incomplete Freund (DIFCO) for all subsequent injections according to the manufacturer's instructions, and the polypeptide-KLH immunogens were incorporated into the emulsion at a concentration of 2 mg/ml. One-half ml of each prepared emulsion was injected subcutaneously into each of two New Zealand white rabbits after pre-immune serum samples were collected. The emulsion was injected into rabbits three times at weekly intervals following the injection protocol as detailed. Two weeks after the last injection, blood samples were collected to check antibody titer against the specific polypeptides used as immunogens by the ELISA assay described below in Example 6C. The collected blood samples were stored at 4° C. for 12 hours, after which the samples were centrifuged at 3000×g for 20 minutes. The resultant supernatant containing anti-peptide antibodies was collected, designated polyclonal anti-polypeptide antibodies and stored at −20°C.

The polypeptides in Table 4 are also separately prepared as immunogens by conjugation with KLH as described in Example 6A. Immunization of separate rabbits for the production of antisera against each of the peptides listed above is performed as described herein. The resultant antisera are then screened by ELISA as described below.

C. ELISA to Screen Antisera Immunoreactivity

The polypeptide antibody titers and immunospecificity in sera collected from rabbits in Example 6B were determined in an enzyme-linked-immunosorbent-assay (ELISA) as described below. The antigens used in the ELISA included the immunizing polypeptides.

To determine the immunospecificity of the rabbit antisera obtained in Example 6B, ELISA assays were performed. Briefly, 50 $\mu$l of 50 $\mu$M concentrations of the polypeptides prepared in Example 5 and listed in Table 3 in a buffer consisting of 0.05M sodium carbonate ($Na_2CO_3$) and 0.02% $NaN_3$ at pH 9.0 were separately admixed into the wells of microtiter plates. The plates were maintained at 37° C. for 1 hour to permit the antigens to become operatively affixed to the well walls. After washing the antigen-coated wells with TBS, the wells were blocked with 250 $\mu$l/well of 10% bovine serum albumin (BSA) (Sigma) in TBS for 1 hour at 22°C. The blocking solution was then removed and the wells were subsequently washed five times with 250$\mu$l/well of maintenance buffer (0.05M Tris-HCl, 0.1M NaCl, 0.02% $NaN_3$, 1 mg/ml BSA, 5 mM $CaCl_2$, 0.01% Tween 20 at pH 7.4).

Fifty $\mu$l of rabbit nonimmune or specific antiserum serially diluted in maintenance buffer were then admixed to the washed wells to form an immunoreaction admixture, that was maintained for 1 hour at 37° C. to allow formation of a solid-liquid phase immunoreaction products. The wells were then washed 3 times with maintenance buffer followed by admixture of 50 $\mu$l of 1.0 $\mu$g/ml of secondary antibody (polyclonal biotinylated goat-anti-rabbit-IgG) (Pierce Chemicals, Rockford, Ill.) diluted in maintenance buffer to each well for the detection of immunoreactant products. The plates were maintained for 1 hour at 37° C. after which time the secondary antibody solution was removed.

After washing the wells as described above, 50 $\mu$l of 1.0 $\mu$g/ml streptavidin-alkaline-phosphatase (Pierce Biochemicals) in maintenance buffer were admixed into each well and maintained for 30 minutes at 37° C. Detection of specific immunoreaction products was obtained by admixture of 150 $\mu$l/well of 5 mg/ml p-nitrophenylphosphate (PNPP) (Pierce Biochemicals) in 0.1M diethanolamine and 0.02% $NaN_3$ at pH 9.0 followed by measurement of the change in absorbance at 405 nm over time using the EL312 Microplate Bio-Kinetics Reader and the KinetiCalc Software Program (Biotek Instruments, Inc., Vt.). Nonspecific binding was considered as the measured absorbance in 10% BSA blocked wells which served as negative controls without the preceding coating of a specific protein or peptide. Under the described conditions, nonspecific binding never exceeded more than 5% of the specific binding. Rabbit anti-polypeptide antisera which exhibited immunoreactivity that produced an optical density change at 405 nm of greater than 20 delta per minute using the kinetic program as compared to the immunoreactivity of pre-immune serum toward the immunogen polypeptides was selected for use as separate anti-peptide antibodies, and also selected for further purification below.

Rabbit antisera, that are obtained in Example 6B against the polypeptides in Table 4are screened for immunoreactivity to the respective polypeptide immunogen as described above. Rabbit antisera which exhibited significant immunoreactivity as compared to the pre-immune sera toward each of the polypeptide immunogens are further purified and analyzed as described below.

D. Purification of Anti-Polypeptide Antibodies

Purification of the IgG fraction from the rabbit antisera collected above, which showed significant reactivity towards the immunizing polypeptides in Table 3, was conducted by ammonium-sulfate precipitation (0–45%), followed by purification of IgG on an ion-exchange Mono Q column (Pharmacia LKB, Piscataway, N.J.) connected to a fast protein liquid chromatography (FPLC) system (Pharmacia). Immunoaffinity purification of the pooled immunoreactive IgG-fraction was performed by passing approximately 100 mg of the IgG over a 5 ml column containing 3 mg of individual polypeptides prepared in Example 5 coupled to Sepharose 4B (Pharmacia) according to manufacturer's instructions. After a thorough washing of the column with 5 column volumes of 0.05 M Tris-HCl and 1M NaCl at pH 7.4 to remove unbound antibodies, the bound IgG was eluted with two column volumes of 0.1M glycine-HCl at pH 2.5. The eluted protein for each antibody was monitored by absorbance at 280 nm and the IgG concentrations determined from the extinction coefficient of 13.5.

The eluted IgG was immediately dialyzed against TBS-Az, concentrated against 50% sucrose for approximately 3–4 hours and once more extensively dialyzed against TBS-Az to a final concentration of 3–4 mg/ml. Analysis by 4–15% sodium dodecyl sulfate-polyacrylamide gel electrophoresis (SDS-PAGE) of reduced and non-reduced samples revealed greater than 95% pure IgG. The immunoaffinity-purified anti-polypeptide antibodies prepared herein were used as diagnostic reagents in the methods of this invention.

Purification of the IgG fraction from the rabbit antisera collected above, which showed significant reactivity towards the immunizing polypeptides in Table 4, is conducted following the purification procedures described above. The immunoaffinity-purified anti-polypeptide antibodies prepared herein are used as blocking reagents in the methods of this invention.

7. Analysis of the Serotonergic Agents on Suprachiasmatic *Neuronal Activity*

The effects of serotinergic agents on the neuronal activity as measured against circadian time in the suprachiasmatic nucleus (SCN) were measured. The procedures used in measuring the circadian time involving slice preparation and maintenance, electrophysiological recordings, and data analysis were performed as described by Prosser et al., *J. Neurosci.*, 9:1073–1081 (1989). Slice treatment consisted of stopping perfusion and replacing bath medium for 1 hour with medium containing no additional compounds (=control) or 8-OH-DPAT. In blocking experiments, bath medium was first replaced for 15 minutes with perfusion medium containing either pindolol or ritanserin (dissolved in 100% ethanol and then diluted to the proper concentration), followed by replacement for 1 hour with medium containing 8-OH-DPAT and either pindolol or ritanserin, followed by an additional 15 minute treatment with medium containing pindolol or ritanserin. This was followed by the normal perfusion medium.

The results of testing the effects of serotonergic agents on the SCN neuronal activity are shown in FIG. 7. Evident from the bar graphs is the alteration of neuronal activity as measured in Hz over time by the serotonin receptor agonist 8-OH-DPAT. This data indicate that the agonist induces a phase advance of about 2–3 hours in the circadian rhythm of spontaneous neuronal activity in the SCN (at CT*). In addition, the antagonist ritaserin blocks the 8-OH-DPAT-dependent phase shift whereas the antagonist pindolol has no effect. This pharmacological profile of the serotonin-induced phase shift is unique to REC20; no other known 5-HT receptors exhibit this profile.

These results indicate that the therapeutic reagents described herein which are specific for $5\text{-}HT_6$ are useful for inhibiting the receptor, and for resetting the phase of the circadian rhythm. The phase adjustment of the 24-hour circadian clock has applications in treatment to avoid or ablate jet lag, adjust the clock in the work force where there are abnormal or changing work shifts, and for synchronization of the clock in the elderly or others where there is a dysynchronization of the clock.

8. Screening for Serotonin Receptor Agonists and Antagonists

Four new serotonin receptors have been discovered as described in this invention for the neurohormone serotonin, bringing the total number known to about 12. More than 12, but fewer than 25, receptors for serotonin are probably expressed by humans and other animals. Agonism or antagonism at any one of these receptors initiates physiological sequelae distinct from action at any of the others due to differences in each particular receptor with respect to 1) its anatomical sites of expression, 2) its subcellular sites of expression, and 3) the second messenger systems to which the receptor couples. Pharmaceutical compositions that discriminate amongst the receptors, especially those selective for a single receptor type, would be efficacious in treatment of diseases selectively involving systems utilizing that certain receptor while initiating fewer or no side effects due to agonism or antagonism at other serotonin receptor types unrelated to the disease state. Therefore, identifying compounds that are selective agonists or antagonists for the 4 new receptors, as well as for all other serotonin receptors is of great interest and significance.

Presently known serotonin receptor-binding compounds have fairly broad spectra of binding; that is, they bind to many, but usually not all, receptor subtypes. Three general strategies can be used to identify novel selective compounds. Each strategy ultimately requires screening membrane preparations containing individually each of the 4 novel receptors as well as other receptors.

Strategy 1 relies on the systematic production of compounds that differ slightly in their chemical structures from compounds already known to bind. Once synthesized, each new compound is screened for its ability to bind selectively to membranes carrying any of the expressed receptors. Newly identified compounds that bind are subsequently examined in functional studies to determine 1) whether they have agonistic or antagonistic effects, 2) their toxicology, 3) their effectiveness in crossing the blood-brain barrier, and 4) their effect upon physiological function, especially as it concerns systems utilizing serotonergic transmission in diseased patients.

Strategy 2 involves screening compounds not necessarily known to interact with serotonin receptors for their ability to interact with a particular receptor of interest, for example REC20. Compounds shown to bind to REC20 are subsequently studied for their abilities to bind to other receptors, and examined according to the list of four issues listed in the preceding paragraph. REC20-binding compounds would additionally serve as lead compounds for the development of compounds with related molecular structures that might have more desirable selectivity, affinity, permeability, solubility, toxicology, efficacy in treatment.

Strategy 3 involves a multiplex screening of all compounds examined in Strategy 2 for their abilities to interact with membranes containing any of the cloned receptors. Whereas in Strategy 2, if an interest arises primarily in pharmacologically active ligands such as REC20 because REC20 is likely to be involved in circadian rhythmicity and sleep and new compounds need to be identified that are selective for these physiological phenomena, Strategy 3 takes the view that any compound that is a selective agonist/antagonist for any of the several serotonin receptors has selective efficacy for treatment of particular but not yet specified diseases. The new receptor-selective ligands identified are tested for their physiological effects and the outcomes used to define a list of candidate applications. Many of these candidate applications are foreseen because of the sites of expression of the various receptor types and the differential activities of known broad-range serotonin receptor-selective pharmaceuticals.

The foregoing written specification is considered to be sufficient to enable one skilled in the art to practice the invention. Indeed, various modifications of the invention in addition to those shown and described herein will become apparent to those skilled in the art from the foregoing description and fall within the scope of the appended claims.

What is claimed is:

1. An isolated DNA segment encoding a 5-HT$_{5\alpha}$ serotonin receptor REC17 comprising a nucleotide sequence that codes the amino acid residue sequence shown in SEQ ID NO 4.

2. The isolated DNA segment of claim 1 wherein said DNA segment comprises the nucleotide sequence shown in SEQ ID NO 3 from base 150 to 1220.

3. A vector comprising the DNA segment of claim 1, wherein said vector is adapted for expression of said serotonin receptor in a host cell containing said vector.

4. The vector of claim 3 wherein said vector is adapted for expression of said serotonin receptor in a mammalian host cell.

5. An isolated mammalian cell comprising the DNA segment of claim 1.

6. The isolated mammalian cell of claim 5 wherein said DNA is present in a vector adapted for expression of said serotonin receptor in said mammalian cell.

7. The isolated mammalian cell of claim 6 that further comprises a cell surface serotonin receptor expressed from said vector.

8. An isolated DNA segment encoding a 5-HT$_{5\beta}$, serotonin receptor MR22 comprising a nucleotide sequence that codes the amino acid residue sequence shown in SEQ ID NO 2.

9. The isolated DNA segment of claim 8, wherein said DNA segment comprises the nucleotide sequence shown in SEQ ID NO 1 from base 303 to 1412.

10. A vector comprising the DNA segment of claim 8, wherein said vector is adapted for expression of said serotonin receptor in a host cell containing said vector.

11. The vector of claim 10 wherein said vector is adapted for expression of said serotonin receptor in a mammalian host cell.

12. An isolated mammalian cell comprising the DNA segment of claim 8.

13. The isolated mammalian cell of claim 12 wherein said DNA is present in a vector adapted for expression of said serotonin receptor in said mammalian cell.

14. The isolated mammalian cell of claim 13 that further comprises a cell surface serotonin receptor expressed from said vector.

* * * * *